(12) United States Patent
Modis et al.

(10) Patent No.: US 8,673,552 B2
(45) Date of Patent: *Mar. 18, 2014

(54) DRUGGABLE REGIONS IN THE DENGUE VIRUS ENVELOPE GLYCOPROTEIN AND METHODS OF USING THE SAME

(75) Inventors: Yorgo Modis, Brookline, MA (US); Stephen C. Harrison, Cambridge, MA (US)

(73) Assignee: Children's Medical Center Corporation, Boston, MA (US)

( * ) Notice: Subject to any disclaimer, the term of this patent is extended or adjusted under 35 U.S.C. 154(b) by 410 days.

This patent is subject to a terminal disclaimer.

(21) Appl. No.: 12/430,360

(22) Filed: Apr. 27, 2009

(65) Prior Publication Data

US 2010/0105151 A1 Apr. 29, 2010

Related U.S. Application Data

(63) Continuation of application No. 11/257,777, filed on Oct. 24, 2005, now Pat. No. 7,524,624, which is a continuation of application No. PCT/US2004/012433, filed on Apr. 22, 2004.

(60) Provisional application No. 60/464,873, filed on Apr. 22, 2003, provisional application No. 60/505,654, filed on Sep. 24, 2003.

(51) Int. Cl.
*C12Q 1/70* (2006.01)
*A61K 39/12* (2006.01)

(52) U.S. Cl.
USPC .................................... 435/5; 424/218.1

(58) Field of Classification Search
None
See application file for complete search history.

(56) References Cited

U.S. PATENT DOCUMENTS 6,136,561 A * 10/2000 Ivy et al. ............... 435/69.3
7,524,624 B2 * 4/2009 Modis et al. ............... 435/5
2005/0271677 A1 12/2005 Garry et al.

OTHER PUBLICATIONS

Bressanelli, et al., Structure of a flavivirus envelope glycoprotein in its low-pH-induced membrane fusion conformation, The EMBO Journal, 23: 728-738 (2004).
Gibbons, et al., Purification and Crystallization Reveal Two Types of Interactions of the Fusion Protein Homotrimer of Semliki Forest Virus, Journal of Virology, 78(7): 3514-3523 (2004).
International Search Report for PCT/US04/12433 mailed Jun. 16, 2005.

* cited by examiner

*Primary Examiner* — Stacy B. Chen
(74) *Attorney, Agent, or Firm* — Edwards Wildman Palmer LLP; Peter F. Corless

(57) ABSTRACT

The present invention relates to novel druggable regions discovered in dengue virus envelope glycoprotein, or dengue virus E protein, which is a class II viral E protein. The present invention further relates to methods of using the druggable regions to screen potential candidate therapeutics for diseases caused by viruses having class II E proteins, e.g. viral fusion inhibitors.

12 Claims, 11 Drawing Sheets

SEQUENCE LISTING

<160> NUMBER OF SEQ ID NOS: 6

<210> SEQ ID NO 1
<211> LENGTH: 495
<212> TYPE: PRT
<213> ORGANISM: Dengue virus type 2

<400> SEQUENCE: 1

```
Met Arg Cys Ile Gly Ile Ser Asn Arg Asp Phe Val Glu Gly Val Ser
  1               5                  10                  15

Gly Gly Ser Trp Val Asp Ile Val Leu Glu His Gly Ser Cys Val Thr
             20                  25                  30

Thr Met Ala Lys Asn Lys Pro Thr Leu Asp Phe Glu Leu Ile Lys Thr
         35                  40                  45

Glu Ala Lys Gln Pro Ala Thr Leu Arg Lys Tyr Cys Ile Glu Ala Lys
     50                  55                  60

Leu Thr Asn Thr Thr Thr Asp Ser Arg Cys Pro Thr Gln Gly Glu Pro
 65                  70                  75                  80

Thr Leu Asn Glu Glu Gln Asp Lys Arg Phe Val Cys Lys His Ser Met
                 85                  90                  95

Val Asp Arg Gly Trp Gly Asn Gly Cys Gly Leu Phe Gly Lys Gly Gly
            100                 105                 110

Ile Val Thr Cys Ala Met Phe Thr Cys Lys Lys Asn Met Glu Gly Lys
        115                 120                 125

Ile Val Gln Pro Glu Asn Leu Glu Tyr Thr Val Val Ile Thr Pro His
    130                 135                 140

Ser Gly Glu Glu His Ala Val Gly Asn Asp Thr Gly Lys His Gly Lys
145                 150                 155                 160

Glu Val Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Lys Asp Lys Ala Trp Leu Val
        195                 200                 205

His Arg Gln Trp Phe Leu Asp Leu Pro Leu Pro Trp Leu Pro Gly Ala
    210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
```

```
                    290                 295                 300
Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Thr Pro
                325                 330                 335

Phe Glu Ile Met Asp Leu Glu Lys Arg His Val Leu Gly Arg Leu Thr
            340                 345                 350

Thr Val Asn Pro Ile Val Thr Glu Lys Asp Ser Pro Val Asn Ile Glu
                355                 360                 365

Ala Glu Pro Pro Phe Gly Asp Ser Tyr Ile Ile Ile Gly Val Glu Pro
370                 375                 380

Gly Gln Leu Lys Leu Asp Trp Phe Lys Lys Gly Ser Ser Ile Gly Gln
385                 390                 395                 400

Met Phe Glu Thr Thr Met Arg Gly Ala Lys Arg Met Ala Ile Leu Gly
                405                 410                 415

Asp Thr Ala Trp Asp Phe Gly Ser Leu Gly Gly Val Phe Thr Ser Ile
            420                 425                 430

Gly Lys Ala Leu His Gln Val Phe Gly Ala Ile Tyr Gly Ala Ala Phe
                435                 440                 445

Ser Gly Val Ser Trp Thr Met Lys Ile Leu Ile Gly Val Ile Ile Thr
450                 455                 460

Trp Ile Gly Met Asn Ser Arg Ser Thr Ser Leu Ser Val Ser Leu Val
465                 470                 475                 480

Leu Val Gly Ile Val Thr Leu Tyr Leu Gly Val Met Val Gln Ala
                485                 490                 495

<210> SEQ ID NO 2
<211> LENGTH: 394
<212> TYPE: PRT
<213> ORGANISM: Dengue virus type 2

<400> SEQUENCE: 2

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
                20                  25                  30

Thr Met Ala Lys Asn Lys Pro Thr Leu Asp Phe Glu Leu Ile Lys Thr
            35                  40                  45

Glu Ala Lys Gln Pro Ala Thr Leu Arg Lys Tyr Cys Ile Glu Ala Lys
        50                  55                  60

Leu Thr Asn Thr Thr Thr Asp Ser Arg Cys Pro Thr Gln Gly Glu Pro
65                  70                  75                  80

Thr Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Met Phe Thr Cys Lys Lys Asn Met Glu Gly Lys
        115                 120                 125

Ile Val Gln Pro Glu Asn Leu Glu Tyr Thr Val Val Ile Thr Pro His
    130                 135                 140

Ser Gly Glu Glu His Ala Val Gly Asn Asp Thr Gly Lys His Gly Lys
145                 150                 155                 160

Glu Val Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
```

```
                            180                 185                 190
Phe Asn Glu Met Val Leu Leu Gln Met Lys Asp Lys Ala Trp Leu Val
            195                 200                 205
His Arg Gln Trp Phe Leu Asp Leu Pro Leu Pro Trp Leu Pro Gly Ala
210                 215                 220
Asp Thr Gln Gly Ser Asn Trp Ile Gln Lys Glu Thr Leu Val Thr Phe
225                 230                 235                 240
Lys Asn Pro His Ala Lys Lys Gln Asp Val Val Val Leu Gly Ser Gln
                245                 250                 255
Glu Gly Ala Met His Thr Ala Leu Thr Gly Ala Thr Glu Ile Gln Met
            260                 265                 270
Ser Ser Gly Asn Leu Leu Phe Thr Gly His Leu Lys Cys Arg Leu Arg
        275                 280                 285
Met Asp Lys Leu Gln Leu Lys Gly Met Ser Tyr Ser Met Cys Thr Gly
    290                 295                 300
Lys Phe Lys Val Val Lys Glu Ile Ala Glu Thr Gln His Gly Thr Ile
305                 310                 315                 320
Val Ile Arg Val Gln Tyr Glu Gly Asp Gly Ser Pro Cys Lys Thr Pro
                325                 330                 335
Phe Glu Ile Met Asp Leu Glu Lys Arg His Val Leu Gly Arg Leu Thr
            340                 345                 350
Thr Val Asn Pro Ile Val Thr Glu Lys Asp Ser Pro Val Asn Ile Glu
        355                 360                 365
Ala Glu Pro Pro Phe Gly Asp Ser Tyr Ile Ile Gly Val Glu Pro
    370                 375                 380
Gly Gln Leu Lys Leu Asp Trp Phe Lys Lys
385                 390

<210> SEQ ID NO 3
<211> LENGTH: 34
<212> TYPE: PRT
<213> ORGANISM: Dengue virus type 2

<400> SEQUENCE: 3

Ser Ser Ile Gly Gln Met Phe Glu Thr Thr Met Arg Gly Ala Lys Arg
1               5                   10                  15
Met Ala Ile Leu Gly Asp Thr Ala Trp Asp Phe Gly Ser Leu Gly Gly
            20                  25                  30
Val Phe

<210> SEQ ID NO 4
<211> LENGTH: 35
<212> TYPE: PRT
<213> ORGANISM: Dengue virus type 2

<400> SEQUENCE: 4

Ala Ile Leu Gly Asp Thr Ala Trp Asp Phe Gly Ser Leu Gly Gly Val
1               5                   10                  15
Phe Thr Ser Ile Gly Lys Ala Leu His Gln Val Phe Gly Ala Ile Tyr
            20                  25                  30
Gly Ala Ala
        35

<210> SEQ ID NO 5
<211> LENGTH: 46
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 5
cttctagatc tcgagtaccc gggaccatgc gctgcatagg aatatc                46

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gctctagagt cgactattat cctttcttga accag                            35
```

DRUGGABLE REGIONS IN THE DENGUE VIRUS ENVELOPE GLYCOPROTEIN AND METHODS OF USING THE SAME

RELATED APPLICATIONS

This patent application is a continuation of U.S. application Ser. No. 11/257,777, filed Oct. 24, 2005, now U.S. Pat. No. 7,524,624; which is a continuation of Application No. PCT/US04/012433, filed Apr. 22, 2004, which claims the benefit of priority to U.S. Provisional Patent Application Ser. No. 60/464,873, filed Apr. 22, 2003, and U.S. Provisional Patent Application Ser. No. 60/505,654, filed Sep. 24, 2003.

GOVERNMENT SUPPORT

The subject invention was made in part with government support under Grant Number CA 13202 awarded by the NIH and Grant Number LT00538 awarded by the Human Frontier Science Program Accordingly, the U.S. Government has certain rights in this invention.

FIELD OF THE INVENTION

The present invention relates to novel druggable regions in the dengue virus envelope glycoprotein and methods of using the same, e.g. for drug discovery.

BACKGROUND OF THE INVENTION

Dengue virus, a member of the flavivirus family, imposes one of the largest social and economic burdens of any mosquito-borne viral pathogen. There is no specific treatment for infection, and control of dengue virus by vaccination has proved elusive. Several other flaviviruses are important human pathogens, including yellow fever, West Nile, tick-borne encephalitis (TBE) and Japanese encephalitis viruses (JE).

Three structural proteins ("C", "M", and "E") and a lipid bilayer package the positive-strand RNA genome of flaviviruses. The core nucleocapsid protein, C, assembles with RNA on the cytosolic face of the endoplasmic reticulum membrane. The assembling core buds through the ER membrane, thereby acquiring an envelope that contains the major envelope glycoprotein, E, and the so-called precursor membrane protein, PrM. The particle passes through the secretory pathway, where a furin-like protease cleaves PrM to M in a late trans-Golgi compartment. The cleavage, which removes most of the ectodomain of PrM, releases a constraint on E and primes the particle for low-pH triggered membrane fusion. Uncleaved, immature particles are not fusion competent.

Enveloped viruses enter cells by membrane fusion E, which mediates both receptor binding and fusion, is a so-called "class II" viral fusion protein. Two classes of viral "fusion machines" have been identified so far. Class I viral fusion proteins include those of the myxo- and paramyxoviruses (e.g., influenza), the retroviruses (e.g., HIV), and the filoviruses (e.g., Ebola). Class II fusion proteins are found in not only the flaviviruses (yellow fever, West Nile, etc.), but also the alphaviruses (Semliki Forest virus, Sindbis virus, etc. . . . ), as well as Hepatitis C. The structural characteristics of the two classes are quite different, but both accomplish the same "reaction"—viz., fusion of two lipid bilayers.

The more familiar class I fusion proteins, exemplified by the hemagglutinin (HA) of influenza virus and gp120/gp41 of HIV, have a "fusion peptide" at or near the N-terminus of an internal cleavage point. This hydrophobic and glycine-rich segment, buried in the cleaved-primed trimer of the class I fusion protein, emerges when a large-scale conformational rearrangement is triggered by low pH (in the case of HA), receptor binding (in the case of gp120/gp41), or other cell-entry related signal. The likely sequence of events that follow include an interaction of the fusion peptide with the target-cell membrane and a refolding of the trimer. The latter step brings together the fusion peptide and viral-membrane anchor, thereby drawing together the cellular and viral membranes and initiating the bilayer fusion process.

The class II proteins, found so far in flaviviruses and alphaviruses, have evolved a structurally different but mechanistically related fusion architecture. As in class I proteins, a proteolytic cleavage (of PrM to M in flaviviruses, or of pE2 to E2 in alphaviruses) yields mature virions, with the fusion proteins in a metastable conformation, primed for fusion. The fusion peptide, an internal loop at the tip of an elongated subdomain of the protein, is buried at a protein interface and becomes exposed in the conformational change initiated by exposure to low pH.

The mechanism of fusion of class II viral fusion proteins is not well-understood, and there are no therapeutics that can specifically inhibit the fusion of such proteins. Only the pre-fusion structures of one flaviviral and one alphaviral envelope protein have been determined to date. Because fusion is a key step in viral infectivity, a better understanding of the mechanism of class II envelope proteins and identification of druggable regions within such proteins will further development of therapeutics that can specifically inhibit viral infection by flaviviruses, alphaviruses, and hepatitis viruses.

SUMMARY OF THE INVENTION

Dengue virus E protein in both its pre- and post-fusion conformations has been crystallized and the structures solved as described in detail below, thereby providing information about the structure of the polypeptide, and druggable regions, domains and the like contained therein, all of which may be used in rational-based drug design efforts.

Accordingly, the present invention provides in part novel druggable regions in viral class II E proteins. The interaction of a drug with such regions, or the modulation of the activity of such regions with a drug, could inhibit viral fusion and hence viral infectivity. In one aspect, the present invention provides methods of screening compounds against these druggable regions in order to discover a candidate therapeutic for a disease caused by a virus having a class II protein, for example a small molecule viral fusion inhibitor. Diseases for which a therapeutic candidate may be screened include dengue fever, dengue hemorrhagic fever, tick-borne encephalitis, West Nile virus disease, yellow fever, Kyasanur Forest disease, louping ill, hepatitis C, Ross River virus disease, and O'nyong fever. In one embodiment, a method for identifying a candidate therapeutic for a disease caused by a virus having class II E protein, comprises contacting a class II E protein which comprises a druggable region with a compound, wherein binding of said compound indicates a candidate therapeutic. Compounds may be in certain embodiments be selected from the following classes of compounds: polypeptides, peptidomimetics, and small molecules, and may be selected from a library of compounds. Such a library may be generated by combinatorial synthetic methods. Binding may be assayed either in vitro or in vivo. In certain embodiments of this method, the protein is dengue virus E protein and comprises at least one residue from a druggable region of dengue virus E protein. Such druggable regions also may be utilized in the structure determination, drug screening, drug design, and other methods described and claimed herein.

In one embodiment, the druggable region is comprised of the k1 hairpin or a portion thereof. In certain embodiments, the k1 hairpin may be comprised of at least one of residues 268-280 of a dengue virus E protein or the homologous residues in other class II E protein. In other embodiments, the druggable region or active site region may be comprised of the k1 hairpin and at least one of residues 47-54, 128-137, and 187-207.

In yet another embodiment, the druggable region may comprise the regions involved in the binding of residues 396-429 (the "stem" region of dengue envelope protein E) binds to the trimeric, post-fusion form of dengue virus E protein or other flavivirus E protein. In one embodiment, the druggable region is comprised of the stem region or a portion thereof. The stem region comprises residues 396-447, or fragments thereof, for example 396-429 and 413-447. In another embodiment, the druggable region is comprised of the channel in which the stem region binds. The channel is comprised of the residues at the trimer interface formed by domain II of each subunit in the trimer. Domain II consists of residues 52-132 and 193-280. A second region is the channel where the stem binds, formed by residues in domain II.

In another embodiment, the druggable region is comprised of the domain I-III region. In certain embodiments, the domain region may be comprised of at least one of residues 38-40; 143-147; 294-296; and 354-365 of a dengue virus E protein or the homologous residues in other class II E protein. In other embodiments, the druggable region may be comprised of the domain I-domain III linker (residues 294-301).

In yet another embodiment, a druggable region is comprised of the fusion loop or a portion thereof.

Other regions of protein may in certain embodiments comprise a druggable region. For example, the hydrophobic core beneath the k1 hairpin or a portion thereof may comprise a druggable region. In another example, a druggable region may comprise domain II or a portion thereof. In still another example, a druggable region may comprise domain III or a portion thereof. In other examples, the pH-dependent hinge may serve as a druggable region. Further, a region or portion of a region of the E protein involved in trimerization, such as for example, the regions of domain II involved in trimerization, may present a druggable region. A region or a portion of a region involved in the stem fold back conformational change may comprise a druggable region, for example, such regions as the stem-domain II contact regions, the trimeric N terminal inner core, and C terminal outer layer surfaces on the clustered domains II, as well as the 53-residue stem. In certain embodiments, a druggable region may consist of the entire fragment of the E protein spanning residues 1-395.

In another aspect, the present invention is directed towards methods for identifying a candidate therapeutic for a disease caused by a virus having class II E protein. In certain embodiments, such methods comprise contacting a class II E protein which comprises a druggable region with a compound, wherein the modulation of the activity of said E protein indicates a candidate therapeutic. In other embodiments, such methods comprise contacting a class II E protein which comprises a druggable region with a compound, wherein the preclusion of the movement or interaction of said druggable region indicates a candidate therapeutic. In still other embodiments, the modulation of the function or activity of said E protein involves precluding the completion of the post-fusion conformational change. In yet another embodiment, the modulation of the function or activity of said E protein involves interfering with the first stage of the conformational change. In another embodiment, a method for identifying a candidate therapeutic for a disease caused by a virus having class II E protein comprises contacting a class II E protein which comprises a druggable region with a compound, wherein the inhibition of fusion in said virus indicates a candidate therapeutic. In yet another embodiment, a method for identifying a candidate therapeutic for a disease caused by a virus having class II E protein, comprising contacting a class II E protein which comprises a druggable region with a compound, wherein the inhibition of viral infectivity of said virus indicates a candidate therapeutic. In still another embodiment, a method for identifying a candidate therapeutic for a disease caused by a virus having class II E protein comprises contacting a class II E protein which comprises a druggable region with a compound, wherein the reduction of at least one symptom of said disease in a subject indicates a candidate therapeutic.

In another aspect, all of the information learned and described herein about class II E proteins may be used in methods of designing modulators of one or more of their biological activities. In one embodiment, a method for designing a modulator for the prevention or treatment of a disease caused by a virus having class II E protein, comprises: (a) providing a three-dimensional structure for a class II E protein; (b) identifying a potential modulator for the prevention or treatment of disease caused by a virus having class II E protein by reference to the three-dimensional structure; (c) contacting a class II E protein with the potential modulator; and (d) assaying the activity of the class II E protein or determining the viability of the virus having said class II E protein after contact with the modulator, wherein a change in the activity of the polypeptide or the viability of the virus indicates that the modulator may be useful for prevention or treatment of a virus-related disease or disorder. In certain embodiments, the potential modulator is identified by reference to the three-dimensional structure of a flavivirus E protein. In some embodiments, the flavivirus E protein is dengue virus E protein. In other embodiments, the potential modulator is identified by reference to the three-dimensional structure comprising a druggable region or fragment of a flavivirus E protein.

In yet another aspect, all of the information learned and described herein about class II E proteins may be used in methods of identifying new druggable regions in class II E proteins, or identifying the novel druggable regions of the invention in class II E proteins other than dengue virus E protein. In one embodiment, a method for identifying a druggable region of a class II E protein, the method comprises: (a) obtaining crystals of a polypeptide comprising (1) an amino acid sequence comprising SEQ ID NO:2; or (2) an amino acid sequence having at least about 85% identity with the amino acid sequence comprising SEQ ID NO:2; and having at least one biological activity of a class II E protein, such that the three dimensional structure of the crystallized polypeptide may be determined to a resolution of 3.5 Å or better; (b) determining the three dimensional structure of the crystallized polypeptide using X-ray diffraction; and (c) identifying a druggable region of the crystallized polypeptide based on the three-dimensional structure of the crystallized polypeptide. In certain embodiments, the druggable region is a region that binds a detergent, and/or may comprise a region of the polypeptide that is exposed upon a conformational change. In yet another embodiment, a method for designing a candidate modulator for screening for modulators of a polypeptide, comprises: (a) providing the three dimensional structure of a druggable region of a polypeptide comprising (1) an amino acid sequence comprising SEQ ID NO:2; or (2) an amino acid sequence having at least about 85% identity with the amino acid sequence comprising SEQ ID NO:2; and having at least one biological activity of a class II E protein; and (b) designing a candidate modulator based on the three dimensional structure of the druggable region of the polypeptide.

In yet another aspect, all of the information learned and described herein about class II E proteins may be used in methods of identifying modulators of the activity of a class II E protein. In one embodiment, a computer-assisted method for identifying an modulator of the activity of a class II E protein, comprises: (a) supplying a computer modeling application with a set of structure coordinates as listed in PDB accession numbers 1OKE or 1OAN or 1OK8 for the atoms of the amino acid residues from any of the above-described druggable regions of class II E protein so as to define part or all of a molecule or complex; (b) supplying the computer modeling application with a set of structure coordinates of a chemical entity; and (c) determining whether the chemical entity is expected to bind to or interfere with the molecule or complex, wherein determining whether the chemical entity is expected to bind to or interfere with the molecule or complex comprises performing a fitting operation between the chemical entity and a druggable region of the molecule or complex, followed by computationally analyzing the results of the fitting operation to quantify the association between the chemical entity and the druggable region. These methods may further comprise supplying or synthesizing the potential modulator, then assaying the potential modulator to determine whether it modulates class II E protein activity. In another embodiment, a method for identifying a potential modulator for the prevention or treatment of a disease caused by a virus having class II E protein comprises: (a) providing the three dimensional structure of a crystallized polypeptide comprising: (1) an amino acid sequence comprising SEQ ID NO:2; or (2) an amino acid sequence having at least about 85% identity with the amino acid sequence comprising SEQ ID NO:2; or (3) an amino acid sequence comprising at least one druggable region of SEQ ID NO: 2; or (4) an amino acid sequence comprising a sequence having at least about 85% identity with at least one druggable region of SEQ ID NO: 2; and having at least one biological activity of a class II E protein; (b) obtaining a potential modulator for the prevention or treatment of said disease based on the three dimensional structure of the crystallized polypeptide; (c) contacting the potential modulator with a second polypeptide comprising at least 50% identical to the amino acid sequence comprising SEQ ID NO: 2 and having at least one biological activity of a class II E protein; which second polypeptide may optionally be the same as the crystallized polypeptide; and (d) assaying the activity of the second polypeptide, wherein a change in the activity of the second polypeptide indicates that the compound may be useful for prevention or treatment of a disease caused by a virus having class II E protein. In yet another embodiment, a method for identifying a potential modulator of a polypeptide from a database comprises: (a) providing the three-dimensional coordinates for a plurality of the amino acids of a polypeptide comprising: (1) an amino acid sequence comprising SEQ ID NO:2; or (2) an amino acid sequence having at least about 85% identity with the amino acid sequence comprising SEQ ID NO:2; or (3) an amino acid sequence comprising at least one druggable region of SEQ ID NO: 2; or (4) an amino acid sequence comprising a sequence having at least about 85% identity with at least one druggable region of SEQ ID NO: 2; and having at least one biological activity of a class II E protein; (b) identifying a druggable region of the polypeptide; and (c) selecting from a database at least one potential modulator comprising three dimensional coordinates which indicate that the modulator may bind or interfere with the druggable region.

In still another aspect the present invention provides crystallized E proteins, fragments thereof, and E protein or protein fragment complexes, and methods of using the same, in methods for determining the structures of homologues of dengue virus E protein and its complexes (for example, the trimer of E proteins formed upon fusion with a membrane), or novel crystallized E proteins, fragments thereof, and E protein or protein fragment complexes. In one embodiment, a method for determining the crystal structure of a homolog of a polypeptide comprises: (a) providing the three dimensional structure of a first crystallized polypeptide comprising (1) an amino acid sequence comprising SEQ ID NO:2; or (2) an amino acid sequence having at least about 85% identity with the amino acid sequence comprising SEQ ID NO:2; or (3) an amino acid sequence comprising at least one druggable region of SEQ ID NO: 2; or (4) an amino acid sequence comprising a sequence having at least about 85% identity with at least one druggable region of SEQ ID NO: 2; and having at least one biological activity of a class II E protein; (b) obtaining crystals of a second polypeptide comprising an amino acid sequence that is at least 50% identical to the amino acid sequence comprising SEQ ID NO: 2 and having at least one biological activity of a class II E protein, such that the three dimensional structure of the second crystallized polypeptide may be determined to a resolution of 3.5 Å or better; and (c) determining the three dimensional structure of the second crystallized polypeptide by x-ray crystallography based on the atomic coordinates of the three dimensional structure provided in step (a). In another embodiment, a method for obtaining structural information about a molecule or a molecular complex of unknown structure comprises: (a) crystallizing the molecule or molecular complex; (b) generating an x-ray diffraction pattern from the crystallized molecule or molecular complex; and (c) applying at least a portion of the structure coordinates of PDB accession numbers 1OKE or 1OAN to the x-ray diffraction pattern to generate a three-dimensional electron density map of at least a portion of the molecule or molecular complex whose structure is unknown. In still another embodiment, a method for making a crystallized complex comprising a polypeptide and a candidate modulator comprises: (a) crystallizing a polypeptide comprising (1) an amino acid sequence comprising SEQ ID NO:2; or (2) an amino acid sequence having at least about 85% identity with the amino acid sequence comprising SEQ ID NO:2; or (3) an amino acid sequence comprising at least one druggable region of SEQ ID NO: 2; or (4) an amino acid sequence comprising a sequence having at least about 85% identity with at least one druggable region of SEQ ID NO: 2; and having at least one biological activity of a class II E protein; such that crystals of the crystallized polypeptide will diffract x-rays to a resolution of 5 Å or better; and (b) soaking the crystals in a solution comprising a potential modulator.

Finally, the present invention provides modulators (in certain embodiments, inhibitors) of class II E protein activity, as well as pharmaceutical compositions and kits comprising the same. Such modulators may in certain embodiments interact with a druggable region of the invention. In still another aspect, the present invention is directed toward a modulator that is a fragment of (or homolog of such fragment or mimetic of such fragment) the druggable region of a dengue virus E protein or other viral class II E protein and competes with that druggable region. Modulators of any of the above-described druggable regions may be used alone or in complementary approaches to treat dengue viral or other viral infections.

In certain embodiments, a modulator interacts with the k1 hairpin so as to preclude it from moving, thereby modulating the activity of the dengue virus E protein or other flavivirus E protein. In another aspect, the present invention is directed towards a modulator that interacts with the stem region or the channel so as to preclude them from interacting, thereby modulating the activity of the dengue virus E protein or other flavivirus E protein. Such modulators may be, as described above, derived from either the stem region or the channel, and compete with the stem region or channel for binding. In still other embodiments, a modulator of class II E protein activity interacts with the domain I-III region. The modulator may also preclude the movement of the domain region. In another aspect, the present invention is directed towards a modulator that interacts with the fusion loop so as to preclude it from moving, thereby modulating the activity of the dengue virus E protein or other E protein.

Further, the present invention is in part directed toward an inhibitor that comprises SEQ ID NO: 3 or SEQ ID NO: 4, as well as fragments, homologs, variants, orthologs, and peptidomimetics thereof. Further, the present invention is directed towards an inhibitor that interacts with the relevant surfaces on the clustered domains II, so that completion of the conformational change is inhibited and thereby inhibiting the activity of the dengue virus E protein or other E protein. The present invention is also directed towards an inhibitor that interacts with the pocket beneath the k1 hairpin to interfere with the first stage of the conformational change, thereby modulating the activity of the dengue virus E protein or other E protein. Such inhibitors may be used in complementary approaches to treat dengue viral or other viral infections.

The embodiments and practices of the present invention, other embodiments, and their features and characteristics, will be apparent from the description, figures and claims that follow, with all of the claims hereby being incorporated by this reference into this Summary.

BRIEF DESCRIPTION OF THE FIGURES

FIG. 1A depicts the domain definition of dengue E. Domain I is red, domain II is yellow, and domain III is blue. FIG. 1B depicts the dengue E protein dimer, colored as in FIG. 1A, in complex with n-octyl-β-D-glucoside (β-OG). The β-OG, shown in green, is bound in a hydrophobic pocket under the k1 hairpin. The glycans in domains I and II are shown in ball-and-stick representation in red and yellow, respectively. Disulfide bridges are shown in orange. FIG. 1C depicts an enlarged view of the k1 hairpin region, with the structure of dengue E in the absence of β-OG (in translucent rendering) superimposed. The β-OG molecule, shown in space-filling representation, occupies the ligand-binding pocket. FIG. 1D depicts a superposition of the structures of dengue E and TBE E, both in the absence of β-OG. Dengue E is colored as in FIG. 1C, and TBE E is in grey. The view is the same as in FIG. 1C. FIGS. 1 and 2 were generated with BobScript (Esnouf, 1997; Kraulis, 1991) and Raster 3D (Merritt and Bacon, 1997).

FIG. 2 depicts the glycan at residue 153 in dengue 2 virus E protein. FIG. 2A depicts the E protein dimer, viewed perpendicular to the dyad axis (and the view in FIG. 1A. Both glycans are approximately perpendicular to the viral surface. Domain I and the attached glycan are shown in red, domain II and the attached glycan are shown in yellow, and domain III is in blue. Disulfide bridges are shown in orange. The molecule of n-octyl-β-D-glucoside bound in the hydrophobic pocket underneath the k1 hairpin is in green. FIG. 2B depicts an enlargement of the area surrounding the glycan at residue 153 in domain I, with the structure of TBE envelope protein superimposed (gray) onto domain I of dengue virus E protein. The fusion peptide is highlighted in orange. The disulfide bridge between residues 92 and 105 is shown in green.

FIG. 4A depicts the suggested transition from the previously studied T=1 subviral particles (Ferlenghi et al., 2001) to the fusion competent T=1 particle at low pH. Upon acidification, domain II is proposed to swing out about a hinge at the domain I/II interface, creating homotrimeric contacts at the threefold axis. Clusters of three fusion peptides are displayed at the tip of each trimer. FIG. 4B depicts the packing in T=3 virus-like particles deduced from image reconstructions of dengue virions (Kuhn et al., 2002). The 180 subunits are not related by local threefold symmetry. FIG. 4C depicts the suggested packing intermediate for the T=3 particle at low pH. E is shown in its native (high pH) conformation. Since all monomers are related by local threefold symmetry, the low-pH conformational change, will result in the formation of trimers, as in FIG. 4A.

FIG. 5A depicts the three domains of dengue sE. Domain I is red, domain II is yellow, and domain III is blue. A 53-residue "stem" segment links the stably folded sE fragment with the C-terminal transmembrane anchor. FIG. 5B depicts the sE dimer 7. This is the conformation of E in the mature virus particle and in solution above the fusion pH. FIG. 5C depicts the packing of E on the surface of the virus. Electron cryomicroscopy image reconstructions show that E dimers pack in a non-equivalent T=3 icosahedral lattice 10. Note the absence of local threefold symmetry for most dimers.

FIG. 6A depicts an electron micrograph showing E trimers inserted into liposomes. The liposomes are heavily decorated with E trimers. A large portion of the trimer can be seen protruding from the membrane. The samples were stained with uranyl formate (see Example 2). Scale bar=500 Å. FIG. 6B depicts the results of gel electrophoresis indicating that E trimers can be covalently cross-linked with ethylene glycol bis-succinimidyl-succinate (EGS) after insertion into liposomes. Lane 1: E solubilized from liposomes at pH 5.5 and not cross-linked. Lane 2: E solubilized from liposomes at pH 5.5 and cross-linked with EGS. Lane 3: E cross-linked with EGS at pH 7 in the absence of lipid.

FIG. 7A depicts an sE monomer in its pre-fusion conformation. This is the structure adopted in mature virus particles and in solution at pH>7—conditions under which E is a dimer. FIG. 7B depicts a schematic representation of the secondary structure of domain I and links to domains II and III in the pre-fusion conformation. FIG. 7C depicts an sE monomer in its post-fusion conformation, as seen in sE trimers. The three domains have rotated and shifted with respect to each other, bringing the C-terminus 39 Å closer to the fusion loop (orange). The fusion loop retains essentially the same conformation before and after fusion. FIG. 7D depicts the secondary structure of domain I and its links to domains II and III in the trimeric, post-fusion conformation. The domain I-III linker inserts between strands A0 and C0. The C-terminal region of A0 flips out, switches to the other b-sheet, and creates an annular trimer contact with the two other A0 strands in the trimer.

FIG. 8A depicts a ribbon diagram with domain I in red, domain II in yellow, and domain III in blue. Hydrophobic side chains in the fusion loop (orange) are exposed. The expected position of the hydrocarbon layer of the fused membrane is shown in green. Representative lipids are shown to scale. The trimer only penetrates about 6 Å into the hydrocarbon layer of the membrane. A chloride ion (black sphere) binds near the fusion loop. FIG. 8B depicts a surface representation of the trimer. The C-terminus of sE is located 60 Å from the membrane. The crystallized sE fragment ends 53 residues short of the viral transmembrane domain. This 53-residue "stem" could easily reach the membrane. The dashed grey arrow indicates the most likely location for the stem (see Example 2). An extended cavity is visible near the tip of the trimer; access to this cavity will probably be occluded by the stem. The glycan on Asn67 and representative lipids are shown in space-filling representation. FIG. 8C depicts the membrane-distal end of the trimer, where most trimer contacts are formed. The view is along the threefold axis. FIG. 8D depicts a close-up of c showing trimer contacts. The A0B0 loop forms an annular trimer contact. The domain I-III linker (purple) adopts an extended conformation and forms additional trimer contacts. FIG. 8E depicts a close-up of the aromatic anchor formed by the three fusion loops (orange). Three strictly conserved hydrophobic residues interact with the membrane: Trp101, Leu107 and Phe108. The three clustered fusion loops form a nonpolar, bowl-shaped apex, which is underpinned by a small hydrophobic core. Underneath, a chloride ion (black sphere) forms a trimer contact.

FIG. 9 depicts a proposed mechanism for fusion mediated by class II viral fusion proteins. Full-length E is represented as in FIG. 5C, with the stem and viral transmembrane domains in dark blue. FIG. 9A E binds to a receptor on the cell surface and the virion is internalized to an endosome. FIG. 9B Reduced pH in the endosome causes domain II to hinge outward from the virion surface, thus destroying dimer contacts and exposing the fusion loop. E monomers are free to rearrange laterally in the plane of the viral membrane. FIG. 9C The fusion loop inserts into the hydrocarbon layer of the host-cell membrane, promoting trimer formation. FIG. 9D The formation of trimer contacts spreads from the fusion loop at the tip of the trimer, to the base of the trimer. Domain III shifts and rotates to create trimer contacts, causing the C-terminal portion of E to fold back towards the fusion loop. The energy released by this refolding bends the opposed membranes. FIG. 9E Thermal motions in the lipid bilayer lead to the spontaneous fusion first of the cis monolayers ("hemifusion"), and then of the trans monolayers to form a lipidic fusion pore. This process is facilitated by the creation of additional trimer contacts, between the stem and domain II.

FIG. 10 depicts fluorescence depolarization binding data for a peptide corresponding to residues 396-429 (in the "stem" region) of dengue envelope protein (E). FIG. 10A depicts a Kd analysis of the peptide's binding affinity to the trimeric, post-fusion form of E. FIG. 10B depicts a competitive binding analysis with the fluorescent and unlabeled peptide.

FIG. 11 depicts a fluorescence depolarization Kd analysis to measure the affinity between a peptide corresponding to residues 413-447 (in the "stem" region) of dengue envelope protein (E). and the trimeric, post-fusion form of E.

DETAILED DESCRIPTION OF THE INVENTION

A. General

We have determined the structures of the E protein in both its pre-fusion and post-fusion conformations.

The pre-fusion structure was determined by solving the structure of a soluble fragment (residues 1-394) of the E protein from dengue virus type 2. This fragment contains all but about 45 residues of the E-protein ectodomain (FIG. 1A). It resembles closely, in its dimeric structure and in the details of its protein fold, the E protein from tick-borne encephalitis (TBE) virus, studied previously. We have examined crystals grown in both the presence and the absence of the detergent n-octyl-β-D-glucoside, β-OG. The key difference between the two structures is a local rearrangement of the "k1" β-hairpin (residues 268-280) and the concomitant opening up of a hydrophobic pocket, occupied by a molecule of β-OG. Mutations affecting the pH threshold for fusion map to the hydrophobic pocket, which we propose is a hinge point in the fusion-activating conformational change. Detergent binding marks the k1 β-hairpin and associated pocket as a potential target for viral fusion inhibitors. We have also discovered another region, the domain 1-3 region, which may serve as a target for viral fusion inhibitors.

The post-fusion structure of the soluble E ectodomain (sE) in its trimeric, post-fusion state reveals striking differences from the dimeric, pre-fusion form. The elongated trimer bears three "fusion loops" at one end, to insert into the host-cell membrane. Their structure allows us to model directly how they interact with a lipid bilayer. The protein folds back on itself, directing its C-terminus towards the fusion loop. We propose a fusion mechanism driven by essentially irreversible conformational changes in dengue virus E protein and facilitated by fusion-loop insertion into the outer bilayer leaflet. Specific features of the folded-back structure suggest strategies for inhibiting flavivirus entry, as well as druggable regions. The regions may serve as a target for viral fusion inhibitors and assays to discover such inhibitors.

Hence, we have discovered a variety of novel, structurally defined druggable regions which may present targets for a specific viral fusion inhibitor for dengue virus and other viruses having class II E protein. Because dengue virus type 2 E protein is strongly homologous to other dengue viral types, as well as other flavivirus E proteins and class II E proteins (Lindenbach and Rice, 2001, Rey, et al. 1995, Hahn, et al. 1998), these binding sites are likely present in those E proteins as well and may serve as targets for specific viral fusion inhibitors for those viruses.

Finally, we have also discovered that peptides corresponding to residues 396-429 and 413-447 (in the "stem" region) of dengue envelope protein (E) binds with fairly high affinity and specificity to the trimeric, post-fusion form of sE, the fragment of E spanning residues 1-395, which we crystallized first in the pre-fusion form and then in the post-fusion form. Inhibitor peptides derived from stem sequences may block completion of the conformational change by interacting with the relevant surfaces on the clustered domains II. Such inhibitors would interfere with the second stage of the conformational change. This peptide itself may serve as a specific viral fusion inhibitor, or may provide the basis from which to design improved specific viral fusion inhibitors.

B. Definitions

Figure 1:
FIG. 1 depicts various views of dengue E protein and its ligand-binding pocket.

For convenience, before further description of the present invention, certain terms employed in the specification, examples, and appendant claims are collected here. These definitions should be read in light of the entire disclosure and understood as by a person of skill in the art.

The articles "a" and "an" are used herein to refer to one or to more than one (i.e., to at least one) of the grammatical object of the article. By way of example, "an element" means one element or more than one element.

The term "activity" of a class II E protein refers to the ability of the protein to mediate both receptor binding and fusion between a virus and a cell.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing.

The term "binding" refers to an association, which may be a stable association, between two molecules, e.g., between a dengue virus E protein or another class II E protein and a binding partner, due to, for example, electrostatic, hydrophobic, ionic and/or hydrogen-bond interactions under physiological conditions.

The term "complex" refers to an association between at least two moieties (e.g. chemical or biochemical) that have an affinity for one another. Examples of complexes include associations between antigen/antibodies, lectin/carbohydrate, target polynucleotide/probe oligonucleotide, antibody/anti-antibody, receptor/ligand, enzyme/ligand, polypeptide/polypeptide, polypeptide/polynucleotide, polypeptide/cofactor, polypeptide/substrate, polypeptide/modulator, polypeptide/small molecule, and the like. "Member of a complex" refers to one moiety of the complex, such as an antigen or ligand. "Protein complex" or "polypeptide complex" refers to a complex comprising at least one polypeptide.

The term "compound" as used herein refers to any agent, molecule, complex, or other entity that may be capable of binding to or interacting with a protein.

The term "conserved residue" refers to an amino acid that is a member of a group of amino acids having certain common properties. The term "conservative amino acid substitution" refers to the substitution (conceptually or otherwise) of an amino acid from one such group with a different amino acid from the same group. A functional way to define common properties between individual amino acids is to analyze the normalized frequencies of amino acid changes between corresponding proteins of homologous organisms (Schulz, G. E. and R. H. Schirmer., Principles of Protein Structure, Springer-Verlag). According to such analyses, groups of amino acids may be defined where amino acids within a group exchange preferentially with each other, and therefore resemble each other most in their impact on the overall protein structure (Schulz, G. E. and R. H. Schirmer, Principles of Protein Structure, Springer-Verlag). One example of a set of amino acid groups defined in this manner include: (i) a charged group, consisting of Glu and Asp, Lys, Arg and His, (ii) a positively-charged group, consisting of Lys, Arg and His, (iii) a negatively-charged group, consisting of Glu and Asp, (iv) an aromatic group, consisting of Phe, Tyr and Trp, (v) a nitrogen ring group, consisting of His and Trp, (vi) a large aliphatic nonpolar group, consisting of Val, Leu and Ile, (vii) a slightly-polar group, consisting of Met and Cys, (viii) a small-residue group, consisting of Ser, Thr, Asp, Asn, Gly, Ala, Glu, Gln and Pro, (ix) an aliphatic group consisting of Val, Leu, Ile, Met and Cys, and (x) a small hydroxyl group consisting of Ser and Thr.

The term "disease caused by a flavivirus or other virus having class II E protein" refers to any disorder or disease caused by infection of a subject with a flavivirus or other virus having class II E protein. Exemplary diseases caused by a flavivirus or other virus having class II E protein include, but are not limited to, dengue fever, dengue hemorrhagic fever, tick-borne encephalitis, West Nile virus disease, yellow fever, Kyasanur Forest disease, louping ill, hepatitis C, Ross River virus disease, and O'nyong fever.

The term "domain", when used in connection with a polypeptide, refers to a specific region within such polypeptide that comprises a particular structure or mediates a particular function. In the typical case, a domain of a dengue virus E protein or other class II E protein is a fragment of the polypeptide. In certain instances, a domain is a structurally stable domain, as evidenced, for example, by mass spectroscopy, or by the fact that a modulator may bind to a druggable region of the domain.

The term "domain region" as used herein refers to any structural motif having homology to the motif comprising at least one of residues 38-40; 143-147; 294-296; and 354-365 of a dengue virus E protein.

The term "domain II" as used herein refers to any structural motif having homology to the motif comprising at least one of residues 52-132 and 193-280 of a dengue virus E protein.

The term "druggable region", when used in reference to a polypeptide, nucleic acid, complex and the like, refers to a region of a dengue virus E protein or other class II E protein which is a target or is a likely target for binding an agent that reduces or inhibits viral infectivity. For a polypeptide, a druggable region generally refers to a region wherein several amino acids of a polypeptide would be capable of interacting with an agent. For a polypeptide or complex thereof, exemplary druggable regions including binding pockets and sites, interfaces between domains of a polypeptide or complex, surface grooves or contours or surfaces of a polypeptide or complex which are capable of participating in interactions with another molecule, such as a cell membrane. In particular, a subject druggable region is the k1 hairpin region and its associated detergent binding pocket. In yet another example, a subject druggable region is the domain 1-3 region comprising at least one of residues 38-40; 143-147; 294-296; and 354-365 of a dengue virus E protein or the homologous residues in other class II E protein.

A druggable region may be described and characterized in a number of ways. For example, a druggable region may be characterized by some or all of the amino acids that make up the region, or the backbone atoms thereof, or the side chain atoms thereof (optionally with or without the Ca atoms). Alternatively, a druggable region may be characterized by comparison to other regions on the same or other molecules. For example, the term "affinity region" refers to a druggable region on a molecule (such as a dengue virus E protein or other class II E protein) that is present in several other molecules, in so much as the structures of the same affinity regions are sufficiently the same so that they are expected to bind the same or related structural analogs. An example of an affinity region is an ATP-binding site of a protein kinase that is found in several protein kinases (whether or not of the same origin). The term "selectivity-region" refers to a druggable region of a molecule that may not be found on other molecules, in so much as the structures of different selectivity regions are sufficiently different so that they are not expected to bind the same or related structural analogs. An exemplary selectivity region is a catalytic domain of a protein kinase that exhibits specificity for one substrate. In certain instances, a single modulator may bind to the same affinity region across a number of proteins that have a substantially similar biological function, whereas the same modulator may bind to only one selectivity region of one of those proteins.

Continuing with examples of different druggable regions, the term "undesired region" refers to a druggable region of a molecule that upon interacting with another molecule results in an undesirable affect. For example, a binding site that oxidizes the interacting molecule (such as P-450 activity) and thereby results in increased toxicity for the oxidized molecule may be deemed a "undesired region". Other examples of potential undesired regions includes regions that upon interaction with a drug decrease the membrane permeability of the drug, increase the excretion of the drug, or increase the blood brain transport of the drug. It may be the case that, in certain circumstances, an undesired region will no longer be deemed an undesired region because the affect of the region will be favorable, e.g., a drug intended to treat a brain condition would benefit from interacting with a region that resulted in increased blood brain transport, whereas the same region could be deemed undesirable for drugs that were not intended to be delivered to the brain.

When used in reference to a druggable region, the "selectivity" or "specificity" of a molecule such as a modulator to a druggable region may be used to describe the binding between the molecule and a druggable region. For example, the selectivity of a modulator with respect to a druggable region may be expressed by comparison to another modulator, using the respective values of Kd (i.e., the dissociation constants for each modulator-druggable region complex) or, in cases where a biological effect is observed below the Kd, the ratio of the respective EC50's (i.e., the concentrations that produce 50% of the maximum response for the modulator interacting with each druggable region).

The term "class II E protein" refers to any protein (full-length or fragment) having the sequence of a major class II virus envelope glycoprotein, E, derived from a flavivirus, alphavirus, or hepatitis virus. The term "dengue virus E protein" refers to a major virus envelope glycoprotein, E, derived from a dengue fever virus of any type. The full-length 495-residue sequence of dengue virus E protein from dengue virus type 2 is SEQ ID NO: 1: MRCIGISNRDFVEG-VSGGSWVDIVLEHGSCVTTMAKNKPTLD-FELIKTEAKQPATL RKYCIEAKLTNTTTD-SRCPTQGEPTLNEEQDKRFVCKHSMVDRGWGNGC-GLFGKG GIVTCAMFTCKKNMEGKIVQPENLEYTV-VITPHSGEEHAVGNDTGKHGKEVKITPQ SSITEAELT-GYGTVTMECSPRTGLDFNEMVLLQMKD-KAWLVHRQWFLDLPLPWLP GADTQGSNWIQKETLVTFKNPHAKKQDV-VVLGSQEGAMHTALTGATEIQMSSGN LLFT-GHLKCRLRMDKLQLKGMSYSMCTGKFKV-VKEIAETQHGTIVIRVQYEGDGS PCKTPFEIMDLEKRHVLGRLTTVNPIV-TEKDSPVNIEAEPPFGDSYIIIGVEPGQLKLD WFKKGSSIGQMFETTMRGAKRMAILGD-TAWDFGSLGGVFTSIGKALHQVFGAIYG AAFS-GVSWTMKILIGVIITWIGMNSRSTSLS-VSLVLVGIVTLYLGVMVQA. The term "dengue virus E protein" encompasses sequences with at least 85% identity to this sequence, such as, for example an E protein from dengue virus type 1, and also encompasses fragments of the full-length E protein. For example, the truncated dengue virus E protein used herein is SEQ ID NO: 2: and consists of residues 1-394 of full-length dengue virus type 2 E protein: MRCIGISNRDFVEGVSGGSWVDIVLEHG-SCVTTMAKNKPTLDFELIKTEAKQPATL RKYCIEAK-LTNTTTDSRCPTQGEPTLNEEQD-KRFVCKHSMVDRGWGNGCGLFGKG GIVTCAMFTCKKNMEGKIVQPENLEYTV-VITPHSGEEHAVGNDTGKHGKEVKITPQ SSITEAELT-GYGTVTMECSPRTGLDFNEMVLLQMKD-KAWLVHRQWFLDLPLPWLP GADTQGSNWIQKETLVTFKNPHAKKQDV-VVLGSQEGAMHTALTGATEIQMSSGN LLFT-GHLKCRLRMDKLQLKGMSYSMCTGKFKV-VKEIAETQHGTIVIRVQYEGDGS PCKTPFEIMDLEKRHVLGRLTTVNPIV-TEKDSPVNIEAEPPFGDSYIIIGVEPGQLKLD WFKK. Other fragments may be shorter or longer. Such E proteins and protein fragments may be produced by any method known in the art, including purification from natural sources, recombinant methods, and peptide synthesis. Such proteins may be produced in a soluble form (referred to herein as "sE", e.g. lacking transmembrane regions, or solubilized using appropriate reagents (such as a detergent).

The term "gene" refers to a nucleic acid comprising an open reading frame encoding a polypeptide having exon sequences and optionally intron sequences. The term "intron" refers to a DNA sequence present in a given gene which is not translated into protein and is generally found between exons.

The term "having substantially similar biological activity", when used in reference to two polypeptides, refers to a biological activity of a first polypeptide which is substantially similar to at least one of the biological activities of a second polypeptide. A substantially similar biological activity means that the polypeptides carry out a similar function, e.g., a similar enzymatic reaction or a similar physiological process, etc. For example, two homologous proteins may have a substantially similar biological activity if they are involved in a similar enzymatic reaction, e.g., they are both kinases which catalyze phosphorylation of a substrate polypeptide, however, they may phosphoryl different regions on the same protein substrate or different substrate proteins altogether. Alternatively, two homologous proteins may also have a substantially similar biological activity if they are both involved in a similar physiological process, e.g., transcription. For example, two proteins may be transcription factors, however, they may bind to different DNA sequences or bind to different polypeptide interactors. Substantially similar biological activities may also be associated with proteins carrying out a similar structural role, for example, two membrane proteins.

The term "isolated polypeptide" refers to a polypeptide, in certain embodiments prepared from recombinant DNA or RNA, or of synthetic origin, or some combination thereof, which (1) is not associated with proteins that it is normally found with in nature, (2) is isolated from the cell in which it occurs, (3) is isolated free of other proteins from the same cellular source, (4) is expressed by a cell from a different species, or (5) does not occur in nature.

The term "isolated nucleic acid" refers to a polynucleotide of genomic, cDNA, or synthetic origin or some combination there of, which (1) is not associated with the cell in which the "isolated nucleic acid" is found in nature, or (2) is operably linked to a polynucleotide to which it is not linked in nature.

The term "k1 hairpin", or "E protein k1 h", as used herein refers to any structural motif having homology to the motif comprising at least residues 268-280, and in some embodiments further comprising at least one of residues 47-54, 128-137, and 187-207.

The term "mammal" is known in the art, and exemplary mammals include humans, primates, bovines, porcines, canines, felines, and rodents (e.g., mice and rats).

The term "modulation", when used in reference to a functional property or biological activity or process (e.g., enzyme activity or receptor binding), refers to the capacity to either up regulate (e.g., activate or stimulate), down regulate (e.g., inhibit or suppress) or otherwise change a quality of such property, activity or process. In certain instances, such regulation may be contingent on the occurrence of a specific event, such as activation of a signal transduction pathway, and/or may be manifest only in particular cell types.

The term "modulator" refers to a polypeptide, nucleic acid, macromolecule, complex, molecule, small molecule, compound, species or the like (naturally-occurring or non-naturally-occurring), or an extract made from biological materials such as bacteria, plants, fungi, or animal cells or tissues, that may be capable of causing modulation. Modulators may be evaluated for potential activity as modulators or activators (directly or indirectly) of a functional property, biological activity or process, or combination of them, (e.g., agonist, partial antagonist, partial agonist, inverse agonist, antagonist, anti-microbial agents, modulators of microbial infection or proliferation, and the like) by inclusion in assays. In such assays, many modulators may be screened at one time. The activity of a modulator may be known, unknown or partially known. The term "inhibitor" refers to a polypeptide, nucleic acid, macromolecule, complex, molecule, small molecule, compound, species or the like (naturally-occurring or non-naturally-occurring), or an extract made from biological materials such as bacteria, plants, fungi, or animal cells or tissues, that may be capable of down-regulating or suppressing a functional property or biological activity or process.

The term "motif" refers to an amino acid sequence that is commonly found in a protein of a particular structure or function. Typically, a consensus sequence is defined to represent a particular motif. The consensus sequence need not be strictly defined and may contain positions of variability, degeneracy, variability of length, etc. The consensus sequence may be used to search a database to identify other proteins that may have a similar structure or function due to the presence of the motif in its amino acid sequence. For example, on-line databases may be searched with a consensus sequence in order to identify other proteins containing a particular motif. Various search algorithms and/or programs may be used, including FASTA, BLAST or ENTREZ. FASTA and BLAST are available as a part of the GCG sequence analysis package (University of Wisconsin, Madison, Wis.). ENTREZ is available through the National Center for Biotechnology Information, National Library of Medicine, National Institutes of Health, Bethesda, Md.

The term "nucleic acid" refers to a polymeric form of nucleotides, either ribonucleotides or deoxynucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

The term "polypeptide", and the terms "protein" and "peptide" which are used interchangeably herein, refers to a polymer of amino acids. Exemplary polypeptides include gene products, naturally-occurring proteins, homologs, orthologs, paralogs, fragments, and other equivalents, variants and analogs of the foregoing.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions may occur at the amino-terminus or carboxy-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. A fragment can retain one or more of the biological activities of the reference polypeptide. In certain embodiments, a fragment may comprise a druggable region, and optionally additional amino acids on one or both sides of the druggable region, which additional amino acids may number from 5, 10, 15, 20, 30, 40, 50, or up to 100 or more residues. Further, fragments can include a sub-fragment of a specific region, which sub-fragment retains a function of the region from which it is derived. In another embodiment, a fragment may have immunogenic properties.

The term "purified" refers to an object species that is the predominant species present (i.e., on a molar basis it is more abundant than any other individual species in the composition). A "purified fraction" is a composition wherein the object species comprises at least about 50 percent (on a molar basis) of all species present. In making the determination of the purity of a species in solution or dispersion, the solvent or matrix in which the species is dissolved or dispersed is usually not included in such determination; instead, only the species (including the one of interest) dissolved or dispersed are taken into account. Generally, a purified composition will have one species that comprises more than about 80 percent of all species present in the composition, more than about 85%, 90%, 95%, 99% or more of all species present. The object species may be purified to essential homogeneity (contaminant species cannot be detected in the composition by conventional detection methods) wherein the composition consists essentially of a single species. A skilled artisan may purify a dengue virus E protein or other class II E protein using standard techniques for protein purification in light of the teachings herein. Purity of a polypeptide may be determined by a number of methods known to those of skill in the art, including for example, amino-terminal amino acid sequence analysis, gel electrophoresis, mass-spectrometry analysis and the methods described in the Exemplification section herein.

The terms "recombinant protein" or "recombinant polypeptide" refer to a polypeptide which is produced by recombinant DNA techniques. An example of such techniques includes the case when DNA encoding the expressed protein is inserted into a suitable expression vector which is in turn used to transform a host cell to produce the protein or polypeptide encoded by the DNA.

The term "small molecule" refers to a compound, which has a molecular weight of less than about 5 kD, less than about 2.5 kD, less than about 1.5 kD, or less than about 0.9 kD. Small molecules may be, for example, nucleic acids, peptides, polypeptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention. The term "small organic molecule" refers to a small molecule that is often identified as being an organic or medicinal compound, and does not include molecules that are exclusively nucleic acids, peptides or polypeptides.

The term "soluble" as used herein with reference to a dengue virus E protein or other class II E protein or other protein, means that upon expression in cell culture, at least some portion of the polypeptide or protein expressed remains in the cytoplasmic fraction of the cell and does not fractionate with the cellular debris upon lysis and centrifugation of the lysate. Solubility of a polypeptide may be increased by a variety of art recognized methods, including fusion to a heterologous amino acid sequence, deletion of amino acid residues, amino acid substitution (e.g., enriching the sequence with amino acid residues having hydrophilic side chains), and chemical modification (e.g., addition of hydrophilic groups). The solubility of polypeptides may be measured using a variety of art recognized techniques, including, dynamic light scattering to determine aggregation state, UV absorption, centrifugation to separate aggregated from non-aggregated material, and SDS gel electrophoresis (e.g., the amount of protein in the soluble fraction is compared to the amount of protein in the soluble and insoluble fractions combined). When expressed in a host cell, the polypeptides of the invention may be at least about 1%, 2%, 5%, 10%, 20%, 30%, 40%, 50%, 60%, 70%, 80%, 90% or more soluble, e.g., at least about 1%, 2%, 5%, 10%, 20%, 30%, 40%, 50%, 60%, 70%, 80%, 90% or more of the total amount of protein expressed in the cell is found in the cytoplasmic fraction. In certain embodiments, a one liter culture of cells expressing a dengue virus E protein or other class II E protein will produce at least about 0.1, 0.2, 0.5, 1, 2, 5, 10, 20, 30, 40, 50 milligrams or more of soluble protein. In an exemplary embodiment, a dengue virus E protein or other class II E protein is at least about 10% soluble and will produce at least about 1 milligram of protein from a one liter cell culture.

The term "structural motif", when used in reference to a polypeptide, refers to a polypeptide that, although it may have different amino acid sequences, may result in a similar structure, wherein by structure is meant that the motif forms generally the same tertiary structure, or that certain amino acid residues within the motif, or alternatively their backbone or side chains (which may or may not include the Cα atoms of the side chains) are positioned in a like relationship with respect to one another in the motif.

The term "test compound" refers to a molecule to be tested by one or more screening method(s) as a putative modulator of a dengue virus E protein or other class II E protein or other biological entity or process. A test compound is usually not known to bind to a target of interest. The term "control test compound" refers to a compound known to bind to the target (e.g., a known agonist, antagonist, partial agonist or inverse agonist). The term "test compound" does not include a chemical added as a control condition that alters the function of the target to determine signal specificity in an assay. Such control chemicals or conditions include chemicals that 1) nonspecifically or substantially disrupt protein structure (e.g., denaturing agents (e.g., urea or guanidinium), chaotropic agents, sulfhydryl reagents (e.g., dithiothreitol and b-mercaptoethanol), and proteases), 2) generally inhibit cell metabolism (e.g., mitochondrial uncouplers) and 3) non-specifically disrupt electrostatic or hydrophobic interactions of a protein (e.g., high salt concentrations, or detergents at concentrations sufficient to non-specifically disrupt hydrophobic interactions). Further, the term "test compound" also does not include compounds known to be unsuitable for a therapeutic use for a particular indication due to toxicity of the subject. In certain embodiments, various predetermined concentrations of test compounds are used for screening such as 0.01 mM, 0.1 mM, 1.0 mM, and 10.0 mM. Examples of test compounds include, but are not limited to, peptides, nucleic acids, carbohydrates, and small molecules. The term "novel test compound" refers to a test compound that is not in existence as of the filing date of this application. In certain assays using novel test compounds, the novel test compounds comprise at least about 50%, 75%, 85%, 90%, 95% or more of the test compounds used in the assay or in any particular trial of the assay.

The term "therapeutically effective amount" refers to that amount of a modulator, drug or other molecule which is sufficient to effect treatment when administered to a subject in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "transfection" means the introduction of a nucleic acid, e.g., an expression vector, into a recipient cell, which in certain instances involves nucleic acid-mediated gene transfer. The term "transformation" refers to a process in which a cell's genotype is changed as a result of the cellular uptake of exogenous nucleic acid. For example, a transformed cell may express a recombinant form of a dengue virus E protein or other class II E protein, or antisense expression may occur from the transferred gene so that the expression of a naturally-occurring form of the gene is disrupted.

The term "transgene" means a nucleic acid sequence, which is partly or entirely heterologous to a transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene may include one or more regulatory sequences and any other nucleic acids, such as introns, that may be necessary for optimal expression.

The term "transgenic animal" refers to any animal, for example, a mouse, rat or other non-human mammal, a bird or an amphibian, in which one or more of the cells of the animal contain heterologous nucleic acid introduced by way of human intervention, such as by transgenic techniques well known in the art. The nucleic acid is introduced into the cell, directly or indirectly, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of a protein. However, transgenic animals in which the recombinant gene is silent are also contemplated.

The term "vector" refers to a nucleic acid capable of transporting another nucleic acid to which it has been linked. One type of vector which may be used in accord with the invention is an episome, i.e., a nucleic acid capable of extra-chromosomal replication. Other vectors include those capable of autonomous replication and expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA molecules which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

C. Drug Discovery

C.1. Druggable Regions

Based in part on the structural information described in the Exemplification, we have identified novel druggable regions in dengue virus E protein. In one embodiment, the druggable region is comprised of the k1 hairpin or a portion thereof. In certain embodiments, the k1 hairpin may be comprised of at least one of residues 268-280 of a dengue virus E protein or the homologous residues in other class II E protein. In other embodiments, the druggable region or active site region may be comprised of the k1 hairpin and at least one of residues 47-54, 128-137, and 187-207.

In yet another embodiment, the druggable region may comprise the regions involved in the binding of residues 396-429 (the "stem" region of dengue envelope protein E) binds to the trimeric, post-fusion form of dengue virus E protein or other flavivirus E protein. In one embodiment, the druggable region is comprised of the stem region or a portion thereof. The stem region comprises residues 396-447, or fragments thereof, for example 396-429 and 413-447. In another embodiment, the druggable region is comprised of the channel in which the stem region binds. The channel is comprised of the residues at the trimer interface formed by domain II of each subunit in the trimer. Domain II consists of residues 52-132 and 193-280. A second region is the channel where the stem binds, formed by residues in domain II.

In another embodiment, the druggable region is comprised of the domain region. In certain embodiments, the domain I-III region may be comprised of at least one of residues 38-40; 143-147; 294-296; and 354-365 of a dengue virus E protein or the homologous residues in other class II E protein. In other embodiments, the druggable region may be comprised of the domain I-domain III linker (residues 294-301).

In yet another embodiment, a druggable region is comprised of the fusion loop or a portion thereof.

Other regions of protein may in certain embodiments comprise a druggable region. For example, the hydrophobic core beneath the k1 hairpin or a portion thereof may comprise a druggable region. In another example, a druggable region may comprise domain II or a portion thereof. In still another example, a druggable region may comprise domain III or a portion thereof. In other examples, the pH-dependent hinge may serve as a druggable region. Further, a region or portion of a region of the E protein involved in trimerization, such as for example, the regions of domain II involved in trimerization, may present a druggable region. A region or a portion of a region involved in the stem fold back conformational change may comprise a druggable region, for example, such regions as the stem-domain II contact regions, the trimeric N terminal inner core, and C terminal outer layer surfaces on the clustered domains II, as well as the 53-residue stem. In certain embodiments, a druggable region may consist of the entire fragment of the E protein spanning residues 1-395.

In yet another aspect, the present invention is directed toward methods of identifying and designing modulators which bind with, interact with, or modulate the function or activity of an active or binding site of a dengue virus E protein or other class II E protein.

C.2. Modulators, Modulator Design and Screening Using the Subject Druggable Regions In one aspect, the present invention provides methods of screening the subject druggable regions for potential modulators, as well as methods of designing such modulators. Modulators to polypeptides of the invention and other structurally related molecules, and complexes containing the same, may be identified and developed as set forth below and otherwise using techniques and methods known to those of skill in the art. The modulators of the invention may be employed, for instance, to inhibit and treat disease caused by a flavivirus or other virus having class II E protein, such as dengue fever, dengue hemorrhagic fever, tick-borne encephalitis, West Nile virus disease, yellow fever, Kyasanur Forest disease, louping ill, hepatitis C, Ross River virus disease, and O'nyong fever.

In one aspect, the present invention is directed towards a modulator that interacts with the subject druggable regions so as to reduce the activity of the dengue virus E protein or other class II E protein. Such modulators may in certain embodiments interact with a druggable region of the invention. In still another aspect, the present invention is directed toward a modulator that is a fragment of (or homolog of such fragment or mimetic of such fragment) the druggable region of a dengue virus E protein or other viral class II E protein and competes with that druggable region. Modulators of any of the above-described druggable regions may be used alone or in complementary approaches to treat dengue viral or other viral infections.

In certain embodiments, a modulator interacts with the k1 hairpin so as to preclude it from moving, thereby modulating the activity of the dengue virus E protein or other flavivirus E protein. In another aspect, the present invention is directed towards a modulator that interacts with the stem region or the channel so as to preclude them from interacting, thereby modulating the activity of the dengue virus E protein or other flavivirus E protein. Such modulators may be, as described above, derived from either the stem region or the channel, and compete with the stem region or channel for binding. In still other embodiments, a modulator of class II E protein activity interacts with the domain I-III region. The modulator may also preclude the movement of the domain I-III region. In another aspect, the present invention is directed towards a modulator that interacts with the fusion loop so as to preclude it from moving, thereby modulating the activity of the dengue virus E protein or other E protein.

Further, the present invention is in part directed toward an inhibitor that comprises SEQ ID NO: 3 or SEQ ID NO: 4, as well as fragments, homologs, variants, orthologs, and peptidomimetics thereof. Further, the present invention is directed towards an inhibitor that interacts with the relevant surfaces on the clustered domains II, so that completion of the conformational change is inhibited and thereby inhibiting the activity of the dengue virus E protein or other E protein. The present invention is also directed towards an inhibitor that interacts with the pocket beneath the k1 hairpin to interfere with the first stage of the conformational change, thereby modulating the activity of the dengue virus E protein or other E protein. Such inhibitors may be used in complementary approaches to treat dengue viral or other viral infections.

A variety of methods for inhibiting the growth or infectivity of flaviviruses using the modulators are contemplated by the present invention. For example, exemplary methods involve contacting a flavivirus with a modulator thought or shown to be effective against such pathogen.

For example, in one aspect, the present invention contemplates a method for treating a patient suffering from an infection of dengue fever or other flavivirus comprising administering to the patient an amount of a modulator effective to modulate the expression and/or activity of a dengue virus E protein or other class II E protein. In certain instances, the animal is a human or a livestock animal such as a cow, pig, goat or sheep. The present invention further contemplates a method for treating a subject suffering from a flavivirus-related, alphavirus-related, or hepatitis-related disease or disorder, comprising administering to an animal having the condition a therapeutically effective amount of a molecule identified using one of the methods of the present invention.

In another embodiment, modulators of a dengue virus E protein or other class II E protein, or biological complexes containing them, may be used in the manufacture of a medicament for any number of uses, including, for example, treating any disease or other treatable condition of a patient (including humans and animals), and particularly a disease caused by a flavivirus or other virus having class II E protein, such as, for example, one of the following: dengue fever, dengue hemorrhagic fever, tick-borne encephalitis, West Nile virus disease, yellow fever, Kyasanur Forest disease, louping ill, hepatitis C, Ross River virus disease, and O'nyong fever.

(a) Modulator Design

A number of techniques can be used to screen, identify, select and design chemical entities capable of associating with a dengue virus E protein or other class II E protein, structurally homologous molecules, and other molecules. Knowledge of the structure for a dengue virus E protein or other class II E protein, determined in accordance with the methods described herein, permits the design and/or identification of molecules and/or other modulators which have a shape complementary to the conformation of a dengue virus E protein or other class II E protein, or more particularly, a druggable region thereof. It is understood that such techniques and methods may use, in addition to the exact structural coordinates and other information for a dengue virus E protein or other class II E protein, structural equivalents thereof described above (including, for example, those structural coordinates that are derived from the structural coordinates of amino acids contained in a druggable region as described above).

The term "chemical entity," as used herein, refers to chemical compounds, complexes of two or more chemical compounds, and fragments of such compounds or complexes. In certain instances, it is desirable to use chemical entities exhibiting a wide range of structural and functional diversity, such as compounds exhibiting different shapes (e.g., flat aromatic rings(s), puckered aliphatic rings(s), straight and branched chain aliphatics with single, double, or triple bonds) and diverse functional groups (e.g., carboxylic acids, esters, ethers, amines, aldehydes, ketones, and various heterocyclic rings).

In one aspect, the method of drug design generally includes computationally evaluating the potential of a selected chemical entity to associate with any of the molecules or complexes of the present invention (or portions thereof). For example, this method may include the steps of (a) employing computational means to perform a fitting operation between the selected chemical entity and a druggable region of the molecule or complex; and (b) analyzing the results of said fitting operation to quantify the association between the chemical entity and the druggable region.

A chemical entity may be examined either through visual inspection or through the use of computer modeling using a docking program such as GRAM, DOCK, or AUTODOCK (Dunbrack et al., Folding & Design, 2:27-42 (1997)). This procedure can include computer fitting of chemical entities to a target to ascertain how well the shape and the chemical structure of each chemical entity will complement or interfere with the structure of a dengue virus E protein or other class II E protein (Bugg et al., Scientific American, December: 92-98 (1993); West et al., TIPS, 16:67-74 (1995)). Computer programs may also be employed to estimate the attraction, repulsion, and steric hindrance of the chemical entity to a druggable region, for example. Generally, the tighter the fit (e.g., the lower the steric hindrance, and/or the greater the attractive force) the more potent the chemical entity will be because these properties are consistent with a tighter binding constant. Furthermore, the more specificity in the design of a chemical entity the more likely that the chemical entity will not interfere with related proteins, which may minimize potential side-effects due to unwanted interactions.

A variety of computational methods for molecular design, in which the steric and electronic properties of druggable regions are used to guide the design of chemical entities, are known: Cohen et al. (1990) J. Med. Cam. 33: 883-894; Kuntz et al. (1982) J. Mol. Biol. 161: 269-288; DesJarlais (1988) J. Med. Cam. 31: 722-729; Bartlett et al. (1989) Spec. Publ., Roy. Soc. Chem. 78: 182-196; Goodford et al. (1985) J. Med. Cam. 28: 849-857; and DesJarlais et al. J. Med. Cam. 29: 2149-2153. Directed methods generally fall into two categories: (1) design by analogy in which 3-D structures of known chemical entities (such as from a crystallographic database) are docked to the druggable region and scored for goodness-of-fit; and (2) de novo design, in which the chemical entity is constructed piece-wise in the druggable region. The chemical entity may be screened as part of a library or a database of molecules. Databases which may be used include ACD (Molecular Designs Limited), NCI (National Cancer Institute), CCDC (Cambridge Crystallographic Data Center), CAST (Chemical Abstract Service), Derwent (Derwent Information Limited), Maybridge (Maybridge Chemical Company Ltd), Aldrich (Aldrich Chemical Company), DOCK (University of California in San Francisco), and the Directory of Natural Products (Chapman & Hall). Computer programs such as CONCORD (Tripos Associates) or DB-Converter (Molecular Simulations Limited) can be used to convert a data set represented in two dimensions to one represented in three dimensions.

Chemical entities may be tested for their capacity to fit spatially with a druggable region or other portion of a target protein. As used herein, the term "fits spatially" means that the three-dimensional structure of the chemical entity is accommodated geometrically by a druggable region. A favorable geometric fit occurs when the surface area of the chemical entity is in close proximity with the surface area of the druggable region without forming unfavorable interactions. A favorable complementary interaction occurs where the chemical entity interacts by hydrophobic, aromatic, ionic, dipolar, or hydrogen donating and accepting forces. Unfavorable interactions may be steric hindrance between atoms in the chemical entity and atoms in the druggable region.

If a model of the present invention is a computer model, the chemical entities may be positioned in a druggable region through computational docking. If, on the other hand, the model of the present invention is a structural model, the chemical entities may be positioned in the druggable region by, for example, manual docking. As used herein the term "docking" refers to a process of placing a chemical entity in close proximity with a druggable region, or a process of finding low energy conformations of a chemical entity/druggable region complex.

In an illustrative embodiment, the design of potential modulator begins from the general perspective of shape complimentary for the druggable region of a dengue virus E protein or other class II E protein, and a search algorithm is employed which is capable of scanning a database of small molecules of known three-dimensional structure for chemical entities which fit geometrically with the target druggable region. Most algorithms of this type provide a method for finding a wide assortment of chemical entities that are complementary to the shape of a druggable region of a dengue virus E protein or other class II E protein. Each of a set of chemical entities from a particular data-base, such as the Cambridge Crystallographic Data Bank (CCDB) (Allen et al. (1973) *J. Chem. Doc.* 13: 119), is individually docked to the druggable region of a dengue virus E protein or other class II E protein in a number of geometrically permissible orientations with use of a docking algorithm. In certain embodiments, a set of computer algorithms called DOCK, can be used to characterize the shape of invaginations and grooves that form the active sites and recognition surfaces of the druggable region (Kuntz et al. (1982) *J. Mol. Biol.* 161: 269-288). The program can also search a database of small molecules for templates whose shapes are complementary to particular binding sites of a dengue virus E protein or other class II E protein (DesJarlais et al. (1988) *J Med Chem* 31: 722-729).

The orientations are evaluated for goodness-of-fit and the best are kept for further examination using molecular mechanics programs, such as AMBER or CHARMM. Such algorithms have previously proven successful in finding a variety of chemical entities that are complementary in shape to a druggable region.

Goodford (1985, *J Med Chem* 28:849-857) and Boobbyer et al. (1989, *J Med Chem* 32:1083-1094) have produced a computer program (GRID) which seeks to determine regions or high affinity for different chemical groups (termed probes) of the druggable region. GRID hence provides a tool for suggesting modifications to known chemical entities that might enhance binding. It may be anticipated that some of the sites discerned by GRID as regions of high affinity correspond to "pharmacophoric patterns" determined interferentially from a series of known ligands. As used herein, a "pharmacophoric pattern" is a geometric arrangement of features of chemical entities that is believed to be important for binding. Attempts have been made to use pharmacophoric patterns as a search screen for novel ligands (Jakes et al. (1987) *J Mol Graph* 5:41-48; Brint et al. (1987) *J Graph* 5:49-56; Jakes et al. (1986) *J Mol Graph* 4:12-20).

Yet a further embodiment of the present invention utilizes a computer algorithm such as CLIX which searches such databases as CCDB for chemical entities which can be oriented with the druggable region in a way that is both sterically acceptable and has a high likelihood of achieving favorable chemical interactions between the chemical entity and the surrounding amino acid residues. The method is based on characterizing the region in terms of an ensemble of favorable binding positions for different chemical groups and then searching for orientations of the chemical entities that cause maximum spatial coincidence of individual candidate chemical groups with members of the ensemble. The algorithmic details of CLIX is described in Lawrence et al. (1992) *Proteins* 12:31-41.

In this way, the efficiency with which a chemical entity may bind to or interfere with a druggable region may be tested and optimized by computational evaluation. For example, for a favorable association with a druggable region, a chemical entity must preferably demonstrate a relatively small difference in energy between its bound and fine states (i.e., a small deformation energy of binding). Thus, certain, more desirable chemical entities will be designed with a deformation energy of binding of not greater than about 10 kcal/mole, and more preferably, not greater than 7 kcal/mole. Chemical entities may interact with a druggable region in more than one conformation that is similar in overall binding energy. In those cases, the deformation energy of binding is taken to be the difference between the energy of the free entity and the average energy of the conformations observed when the chemical entity binds to the target.

In this way, the present invention provides computer-assisted methods for identifying or designing a potential modulator of the activity of a dengue virus E protein or other class II E protein including: supplying a computer modeling application with a set of structure coordinates of a molecule or complex, the molecule or complex including at least a portion of a druggable region from a dengue virus E protein or other class II E protein; supplying the computer modeling application with a set of structure coordinates of a chemical entity; and determining whether the chemical entity is expected to bind to the molecule or complex, wherein binding to the molecule or complex is indicative of potential modulation of the activity of a dengue virus E protein or other class II E protein.

In another aspect, the present invention provides a computer-assisted method for identifying or designing a potential modulator to a dengue virus E protein or other class II E protein, supplying a computer modeling application with a set of structure coordinates of a molecule or complex, the molecule or complex including at least a portion of a druggable region of a dengue virus E protein or other class II E protein; supplying the computer modeling application with a set of structure coordinates for a chemical entity; evaluating the potential binding interactions between the chemical entity and active site of the molecule or molecular complex; structurally modifying the chemical entity to yield a set of structure coordinates for a modified chemical entity, and determining whether the modified chemical entity is expected to bind to the molecule or complex, wherein binding to the molecule or complex is indicative of potential modulation of the dengue virus E protein or other class II E protein.

In one embodiment, a potential modulator can be obtained by screening a peptide or other compound or chemical library (Scott and Smith, Science, 249:386-390 (1990); Cwirla et al., Proc. Natl. Acad. Sci., 87:6378-6382 (1990); Devlin et al., Science, 249:404-406 (1990)). A potential modulator selected in this manner could then be systematically modified by computer modeling programs until one or more promising potential drugs are identified. Such analysis has been shown to be effective in the development of HIV protease modulators (Lam et al., Science 263:380-384 (1994); Wlodawer et al., Ann. Rev. Biochem. 62:543-585 (1993); Appelt, Perspectives in Drug Discovery and Design 1:23-48 (1993); Erickson, Perspectives in Drug Discovery and Design 1:109-128 (1993)). Alternatively a potential modulator may be selected from a library of chemicals such as those that can be licensed from third parties, such as chemical and pharmaceutical companies. A third alternative is to synthesize the potential modulator de novo.

For example, in certain embodiments, the present invention provides a method for making a potential modulator for a dengue virus E protein or other class II E protein, the method including synthesizing a chemical entity or a molecule containing the chemical entity to yield a potential modulator of a dengue virus E protein or other class II E protein, the chemical entity having been identified during a computer-assisted process including supplying a computer modeling application with a set of structure coordinates of a molecule or complex, the molecule or complex including at least one druggable region from a dengue virus E protein or other class II E protein; supplying the computer modeling application with a set of structure coordinates of a chemical entity; and determining whether the chemical entity is expected to bind to the molecule or complex at the active site, wherein binding to the molecule or complex is indicative of potential modulation. This method may further include the steps of evaluating the potential binding interactions between the chemical entity and the active site of the molecule or molecular complex and structurally modifying the chemical entity to yield a set of structure coordinates for a modified chemical entity, which steps may be repeated one or more times.

Once a potential modulator is identified, it can then be tested in any standard assay for the macromolecule depending of course on the macromolecule, including in high throughput assays. Further refinements to the structure of the modulator will generally be necessary and can be made by the successive iterations of any and/or all of the steps provided by the particular screening assay, in particular further structural analysis by e.g., $^{15}$N NMR relaxation rate determinations or x-ray crystallography with the modulator bound to a dengue virus E protein or other class II E protein. These studies may be performed in conjunction with biochemical assays.

Once identified, a potential modulator may be used as a model structure, and analogs to the compound can be obtained. The analogs are then screened for their ability to bind to a dengue virus E protein or other class II E protein. An analog of the potential modulator might be chosen as a modulator when it binds to a dengue virus E protein or other class II E protein with a higher binding affinity than the predecessor modulator.

In a related approach, iterative drug design is used to identify modulators of a target protein. Iterative drug design is a method for optimizing associations between a protein and a modulator by determining and evaluating the three dimensional structures of successive sets of protein/modulator complexes. In iterative drug design, crystals of a series of protein/modulator complexes are obtained and then the three-dimensional structures of each complex is solved. Such an approach provides insight into the association between the proteins and modulators of each complex. For example, this approach may be accomplished by selecting modulators with modulatory activity, obtaining crystals of this new protein/modulator complex, solving the three dimensional structure of the complex, and comparing the associations between the new protein/modulator complex and previously solved protein/modulator complexes. By observing how changes in the modulator affected the protein/modulator associations, these associations may be optimized.

In addition to designing and/or identifying a chemical entity to associate with a druggable region, as described above, the same techniques and methods may be used to design and/or identify chemical entities that either associate, or do not associate, with affinity regions, selectivity regions or undesired regions of protein targets. By such methods, selectivity for one or a few targets, or alternatively for multiple targets, from the same species or from multiple species, can be achieved.

For example, a chemical entity may be designed and/or identified for which the binding energy for one druggable region, e.g., an affinity region or selectivity region, is more favorable than that for another region, e.g., an undesired region, by about 20%, 30%, 50% to about 60% or more. It may be the case that the difference is observed between (a) more than two regions, (b) between different regions (selectivity, affinity or undesirable) from the same target, (c) between regions of different targets, (d) between regions of homologs from different species, or (e) between other combinations. Alternatively, the comparison may be made by reference to the Kd, usually the apparent Kd, of said chemical entity with the two or more regions in question.

In another aspect, prospective modulators are screened for binding to two nearby druggable regions on a target protein. For example, a modulator that binds a first region of a target polypeptide does not bind a second nearby region. Binding to the second region can be determined by monitoring changes in a different set of amide chemical shifts in either the original screen or a second screen conducted in the presence of a modulator (or potential modulator) for the first region. From an analysis of the chemical shift changes, the approximate location of a potential modulator for the second region is identified. Optimization of the second modulator for binding to the region is then carried out by screening structurally related compounds (e.g., analogs as described above). When modulators for the first region and the second region are identified, their location and orientation in the ternary complex can be determined experimentally. On the basis of this structural information, a linked compound, e.g., a consolidated modulator, is synthesized in which the modulator for the first region and the modulator for the second region are linked. In certain embodiments, the two modulators are covalently linked to form a consolidated modulator. This consolidated modulator may be tested to determine if it has a higher binding affinity for the target than either of the two individual modulators. A consolidated modulator is selected as a modulator when it has a higher binding affinity for the target than either of the two modulators. Larger consolidated modulators can be constructed in an analogous manner, e.g., linking three modulators which bind to three nearby regions on the target to form a multilinked consolidated modulator that has an even higher affinity for the target than the linked modulator. In this example, it is assumed that is desirable to have the modulator bind to all the druggable regions. However, it may be the case that binding to certain of the druggable regions is not desirable, so that the same techniques may be used to identify modulators and consolidated modulators that show increased specificity based on binding to at least one but not all druggable regions of a target.

The present invention provides a number of methods that use drug design as described above. For example, in one aspect, the present invention contemplates a method for designing a candidate compound for screening for modulators of a dengue virus E protein or other class II E protein, the method comprising: (a) determining the three dimensional structure of a crystallized dengue virus E protein or other class II E protein or a fragment thereof; and (b) designing a candidate modulator based on the three dimensional structure of the crystallized polypeptide or fragment.

In another aspect, the present invention contemplates a method for identifying a potential modulator of a dengue virus E protein or other class II E protein, the method comprising: (a) providing the three-dimensional coordinates of a dengue virus E protein or other class II E protein or a fragment thereof; (b) identifying a druggable region of the polypeptide or fragment; and (c) selecting from a database at least one compound that comprises three dimensional coordinates which indicate that the compound may bind the druggable region; (d) wherein the selected compound is a potential modulator of a dengue virus E protein or other class II E protein.

In another aspect, the present invention contemplates a method for identifying a potential modulator of a molecule comprising a druggable region similar to that of an E protein k1 hairpin, the method comprising: (a) using the atomic coordinates of amino acid residues from a druggable region, such as an E protein k1 hairpin, or a fragment thereof, ±a root mean square deviation from the backbone atoms of the amino acids of not more than 1.5 Å, to generate a three-dimensional structure of a molecule comprising an E protein k1 hairpin-like druggable region; (b) employing the three dimensional structure to design or select the potential modulator; (c) synthesizing the modulator; and (d) contacting the modulator with the molecule to determine the ability of the modulator to interact with the molecule.

In another aspect, the present invention contemplates an apparatus for determining whether a compound is a potential modulator of a dengue virus E protein or other class II E protein, the apparatus comprising: (a) a memory that comprises: (i) the three dimensional coordinates and identities of the atoms of a dengue virus E protein or other class II E protein or a fragment thereof that form a druggable site, such as for example, an E protein k1 hairpin; and (ii) executable instructions; and (b) a processor that is capable of executing instructions to: (i) receive three-dimensional structural information for a candidate compound; (ii) determine if the three-dimensional structure of the candidate compound is complementary to the structure of the interior of the druggable site; and (iii) output the results of the determination.

In another aspect, the present invention contemplates a method for designing a potential compound for the prevention or treatment of a flavivirus related disease or disorder, the method comprising: (a) providing the three dimensional structure of a crystallized dengue virus E protein or other class II E protein, or a fragment thereof; (b) synthesizing a potential compound for the prevention or treatment of flavivirus related disease or disorder based on the three dimensional structure of the crystallized polypeptide or fragment; (c) contacting a dengue virus E protein or other class II E protein with the potential compound; and (d) assaying the activity of a dengue virus E protein or other class II E protein, wherein a change in the activity of the polypeptide indicates that the compound may be useful for prevention or treatment of a flavivirus related disease or disorder.

In another aspect, the present invention contemplates a method for designing a potential compound for the prevention or treatment of flavivirus related disease or disorder, the method comprising: (a) providing structural information of a druggable region derived from NMR spectroscopy of a dengue virus E protein or other class II E protein, or a fragment thereof; (b) synthesizing a potential compound for the prevention or treatment of flavivirus related disease or disorder based on the structural information; (c) contacting a dengue virus E protein or other class II E protein or a flavivirus with the potential compound; and (d) assaying the activity of a dengue virus E protein or other class II E protein, wherein a change in the activity of the polypeptide indicates that the compound may be useful for prevention or treatment of a flavivirus related disease or disorder.

(b) Modulator Libraries

The synthesis and screening of combinatorial libraries is a validated strategy for the identification and study of organic molecules of interest. According to the present invention, the synthesis of libraries containing molecules bind, interact with, or modulate the activity/function of a subject druggable region may be performed using established combinatorial methods for solution phase, solid phase, or a combination of solution phase and solid phase synthesis techniques. The synthesis of combinatorial libraries is well known in the art and has been reviewed (see, e.g., "Combinatorial Chemistry", Chemical and Engineering News, Feb. 24, 1997, p. 43; Thompson et al., Chem. Rev. (1996) 96:555). Many libraries are commercially available. One of ordinary skill in the art will realize that the choice of method for any particular embodiment will depend upon the specific number of molecules to be synthesized, the specific reaction chemistry, and the availability of specific instrumentation, such as robotic instrumentation for the preparation and analysis of the inventive libraries. In certain embodiments, the reactions to be performed to generate the libraries are selected for their ability to proceed in high yield, and in a stereoselective and regioselective fashion, if applicable.

In one aspect of the present invention, the inventive libraries are generated using a solution phase technique. Traditional advantages of solution phase techniques for the synthesis of combinatorial libraries include the availability of a much wider range of reactions, and the relative ease with which products may be characterized, and ready identification of library members, as discussed below. For example, in certain embodiments, for the generation of a solution phase combinatorial library, a parallel synthesis technique is utilized, in which all of the products are assembled separately in their own reaction vessels. In a particular parallel synthesis procedure, a microtitre plate containing n rows and m columns of tiny wells which are capable of holding a few milliliters of the solvent in which the reaction will occur, is utilized. It is possible to then use n variants of reactant A, such as a ligand, and m variants of reactant B, such as a second ligand, to obtain n×m variants, in n×m wells. One of ordinary skill in the art will realize that this particular procedure is most useful when smaller libraries are desired, and the specific wells may provide a ready means to identify the library members in a particular well.

In other embodiments of the present invention, a solid phase synthesis technique is utilized. Solid phase techniques allow reactions to be driven to completion because excess reagents may be utilized and the unreacted reagent washed away. Solid phase synthesis also allows the use a technique called "split and pool", in addition to the parallel synthesis technique, developed by Furka. See, e.g., Furka et al., Abstr. 14th Int. Congr. Biochem., (Prague, Czechoslovakia) (1988) 5:47; Furka et al., Int. J. Pept. Protein Res. (1991) 37:487; Sebestyen et al., Bioorg. Med. Chem. Lett. (1993) 3:413. In this technique, a mixture of related molecules may be made in the same reaction vessel, thus substantially reducing the number of containers required for the synthesis of very large libraries, such as those containing as many as or more than one million library members. As an example, the solid support with the starting material attached may be divided into n vessels, where n represents the number species of reagent A to be reacted with the such starting material. After reaction, the contents from n vessels are combined and then split into m vessels, where m represents the number of species of reagent B to be reacted with the now modified starting materials. This procedure is repeated until the desired number of reagents is reacted with the starting materials to yield the inventive library.

The use of solid phase techniques in the present invention may also include the use of a specific encoding technique. Specific encoding techniques have been reviewed by Czarnik in Current Opinion in Chemical Biology (1997) 1:60. One of ordinary skill in the art will also realize that if smaller solid phase libraries are generated in specific reaction wells, such as 96 well plates, or on plastic pins, the reaction history of these library members may also be identified by their spatial coordinates in the particular plate, and thus are spatially encoded. In other embodiments, an encoding technique involves the use of a particular "identifying agent" attached to the solid support, which enables the determination of the structure of a specific library member without reference to its spatial coordinates. Examples of such encoding techniques include, but are not limited to, spatial encoding techniques, graphical encoding techniques, including the "tea bag" method, chemical encoding methods, and spectrophotometric encoding methods. One of ordinary skill in the art will realize that the particular encoding method to be used in the present invention must be selected based upon the number of library members desired, and the reaction chemistry employed.

In certain embodiments, molecules of the present invention may be prepared using solid support chemistry known in the art. For example, polypeptides having up to twenty amino acids or more may be generated using standard solid phase technology on commercially available equipment (such as Advanced Chemtech multiple organic synthesizers). In certain embodiments, a starting material or later reactant may be attached to the solid phase, through a linking unit, or directly, and subsequently used in the synthesis of desired molecules. The choice of linkage will depend upon the reactivity of the molecules and the solid support units and the stability of these linkages. Direct attachment to the solid support via a linker molecule may be useful if it is desired not to detach the library member from the solid support. For example, for direct on-bead analysis of biological activity, a stronger interaction between the library member and the solid support may be desirable. Alternatively, the use of a linking reagent may be useful if more facile cleavage of the inventive library members from the solid support is desired.

In regard to automation of the present subject methods, a variety of instrumentation may be used to allow for the facile and efficient preparation of chemical libraries of the present invention, and methods of assaying members of such libraries. In general, automation, as used in reference to the synthesis and preparation of the subject chemical libraries, involves having instrumentation complete one or more of the operative steps that must be repeated a multitude of times because a library instead of a single molecule is being prepared. Examples of automation include, without limitation, having instrumentation complete the addition of reagents, the mixing and reaction of them, filtering of reaction mixtures, washing of solids with solvents, removal and addition of solvents, and the like. Automation may be applied to any steps in a reaction scheme, including those to prepare, purify and assay molecules for use in the compositions of the present invention.

There is a range of automation possible. For example, the synthesis of the subject libraries may be wholly automated or only partially automated. If wholly automated, the subject library may be prepared by the instrumentation without any human intervention after initiating the synthetic process, other than refilling reagent bottles or monitoring or programming the instrumentation as necessary. Although synthesis of a subject library may be wholly automated, it may be necessary for there to be human intervention for purification, identification, or the like of the library members.

In contrast, partial automation of the synthesis of a subject library involves some robotic assistance with the physical steps of the reaction schema that gives rise to the library, such as mixing, stirring, filtering and the like, but still requires some human intervention other than just refilling reagent bottles or monitoring or programming the instrumentation. This type of robotic automation is distinguished from assistance provided by convention organic synthetic and biological techniques because in partial automation, instrumentation still completes one or more of the steps of any schema that is required to be completed a multitude of times because a library of molecules is being prepared.

In certain embodiments, the subject library may be prepared in multiple reaction vessels (e.g., microtitre plates and the like), and the identity of particular members of the library may be determined by the location of each vessel. In other embodiments, the subject library may be synthesized in solution, and by the use of deconvolution techniques, the identity of particular members may be determined.

In one aspect of the invention, the subject screening method may be carried out utilizing immobilized libraries. In certain embodiments, the immobilized library will have the ability to bind to a microorganism as described above. The choice of a suitable support will be routine to the skilled artisan. Important criteria may include that the reactivity of the support not interfere with the reactions required to prepare the library. Insoluble polymeric supports include functionalized polymers based on polystyrene, polystyrene/divinylbenzene copolymers, and the like, including any of the particles described in section 4.3. It will be understood that the polymeric support may be coated, grafted or otherwise bonded to other solid supports.

In another embodiment, the polymeric support may be provided by reversibly soluble polymers. Such polymeric supports include functionalized polymers based on polyvinyl alcohol or polyethylene glycol (PEG). A soluble support may be made insoluble (e.g., may be made to precipitate) by addition of a suitable inert nonsolvent. One advantage of reactions performed using soluble polymeric supports is that reactions in solution may be more rapid, higher yielding, and more complete than reactions that are performed on insoluble polymeric supports.

Once the synthesis of either a desired solution phase or solid support bound template has been completed, the template is then available for further reaction to yield the desired solution phase or solid support bound structure. The use of solid support bound templates enables the use of more rapid split and pool techniques.

Characterization of the library members may be performed using standard analytical techniques, such as mass spectrometry, Nuclear Magnetic Resonance Spectroscopy, including 195Pt and 1H NMR, chromatography (e.g., liquid etc.) and infra-red spectroscopy. One of ordinary skill in the art will realize that the selection of a particular analytical technique will depend upon whether the inventive library members are in the solution phase or on the solid phase. In addition to such characterization, the library member may be synthesized separately to allow for more ready identification.

(c) In Vitro Assays

Any form of dengue virus E protein or other class II E protein, e.g. a full-length polypeptide or a fragment comprising the target druggable region, may be used to assess the activity of candidate small molecules and other modulators in in vitro assays. In one embodiment of such an assay, agents are identified which modulate the biological activity of a druggable region, the protein-protein interaction of interest or formation of a protein complex involving a subject druggable region. In another embodiment of such an assay, agents are identified which bind or interact with subject druggable region. In certain embodiments, the test agent is a small organic molecule. The candidate agents may be selected, for example, from the following classes of compounds: detergents, proteins, peptides, peptidomimetics, small molecules, cytokines, or hormones. In some embodiments, the candidate therapeutics may be in a library of compounds. These libraries may be generated using combinatorial synthetic methods as described above. In certain embodiments of the present invention, the ability of said candidate therapeutics to bind a target gene or gene product may be evaluated by an in vitro assay. In either embodiments, discussed in the next section, the binding assay may also be in vivo.

The invention also provides a method of screening multiple compounds to identify those which modulate the action of polypeptides of the invention, or polynucleotides encoding the same. The method of screening may involve high-throughput techniques. For example, to screen for modulators, a synthetic reaction mix, a cellular compartment, such as a membrane, cell envelope or cell wall, or a preparation of any thereof, a whole cell or tissue, or even a whole organism comprising a dengue virus E protein or other class II E protein and a labeled substrate or ligand of such polypeptide is incubated in the absence or the presence of a candidate molecule that may be a modulator of a dengue virus E protein or other class II E protein. The ability of the candidate molecule to modulate a dengue virus E protein or other class II E protein is reflected in decreased binding of the labeled ligand or decreased production of product from such substrate. Detection of the rate or level of production of product from substrate may be enhanced by using a reporter system. Reporter systems that may be useful in this regard include but are not limited to colorimetric labeled substrate converted into product, a reporter gene that is responsive to changes in a nucleic acid of the invention or polypeptide activity, and binding assays known in the art.

Another example of an assay for a modulator of a dengue virus E protein or other class II E protein is a competitive assay that combines a dengue virus E protein or other class II E protein and a potential modulator with molecules that bind to a dengue virus E protein or other class II E protein, recombinant molecules that bind to a dengue virus E protein or other class II E protein, natural substrates or ligands, or substrate or ligand mimetics, under appropriate conditions for a competitive inhibition assay. Polypeptides of the invention can be labeled, such as by radioactivity or a colorimetric compound, such that the number of molecules of a dengue virus E protein or other class II E protein bound to a binding molecule or converted to product can be determined accurately to assess the effectiveness of the potential modulator.

A number of methods for identifying a molecule which modulates the activity of a polypeptide are known in the art. For example, in one such method, a dengue virus E protein or other class II E protein is contacted with a test compound, and the activity of the dengue virus E protein or other class II E protein in the presence of the test compound is determined, wherein a change in the activity of the dengue virus E protein or other class II E protein is indicative that the test compound modulates the activity of the dengue virus E protein or other class II E protein. In certain instances, the test compound agonizes the activity of the dengue virus E protein or other class II E protein, and in other instances, the test compound antagonizes the activity of the dengue virus E protein or other class II E protein.

In another example, a compound which modulates dengue virus E protein or other class II E protein dependent growth or infectivity of flavivirus may be identified by (a) contacting a dengue virus E protein or other class II E protein with a test compound; and (b) determining the activity of the polypeptide in the presence of the test compound, wherein a change in the activity of the polypeptide is indicative that the test compound may modulate the growth or infectivity of flavivirus.

In certain of the subject assays, to evaluate the results using the subject compositions, comparisons may be made to known molecules, such as one with a known binding affinity for the target. For example, a known molecule and a new molecule of interest may be assayed. The result of the assay for the subject complex will be of a type and of a magnitude that may be compared to result for the known molecule. To the extent that the subject complex exhibits a type of response in the assay that is quantifiably different from that of the known molecule then the result for such complex in the assay would be deemed a positive or negative result. In certain assays, the magnitude of the response may be expressed as a percentage response with the known molecule result, e.g. 100% of the known result if they are the same.

As those skilled in the art will understand, based on the present description, binding assays may be used to detect agents that bind a polypeptide. Cell-free assays may be used to identify molecules that are capable of interacting with a polypeptide. In a preferred embodiment, cell-free assays for identifying such molecules are comprised essentially of a reaction mixture containing a target and a test molecule or a library of test molecules. A test molecule may be, e.g., a derivative of a known binding partner of the target, e.g., a biologically inactive peptide, or a small molecule. Agents to be tested for their ability to bind may be produced, for example, by bacteria, yeast or other organisms (e.g. natural products), produced chemically (e.g. small molecules, including peptidomimetics), or produced recombinantly. In certain embodiments, the test molecule is selected from the group consisting of lipids, carbohydrates, peptides, peptidomimetics, peptide-nucleic acids (PNAs), proteins, small molecules, natural products, aptamers and oligonucleotides. In other embodiments of the invention, the binding assays are not cell-free. In a preferred embodiment, such assays for identifying molecules that bind a target comprise a reaction mixture containing a target microorganism and a test molecule or a library of test molecules.

In many candidate screening programs which test libraries of molecules and natural extracts, high throughput assays are desirable in order to maximize the number of molecules surveyed in a given period of time. Assays of the present invention which are performed in cell-free systems, such as may be derived with purified or semi-purified proteins or with lysates, are often preferred as "primary" screens in that they may be generated to permit rapid development and relatively easy detection of binding between a target and a test molecule. Moreover, the effects of cellular toxicity and/or bio-availability of the test molecule may be generally ignored in the in vitro system, the assay instead being focused primarily on the ability of the molecule to bind the target. Accordingly, potential binding molecules may be detected in a cell-free assay generated by constitution of functional interactions of interest in a cell lysate. In an alternate format, the assay may be derived as a reconstituted protein mixture which, as described below, offers a number of benefits over lysate-based assays.

In one aspect, the present invention provides assays that may be used to screen for molecules that bind E protein druggable regions. In an exemplary binding assay, the molecule of interest is contacted with a mixture generated from target cell surface polypeptides. Detection and quantification of expected binding from to a target polypeptide provides a means for determining the molecule's efficacy at binding the target. The efficacy of the molecule may be assessed by generating dose response curves from data obtained using various concentrations of the test molecule. Moreover, a control assay may also be performed to provide a baseline for comparison. In the control assay, the formation of complexes is quantitated in the absence of the test molecule.

Complex formation between a molecule and a target E protein or microorganism containing a class II E protein may be detected by a variety of techniques, many of which are effectively described above. For instance, modulation in the formation of complexes may be quantitated using, for example, detectably labeled proteins (e.g. radiolabeled, fluorescently labeled, or enzymatically labeled), by immunoassay, or by chromatographic detection.

Accordingly, one exemplary screening assay of the present invention includes the steps of contacting a class II E protein or functional fragment thereof with a test molecule or library of test molecules and detecting the formation of complexes. For detection purposes, for example, the molecule may be labeled with a specific marker and the test molecule or library of test molecules labeled with a different marker. Interaction of a test molecule with a polypeptide or fragment thereof may then be detected by determining the level of the two labels after an incubation step and a washing step. The presence of two labels after the washing step is indicative of an interaction. Such an assay may also be modified to work with a whole target cell.

An interaction between a class II E protein target and a molecule may also be identified by using real-time BIA (Biomolecular Interaction Analysis, Pharmacia Biosensor AB) which detects surface plasmon resonance (SPR), an optical phenomenon. Detection depends on changes in the mass concentration of macromolecules at the biospecific interface, and does not require any labeling of interactants. In one embodiment, a library of test molecules may be immobilized on a sensor surface, e.g., which forms one wall of a micro-flow cell. A solution containing the target is then flowed continuously over the sensor surface. A change in the resonance angle as shown on a signal recording, indicates that an interaction has occurred. This technique is further described, e.g., in BIAtechnology Handbook by Pharmacia.

In a preferred embodiment, it will be desirable to immobilize the target to facilitate separation of complexes from uncomplexed forms, as well as to accommodate automation of the assay. Binding of polypeptide to a test molecule may be accomplished in any vessel suitable for containing the reactants. Examples include microtitre plates, test tubes, and micro-centrifuge tubes. In one embodiment, a fusion protein may be provided which adds a domain that allows the target to be bound to a matrix. For example, glutathione-S-transferase/polypeptide (GST/polypeptide) fusion proteins may be adsorbed onto glutathione sepharose beads (Sigma Chemical, St. Louis, Mo.) or glutathione derivatized microtitre plates, which are then combined with a labeled test molecule (e.g., $S^{35}$ labeled, $P^{33}$ labeled, and the like, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes may be dissociated from the matrix, separated by SDS-PAGE, and the level of polypeptide or binding partner found in the bead fraction quantitated from the gel using standard electrophoretic techniques such as described in the appended examples. The above techniques could also be modified in which the test molecule is immobilized, and the labeled target is incubated with the immobilized test molecules. In one embodiment of the invention, the test molecules are immobilized, optionally via a linker, to a particle of the invention, e.g. to create the ultimate composition.

Other techniques for immobilizing targets or molecules on matrices may be used in the subject assays. For instance, a target or molecule may be immobilized utilizing conjugation of biotin and streptavidin. For instance, biotinylated polypeptide molecules may be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with a target or molecule may be derivatized to the wells of the plate, and the target or molecule trapped in the wells by antibody conjugation. As above, preparations of test molecules are incubated in the polypeptide presenting wells of the plate, and the amount of complex trapped in the well may be quantitated. Exemplary methods for detecting such complexes, in addition to those described above for the GST-immobilized complexes, include immunodetection of complexes using antibodies reactive with the complex, or which are reactive with one of the complex components; as well as enzyme-linked assays which rely on detecting an enzymatic activity associated with a target or molecule, either intrinsic or extrinsic activity. In an instance of the latter, the enzyme may be chemically conjugated or provided as a fusion protein with the target or molecule. To illustrate, a target polypeptide may be chemically cross-linked or genetically fused with horseradish peroxidase, and the amount of polypeptide trapped in a complex with a molecule may be assessed with a chromogenic substrate of the enzyme, e.g. 3,3'-diamino-benzadine tetrahydrochloride or 4-chloro-1-napthol. Likewise, a fusion protein comprising the polypeptide and glutathione-S-transferase may be provided, and complex formation quantitated by detecting the GST activity using 1-chloro-2,4-dinitrobenzene (Habig et al (1974) *J Biol Chem* 249:7130).

For processes that rely on immunodetection for quantitating one of the components trapped in a complex, antibodies against a component, such as anti-polypeptide antibodies, may be used. Alternatively, the component to be detected in the complex may be "epitope tagged" in the form of a fusion protein which includes, in addition to the polypeptide sequence, a second polypeptide for which antibodies are readily available (e.g. from commercial sources). For instance, the GST fusion proteins, described above may also be used for quantification of binding using antibodies against the GST moiety. Other useful epitope tags include myc-epitopes (e.g., see Ellison et al. (1991) J Biol Chem 266: 21150-21157) which includes a 10-residue sequence from c-myc, as well as the pFLAG system (International Biotechnologies, Inc.) or the pEZZ-protein A system (Pharmacia, NJ).

In certain in vitro embodiments of the present assay, the solution containing the target comprises a reconstituted protein mixture of at least semi-purified proteins. By semi-purified, it is meant that the components utilized in the reconstituted mixture have been previously separated from other cellular or viral proteins. For instance, in contrast to cell lysates, a target protein is present in the mixture to at least 50% purity relative to all other proteins in the mixture, and more preferably are present at 90-95% purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure binding activity.

In one embodiment, the use of reconstituted protein mixtures allows more careful control of the target:molecule interaction conditions.

In still other embodiments of the present invention, variations of viral fusion or viral infectivity assays may be utilized in order to determine the ability of a test molecule to prevent a virus expressing type II E protein from binding to, fusing with, or infecting cells. If fusion, binding, or infecting is prevented, then the molecule or composition may be useful as a therapeutic agent.

All of the screening methods may be accomplished by using a variety of assay formats. In light of the present disclosure, those not expressly described herein will nevertheless be known and comprehended by one of ordinary skill in the art. Assay formats which approximate such conditions as formation of protein complexes or protein-nucleic acid complexes, and enzymatic activity may be generated in many different forms, as those skilled in the art will appreciate based on the present description and include but are not limited to assays based on cell-free systems, e.g. purified proteins or cell lysates, as well as cell-based assays which utilize intact cells. Assaying binding resulting from a given target:molecule interaction may be accomplished in any vessel suitable for containing the reactants. Examples include microtitre plates, test tubes, and micro-centrifuge tubes. Any of the assays may be provided in kit format and may be automated. Many of the following particularized assays rely on general principles, such as blockage or prevention of fusion, that may apply to other particular assays.

(d) In Vivo Assays

Animal models of viral infection and/or disease may be used as an in vivo assay for evaluating the effectiveness of a potential drug target in treating or preventing flavivirus related diseases or disorders. A number of suitable animal models are described briefly below, however, these models are only examples and modifications, or completely different animal models, may be used in accord with the methods of the invention. Animal models may be developed by methods known in the art, for example, by infecting an animal with dengue fever or another flavivirus, or by genetically engineering an animal to be predisposed to such infection (see, e.g., Wu, S.-J. L. et al. Evaluation of the severe combined immunodeficient (SCID) mouse as an animal model for dengue viral infection. Am. J. Trop. Med. Hyg. 52, 468-476 (1995)).

Further, viral infectivity assays may be used as in vivo assays to assess the effectiveness of a potential drug target in treating or preventing flavivirus related diseases or disorders. For example, the plaque assays described in Diamond et al (2000) *J Virol* 74:4957-4966 may be used to assess by analyzing virion production whether an agent may modulate infectivity of Dengue virus. Other assays, such as competitive, asymmetric reverse transcriptase-mediated PCR (RT-PCR) assays and flow cytometric assays that measure viral antigen, also described in Diamond, et al, may be used to assess the effectiveness of a potential drug target.

Still further, further, cell-cell fusion assays may be used as in vivo assays to assess the effectiveness of a potential drug target in treating or preventing flavivirus related diseases or disorders. For example, a cell-cell fusion assay in which the cell membrane fusion activity of dengue virus may be analyzed is described in Després et al (1993) *Virology* 196:209-219.

A variety of other in vivo models are available and may be used when appropriate for specific pathogens or specific test agents.

It is also relevant to note that the species of animal used for an infection model, and the specific genetic make-up of that animal, may contribute to the effective evaluation of the effects of a particular test agent. For example, immuno-incompetent animals may, in some instances, be preferable to immuno-competent animals. For example, the action of a competent immune system may, to some degree, mask the effects of the test agent as compared to a similar infection in an immuno-incompetent animal. In addition, many opportunistic infections, in fact, occur in immuno-compromised patients, so modeling an infection in a similar immunological environment is appropriate.

E. Pharmaceutical Compositions

Pharmaceutical compositions of this invention include any modulator identified according to the present invention, or a pharmaceutically acceptable salt thereof, and a pharmaceutically acceptable carrier, adjuvant, or vehicle. The term "pharmaceutically acceptable carrier" refers to a carrier(s) that is "acceptable" in the sense of being compatible with the other ingredients of a composition and not deleterious to the recipient thereof.

Methods of making and using such pharmaceutical compositions are also included in the invention. The pharmaceutical compositions of the invention can be administered orally, parenterally, by inhalation spray, topically, rectally, nasally, buccally, vaginally, or via an implanted reservoir. The term parenteral as used herein includes subcutaneous, intracutaneous, intravenous, intramuscular, intra articular, intrasynovial, intrasternal, intrathecal, intralesional, and intracranial injection or infusion techniques.

Dosage levels of between about 0.01 and about 100 mg/kg body weight per day, preferably between about 0.5 and about 75 mg/kg body weight per day of the modulators described herein are useful for the prevention and treatment of disease and conditions, including diseases and conditions mediated by pathogenic species of origin for the polypeptides of the invention. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

G. Kits

The present invention provides kits for treating dengue fever and other flaviviral infections. For example, a kit may comprise compositions comprising compounds identified herein as modulators of dengue virus E protein or other class II E protein. The compositions may be pharmaceutical compositions comprising a pharmaceutically acceptable excipient. In other embodiments involving kits, this invention contemplates a kit including compositions of the present invention, and optionally instructions for their use. Kit components may be packaged for either manual or partially or wholly automated practice of the foregoing methods. Such kits may have a variety of uses, including, for example, imaging, diagnosis, therapy, and other applications.

H. Further Characterization of Dengue Virus E Protein or Other Flavivirus E Protein Druggable Regions and Complexes of the Same H.1. Analysis of Proteins by X-Ray Crystallography
(i) X-Ray Structure Determination Exemplary methods for obtaining the three dimensional structure of the crystalline form of a molecule or complex are described herein and, in view of this specification, variations on these methods will be apparent to those skilled in the art (see Ducruix and Geige 1992, IRL Press, Oxford, England).

A variety of methods involving x-ray crystallography are contemplated by the present invention. For example, the present invention contemplates producing a dengue virus E protein or other class II E protein, or a fragment or a complex, such as a trimer, thereof, by: (a) introducing into a host cell an expression vector comprising a nucleic acid encoding for a dengue virus E protein or other class II E protein, or a fragment thereof; (b) culturing the host cell in a cell culture medium to express the protein or fragment; (c) isolating the protein or fragment from the cell culture; and (d) crystallizing the protein or fragment thereof. Optionally, said E protein may be complexed with a molecule or another E protein prior to crystallization. Alternatively, the present invention contemplates determining the three dimensional structure of a crystallized dengue virus E protein or other class II E protein, or a fragment thereof, by: (a) crystallizing a dengue virus E protein or other class II E protein, or a fragment thereof, such that the crystals will diffract x-rays to a resolution of 3.5 Å or better; and (b) analyzing the polypeptide or fragment by x-ray diffraction to determine the three-dimensional structure of the crystallized polypeptide.

X-ray crystallography techniques generally require that the protein molecules be available in the form of a crystal. Crystals may be grown from a solution containing a purified dengue virus E protein or other class II E protein, or a fragment thereof (e.g., a stable domain), by a variety of conventional processes. These processes include, for example, batch, liquid, bridge, dialysis, vapour diffusion (e.g., hanging drop or sitting drop methods). (See for example, McPherson, 1982 John Wiley, New York; McPherson, 1990, Eur. J. Biochem. 189: 1-23; Webber. 1991, Adv. Protein Chem. 41:1-36).

In certain embodiments, native crystals of the invention may be grown by adding precipitants to the concentrated solution of the polypeptide. The precipitants are added at a concentration just below that necessary to precipitate the protein. Water may be removed by controlled evaporation to produce precipitating conditions, which are maintained until crystal growth ceases.

The formation of crystals is dependent on a number of different parameters, including pH, temperature, protein concentration, the nature of the solvent and precipitant, as well as the presence of added ions or ligands to the protein. In addition, the sequence of the polypeptide being crystallized will have a significant affect on the success of obtaining crystals. Many routine crystallization experiments may be needed to screen all these parameters for the few combinations that might give crystal suitable for x-ray diffraction analysis (See, for example, Jancarik, J & Kim, S. H., J. Appl. Cryst. 1991 24: 409-411).

Crystallization robots may automate and speed up the work of reproducibly setting up large number of crystallization experiments. Once some suitable set of conditions for growing the crystal are found, variations of the condition may be systematically screened in order to find the set of conditions which allows the growth of sufficiently large, single, well ordered crystals. In certain instances, a dengue virus E protein or other class II E protein is co-crystallized with a compound that stabilizes the polypeptide.

A number of methods are available to produce suitable radiation for x-ray diffraction. For example, x-ray beams may be produced by synchrotron rings where electrons (or positrons) are accelerated through an electromagnetic field while traveling at close to the speed of light. Because the admitted wavelength may also be controlled, synchrotrons may be used as a tunable x-ray source (Hendrickson W A., Trends Biochem Sci 2000 December; 25(12):637-43). For less conventional Laue diffraction studies, polychromatic x-rays covering a broad wavelength window are used to observe many diffraction intensities simultaneously (Stoddard, B. L., Curr. Opin. Struct Biol 1998 October; 8(5):612-8). Neutrons may also be used for solving protein crystal structures (Gutberlet T, Heinemann U & Steiner M., Acta Crystallogr D 2001; 57: 349-54).

Before data collection commences, a protein crystal may be frozen to protect it from radiation damage. A number of different cryo-protectants may be used to assist in freezing the crystal, such as methyl pentanediol (MPD), isopropanol, ethylene glycol, glycerol, formate, citrate, mineral oil, or a low-molecular-weight polyethylene glycol (PEG). The present invention contemplates a composition comprising a dengue virus E protein or other class II E protein and a cryo-protectant. As an alternative to freezing the crystal, the crystal may also be used for diffraction experiments performed at temperatures above the freezing point of the solution. In these instances, the crystal may be protected from drying out by placing it in a narrow capillary of a suitable material (generally glass or quartz) with some of the crystal growth solution included in order to maintain vapour pressure.

X-ray diffraction results may be recorded by a number of ways known to one of skill in the art. Examples of area electronic detectors include charge coupled device detectors, multi-wire area detectors and phosphoimager detectors (Amemiya, Y, 1997. Methods in Enzymology, Vol. 276. Academic Press, San Diego, pp. 233-243; Westbrook, E. M., Naday, I. 1997. Methods in Enzymology, Vol. 276. Academic Press, San Diego, pp. 244-268; 1997. Kahn, R. & Fourme, R. Methods in Enzymology, Vol. 276. Academic Press, San Diego, pp. 268-286).

A suitable system for laboratory data collection might include a Bruker AXS Proteum R system, equipped with a copper rotating anode source, Confocal Max-Flux™ optics and a SMART 6000 charge coupled device detector. Collection of x-ray diffraction patterns are well documented by those skilled in the art (See, for example, Ducruix and Geige, 1992, IRL Press, Oxford, England).

The theory behind diffraction by a crystal upon exposure to x-rays is well known. Because phase information is not directly measured in the diffraction experiment, and is needed to reconstruct the electron density map, methods that can recover this missing information are required. One method of solving structures ab initio are the real/reciprocal space cycling techniques. Suitable real/reciprocal space cycling search programs include shake-and-bake (Weeks C M, DeTitta G T, Hauptman H A, Thuman P, Miller R Acta Crystallogr A 1994; V50: 210-20).

Other methods for deriving phases may also be needed. These techniques generally rely on the idea that if two or more measurements of the same reflection are made where strong, measurable, differences are attributable to the characteristics of a small subset of the atoms alone, then the contributions of other atoms can be, to a first approximation, ignored, and positions of these atoms may be determined from the difference in scattering by one of the above techniques. Knowing the position and scattering characteristics of those atoms, one may calculate what phase the overall scattering must have had to produce the observed differences.

One version of this technique is isomorphous replacement technique, which requires the introduction of new, well ordered, x-ray scatterers into the crystal. These additions are usually heavy metal atoms, (so that they make a significant difference in the diffraction pattern); and if the additions do not change the structure of the molecule or of the crystal cell, the resulting crystals should be isomorphous. Isomorphous replacement experiments are usually performed by diffusing different heavy-metal metals into the channels of a pre-existing protein crystal. Growing the crystal from protein that has been soaked in the heavy atom is also possible (Petsko, G. A., 1985. Methods in Enzymology, Vol. 114. Academic Press, Orlando, pp. 147-156). Alternatively, the heavy atom may also be reactive and attached covalently to exposed amino acid side chains (such as the sulfur atom of cysteine) or it may be associated through non-covalent interactions. It is sometimes possible to replace endogenous light metals in metallo-proteins with heavier ones, e.g., zinc by mercury, or calcium by samarium (Petsko, G. A., 1985. Methods in Enzymology, Vol. 114. Academic Press, Orlando, pp. 147-156). Exemplary sources for such heavy compounds include, without limitation, sodium bromide, sodium selenate, trimethyl lead acetate, mercuric chloride, methyl mercury acetate, platinum tetracyanide, platinum tetrachloride, nickel chloride, and europium chloride.

A second technique for generating differences in scattering involves the phenomenon of anomalous scattering. X-rays that cause the displacement of an electron in an inner shell to a higher shell are subsequently rescattered, but there is a time lag that shows up as a phase delay. This phase delay is observed as a (generally quite small) difference in intensity between reflections known as Friedel mates that would be identical if no anomalous scattering were present. A second effect related to this phenomenon is that differences in the intensity of scattering of a given atom will vary in a wavelength dependent manner, given rise to what are known as dispersive differences. In principle anomalous scattering occurs with all atoms, but the effect is strongest in heavy atoms, and may be maximized by using x-rays at a wavelength where the energy is equal to the difference in energy between shells. The technique therefore requires the incorporation of some heavy atom much as is needed for isomorphous replacement, although for anomalous scattering a wider variety of atoms are suitable, including lighter metal atoms (copper, zinc, iron) in metallo-proteins. One method for preparing a protein for anomalous scattering involves replacing the methionine residues in whole or in part with selenium containing seleno-methionine. Soaks with halide salts such as bromides and other non-reactive ions may also be effective (Dauter Z, Li M, Wlodawer A., Acta Crystallogr D 2001; 57: 239-49).

In another process, known as multiple anomalous scattering or MAD, two to four suitable wavelengths of data are collected. (Hendrickson, W. A. and Ogata, C. M. 1997 Methods in Enzymology 276, 494-523). Phasing by various combinations of single and multiple isomorphous and anomalous scattering are possible too. For example, SIRAS (single isomorphous replacement with anomalous scattering) utilizes both the isomorphous and anomalous differences for one derivative to derive phases. More traditionally, several different heavy atoms are soaked into different crystals to get sufficient phase information from isomorphous differences while ignoring anomalous scattering, in the technique known as multiple isomorphous replacement (MIR) (Petsko, G. A., 1985. Methods in Enzymology, Vol. 114. Academic Press, Orlando, pp. 147-156).

Additional restraints on the phases may be derived from density modification techniques. These techniques use either generally known features of electron density distribution or known facts about that particular crystal to improve the phases. For example, because protein regions of the crystal scatter more strongly than solvent regions, solvent flattening/flipping may be used to adjust phases to make solvent density a uniform flat value (Zhang, K. Y. J., Cowtan, K. and Main, P. Methods in Enzymology 277, 1997 Academic Press, Orlando pp 53-64). If more than one molecule of the protein is present in the asymmetric unit, the fact that the different molecules should be virtually identical may be exploited to further reduce phase error using non-crystallographic symmetry averaging (Villieux, F. M. D. and Read, R. J. Methods in Enzymology 277, 1997 Academic Press, Orlando pp 18-52). Suitable programs for performing these processes include DM and other programs of the CCP4 suite (Collaborative Computational Project, Number 4. 1994. Acta Cryst. D50, 760-763) and CNX.

The unit cell dimensions, symmetry, vector amplitude and derived phase information can be used in a Fourier transform function to calculate the electron density in the unit cell, i.e., to generate an experimental electron density map. This may be accomplished using programs of the CNX or CCP4 packages. The resolution is measured in Ångstrom (Å) units, and is closely related to how far apart two objects need to be before they can be reliably distinguished. The smaller this number is, the higher the resolution and therefore the greater the amount of detail that can be seen. Preferably, crystals of the invention diffract x-rays to a resolution of better than about 4.0, 3.5, 3.0, 2.5, 2.0, 1.5, 1.0, 0.5 Å or better.

As used herein, the term "modeling" includes the quantitative and qualitative analysis of molecular structure and/or function based on atomic structural information and interaction models. The term "modeling" includes conventional numeric-based molecular dynamic and energy minimization models, interactive computer graphic models, modified molecular mechanics models, distance geometry and other structure-based constraint models.

Model building may be accomplished by either the crystallographer using a computer graphics program such as TURBO or O (Jones, T A. et al., Acta Crystallogr. A47, 100-119, 1991) or, under suitable circumstances, by using a fully automated model building program, such as wARP (Anastassis Perrakis, Richard Morris & Victor S. Lamzin; Nature Structural Biology, May 1999 Volume 6 Number 5 pp 458-463) or MAID (Levitt, D. G., Acta Crystallogr. D 2001 V57: 1013-9). This structure may be used to calculate model-derived diffraction amplitudes and phases. The model-derived and experimental diffraction amplitudes may be compared and the agreement between them can be described by a parameter referred to as R-factor. A high degree of correlation in the amplitudes corresponds to a low R-factor value, with 0.0 representing exact agreement and 0.59 representing a completely random structure. Because the R-factor may be lowered by introducing more free parameters into the model, an unbiased, cross-correlated version of the R-factor known as the R-free gives a more objective measure of model quality. For the calculation of this parameter a subset of reflections (generally around 10%) are set aside at the beginning of the refinement and not used as part of the refinement target. These reflections are then compared to those predicted by the model (Kleywegt G J, Brunger A T, Structure 1996 Aug. 15; 4(8): 897-904).

The model may be improved using computer programs that maximize the probability that the observed data was produced from the predicted model, while simultaneously optimizing the model geometry. For example, the CNX program may be used for model refinement, as can the XPLOR program (1992, Nature 355:472-475, G. N. Murshudov, A. A. Vagin and E. J. Dodson, (1997) Acta Cryst. D 53, 240-255). In order to maximize the convergence radius of refinement, simulated annealing refinement using torsion angle dynamics may be employed in order to reduce the degrees of freedom of motion of the model (Adams P D, Pannu N S, Read R J, Brunger A T., Proc Natl Acad Sci USA 1997 May 13; 94(10):5018-23). Where experimental phase information is available (e.g. where MAD data was collected) Hendrickson-Lattman phase probability targets may be employed. Isotropic or anisotropic domain, group or individual temperature factor refinement, may be used to model variance of the atomic position from its mean. Well defined peaks of electron density not attributable to protein atoms are generally modeled as water molecules. Water molecules may be found by manual inspection of electron density maps, or with automatic water picking routines. Additional small molecules, including ions, cofactors, buffer molecules or substrates may be included in the model if sufficiently unambiguous electron density is observed in a map.

In general, the R-free is rarely as low as 0.15 and may be as high as 0.35 or greater for a reasonably well-determined protein structure. The residual difference is a consequence of approximations in the model (inadequate modeling of residual structure in the solvent, modeling atoms as isotropic Gaussian spheres, assuming all molecules are identical rather than having a set of discrete conformers, etc.) and errors in the data (Lattman E E., Proteins 1996; 25: i-ii). In refined structures at high resolution, there are usually no major errors in the orientation of individual residues, and the estimated errors in atomic positions are usually around 0.1-0.2 up to 0.3 Å.

The three dimensional structure of a new crystal may be modeled using molecular replacement. The term "molecular replacement" refers to a method that involves generating a preliminary model of a molecule or complex whose structure coordinates are unknown, by orienting and positioning a molecule whose structure coordinates are known within the unit cell of the unknown crystal, so as best to account for the observed diffraction pattern of the unknown crystal. Phases may then be calculated from this model and combined with the observed amplitudes to give an approximate Fourier synthesis of the structure whose coordinates are unknown. This, in turn, can be subject to any of the several forms of refinement to provide a final, accurate structure of the unknown crystal. Lattman, E., "Use of the Rotation and Translation Functions", in Methods in Enzymology, 115, pp. 55-77 (1985); M. G. Rossmann, ed., "The Molecular Replacement Method", Int. Sci. Rev. Ser., No. 13, Gordon & Breach, New York, (1972).

Commonly used computer software packages for molecular replacement are CNX, X-PLOR (Brunger 1992, Nature 355: 472-475), AMoRE (Navaza, 1994, Acta Crystallogr. A50:157-163), the CCP4 package, the MERLOT package (P. M. D. Fitzgerald, J. Appl. Cryst., Vol. 21, pp. 273-278, 1988) and XTALVIEW (McCree et al (1992) J. Mol. Graphics. 10: 44-46). The quality of the model may be analyzed using a program such as PROCHECK or 3D-Profiler (Laskowski et al 1993 J. Appl. Cryst. 26:283-291; Luthy R. et al, Nature 356: 83-85, 1992; and Bowie, J. U. et al, Science 253: 164-170, 1991).

Homology modeling (also known as comparative modeling or knowledge-based modeling) methods may also be used to develop a three dimensional model from a polypeptide sequence based on the structures of known proteins. The method utilizes a computer model of a known protein, a computer representation of the amino acid sequence of the polypeptide with an unknown structure, and standard computer representations of the structures of amino acids. This method is well known to those skilled in the art (Greer, 1985, Science 228, 1055; Bundell et al 1988, Eur. J. Biochem. 172, 513; Knighton et al., 1992, Science 258:130-135, http://biochem.vt.edu/courses/-modeling/homology.htn). Computer programs that can be used in homology modeling are QUANTA and the Homology module in the Insight II modeling package distributed by Molecular Simulations Inc, or MODELLER (Rockefeller University, www.iucr.ac.uk/sinris-top/logical/prg-modeller.html).

Once a homology model has been generated it is analyzed to determine its correctness. A computer program available to assist in this analysis is the Protein Health module in QUANTA which provides a variety of tests. Other programs that provide structure analysis along with output include PROCHECK and 3D-Profiler (Luthy R. et al, Nature 356: 83-85, 1992; and Bowie, J. U. et al, Science 253: 164-170, 1991). Once any irregularities have been resolved, the entire structure may be further refined.

Other molecular modeling techniques may also be employed in accordance with this invention. See, e.g., Cohen, N. C. et al, J. Med. Chem., 33, pp. 883-894 (1990). See also, Navix, M. A. and M. A. Marko, Current Opinions in Structural Biology, 2, pp. 202-210 (1992).

Under suitable circumstances, the entire process of solving a crystal structure may be accomplished in an automated fashion by a system such as ELVES (http://ucxray.berkeley.edu/~jamesh/elves/index.html) with little or no user intervention.

(ii) X-Ray Structure

The present invention provides methods for determining some or all of the structural coordinates for amino acids of a dengue virus E protein or other class II E protein, or a complex thereof.

In another aspect, the present invention provides methods for identifying a druggable region of a dengue virus E protein or other class II E protein. For example, one such method includes: (a) obtaining crystals of a dengue virus E protein or other class II E protein or a complex or a fragment thereof such that the three dimensional structure of the crystallized protein can be determined to a resolution of 3.5 Å or better; (b) determining the three dimensional structure of the crystallized polypeptide or fragment using x-ray diffraction; and (c) identifying a druggable region of a dengue virus E protein or other class II E protein based on the three-dimensional structure of the polypeptide or fragment.

A three dimensional structure of a molecule or complex may be described by the set of atoms that best predict the observed diffraction data (that is, which possesses a minimal R value). Files may be created for the structure that defines each atom by its chemical identity, spatial coordinates in three dimensions, root mean squared deviation from the mean observed position and fractional occupancy of the observed position.

Those of skill in the art understand that a set of structure coordinates for an protein, complex or a portion thereof, is a relative set of points that define a shape in three dimensions. Thus, it is possible that an entirely different set of coordinates could define a similar or identical shape. Moreover, slight variations in the individual coordinates may have little affect on overall shape. Such variations in coordinates may be generated because of mathematical manipulations of the structure coordinates. For example, structure coordinates could be manipulated by crystallographic permutations of the structure coordinates, fractionalization of the structure coordinates, integer additions or subtractions to sets of the structure coordinates, inversion of the structure coordinates or any combination of the above. Alternatively, modifications in the crystal structure due to mutations, additions, substitutions, and/or deletions of amino acids, or other changes in any of the components that make up the crystal, could also yield variations in structure coordinates. Such slight variations in the individual coordinates will have little affect on overall shape.

If such variations are within an acceptable standard error as compared to the original coordinates, the resulting three-dimensional shape is considered to be structurally equivalent. It should be noted that slight variations in individual structure coordinates of a dengue virus E protein or other class II E protein or a complex thereof would not be expected to significantly alter the nature of modulators that could associate with a druggable region thereof. Thus, for example, a modulator that bound to the active site of a dengue virus E protein or other class II E protein would also be expected to bind to or interfere with another active site whose structure coordinates define a shape that falls within the acceptable error.

A crystal structure of the present invention may be used to make a structural or computer model of the polypeptide, complex or portion thereof. A model may represent the secondary, tertiary and/or quaternary structure of the polypeptide, complex or portion. The configurations of points in space derived from structure coordinates according to the invention can be visualized as, for example, a holographic image, a stereodiagram, a model or a computer-displayed image, and the invention thus includes such images, diagrams or models.

(iii) Structural Equivalents

Various computational analyses can be used to determine whether a molecule or the active site portion thereof is structurally equivalent with respect to its three-dimensional structure, to all or part of a structure of a dengue virus E protein or other class II E protein or a portion thereof.

For the purpose of this invention, any molecule or complex or portion thereof, that has a root mean square deviation of conserved residue backbone atoms (N, Cα, C, O) of less than about 1.75 Å, when superimposed on the relevant backbone atoms described by the reference structure coordinates of a dengue virus E protein or other class II E protein, is considered "structurally equivalent" to the reference molecule. That is to say, the crystal structures of those portions of the two molecules are substantially identical, within acceptable error. Alternatively, the root mean square deviation may be is less than about 1.50, 1.40, 1.25, 1.0, 0.75, 0.5 or 0.35 Å.

The term "root mean square deviation" is understood in the art and means the square root of the arithmetic mean of the squares of the deviations. It is a way to express the deviation or variation from a trend or object.

In another aspect, the present invention provides a scalable three-dimensional configuration of points, at least a portion of said points, and preferably all of said points, derived from structural coordinates of at least a portion of a dengue virus E protein or other class II E protein and having a root mean square deviation from the structure coordinates of the dengue virus E protein or other class II E protein of less than 1.50, 1.40, 1.25, 1.0, 0.75, 0.5 or 0.35 Å. In certain embodiments, the portion of a dengue virus E protein or other class II E protein is 25%, 33%, 50%, 66%, 75%, 85%, 90% or 95% or more of the amino acid residues contained in the polypeptide.

In another aspect, the present invention provides a molecule or complex including a druggable region of a dengue virus E protein or other class II E protein, the druggable region being defined by a set of points having a root mean square deviation of less than about 1.75 Å from the structural coordinates for points representing (a) the backbone atoms of the amino acids contained in a druggable region of a dengue virus E protein or other class II E protein, (b) the side chain atoms (and optionally the Cα atoms) of the amino acids contained in such druggable region, or (c) all the atoms of the amino acids contained in such druggable region. In certain embodiments, only a portion of the amino acids of a druggable region may be included in the set of points, such as 25%, 33%, 50%, 66%, 75%, 85%, 90% or 95% or more of the amino acid residues contained in the druggable region. In certain embodiments, the root mean square deviation may be less than 1.50, 1.40, 1.25, 1.0, 0.75, 0.5, or 0.35 Å. In still other embodiments, instead of a druggable region, a stable domain, fragment or structural motif is used in place of a druggable region.

(iv) Machine Displays and Machine Readable Storage Media

The invention provides a machine-readable storage medium including a data storage material encoded with machine readable data which, when using a machine programmed with instructions for using said data, displays a graphical three-dimensional representation of any of the molecules or complexes, or portions thereof, of this invention. In another embodiment, the graphical three-dimensional representation of such molecule, complex or portion thereof includes the root mean square deviation of certain atoms of such molecule by a specified amount, such as the backbone atoms by less than 0.8 Å. In another embodiment, a structural equivalent of such molecule, complex, or portion thereof, may be displayed. In another embodiment, the portion may include a druggable region of the dengue virus E protein or other class II E protein.

According to one embodiment, the invention provides a computer for determining at least a portion of the structure coordinates corresponding to x-ray diffraction data obtained from a molecule or complex, wherein said computer includes: (a) a machine-readable data storage medium comprising a data storage material encoded with machine-readable data, wherein said data comprises at least a portion of the structural coordinates of a dengue virus E protein or other class II E protein; (b) a machine-readable data storage medium comprising a data storage material encoded with machine-readable data, wherein said data comprises x-ray diffraction data from said molecule or complex; (c) a working memory for storing instructions for processing said machine-readable data of (a) and (b); (d) a central-processing unit coupled to said working memory and to said machine-readable data storage medium of (a) and (b) for performing a Fourier transform of the machine readable data of (a) and for processing said machine readable data of (b) into structure coordinates; and (e) a display coupled to said central-processing unit for displaying said structure coordinates of said molecule or complex. In certain embodiments, the structural coordinates displayed are structurally equivalent to the structural coordinates of a dengue virus E protein or other class II E protein.

In an alternative embodiment, the machine-readable data storage medium includes a data storage material encoded with a first set of machine readable data which includes the Fourier transform of the structure coordinates of a dengue virus E protein or other class II E protein or a portion thereof, and which, when using a machine programmed with instructions for using said data, can be combined with a second set of machine readable data including the x-ray diffraction pattern of a molecule or complex to determine at least a portion of the structure coordinates corresponding to the second set of machine readable data.

For example, a system for reading a data storage medium may include a computer including a central processing unit ("CPU"), a working memory which may be, e.g., RAM (random access memory) or "core" memory, mass storage memory (such as one or more disk drives or CD-ROM drives), one or more display devices (e.g., cathode-ray tube ("CRT") displays, light emitting diode ("LED") displays, liquid crystal displays ("LCDs"), electroluminescent displays, vacuum fluorescent displays, field emission displays ("FEDs"), plasma displays, projection panels, etc.), one or more user input devices (e.g., keyboards, microphones, mice, touch screens, etc.), one or more input lines, and one or more output lines, all of which are interconnected by a conventional bidirectional system bus. The system may be a stand-alone computer, or may be networked (e.g., through local area networks, wide area networks, intranets, extranets, or the internet) to other systems (e.g., computers, hosts, servers, etc.). The system may also include additional computer controlled devices such as consumer electronics and appliances.

Input hardware may be coupled to the computer by input lines and may be implemented in a variety of ways. Machine-readable data of this invention may be inputted via the use of a modem or modems connected by a telephone line or dedicated data line. Alternatively or additionally, the input hardware may include CD-ROM drives or disk drives. In conjunction with a display terminal, a keyboard may also be used as an input device.

Output hardware may be coupled to the computer by output lines and may similarly be implemented by conventional devices. By way of example, the output hardware may include a display device for displaying a graphical representation of an active site of this invention using a program such as QUANTA as described herein. Output hardware might also include a printer, so that hard copy output may be produced, or a disk drive, to store system output for later use.

In operation, a CPU coordinates the use of the various input and output devices, coordinates data accesses from mass storage devices, accesses to and from working memory, and determines the sequence of data processing steps. A number of programs may be used to process the machine-readable data of this invention. Such programs are discussed in reference to the computational methods of drug discovery as described herein. References to components of the hardware system are included as appropriate throughout the following description of the data storage medium.

Machine-readable storage devices useful in the present invention include, but are not limited to, magnetic devices, electrical devices, optical devices, and combinations thereof. Examples of such data storage devices include, but are not limited to, hard disk devices, CD devices, digital video disk devices, floppy disk devices, removable hard disk devices, magneto-optic disk devices, magnetic tape devices, flash memory devices, bubble memory devices, holographic storage devices, and any other mass storage peripheral device. It should be understood that these storage devices include necessary hardware (e.g., drives, controllers, power supplies, etc.) as well as any necessary media (e.g., disks, flash cards, etc.) to enable the storage of data.

In one embodiment, the present invention contemplates a computer readable storage medium comprising structural data, wherein the data include the identity and three-dimensional coordinates of a dengue virus E protein or other class II E protein or portion thereof. In another aspect, the present invention contemplates a database comprising the identity and three-dimensional coordinates of a dengue virus E protein or other class II E protein or a portion thereof. Alternatively, the present invention contemplates a database comprising a portion or all of the atomic coordinates of a dengue virus E protein or other class II E protein or portion thereof.

(v) Structurally Similar Molecules and Complexes

Structural coordinates for a dengue virus E protein or other class II E protein can be used to aid in obtaining structural information about another molecule or complex. This method of the invention allows determination of at least a portion of the three-dimensional structure of molecules or molecular complexes which contain one or more structural features that are similar to structural features of a dengue virus E protein or other class II E protein. Similar structural features can include, for example, regions of amino acid identity, conserved active site or binding site motifs, and similarly arranged secondary structural elements (e.g., α helices and β sheets). Many of the methods described above for determining the structure of a dengue virus E protein or other class II E protein may be used for this purpose as well.

For the present invention, a "structural homolog" is a polypeptide that contains one or more amino acid substitutions, deletions, additions, or rearrangements with respect to a subject amino acid sequence or other dengue virus E protein or other class II E protein, but that, when folded into its native conformation, exhibits or is reasonably expected to exhibit at least a portion of the tertiary (three-dimensional) structure of the polypeptide encoded by the related subject amino acid sequence or such other dengue virus E protein or other class II E protein. For example, structurally homologous molecules can contain deletions or additions of one or more contiguous or noncontiguous amino acids, such as a loop or a domain. Structurally homologous molecules also include modified polypeptide molecules that have been chemically or enzymatically derivatized at one or more constituent amino acids, including side chain modifications, backbone modifications, and N- and C-terminal modifications including acetylation, hydroxylation, methylation, amidation, and the attachment of carbohydrate or lipid moieties, cofactors, and the like.

By using molecular replacement, all or part of the structure coordinates of a dengue virus E protein or other class II E protein can be used to determine the structure of a crystallized molecule or complex whose structure is unknown more quickly and efficiently than attempting to determine such information ab initio. For example, in one embodiment this invention provides a method of utilizing molecular replacement to obtain structural information about a molecule or complex whose structure is unknown including: (a) crystallizing the molecule or complex of unknown structure; (b) generating an x-ray diffraction pattern from said crystallized molecule or complex; and (c) applying at least a portion of the structure coordinates for a dengue virus E protein or other class II E protein to the x-ray diffraction pattern to generate a three-dimensional electron density map of the molecule or complex whose structure is unknown.

In another aspect, the present invention provides a method for generating a preliminary model of a molecule or complex whose structure coordinates are unknown, by orienting and positioning the relevant portion of a dengue virus E protein or other class II E protein within the unit cell of the crystal of the unknown molecule or complex so as best to account for the observed x-ray diffraction pattern of the crystal of the molecule or complex whose structure is unknown.

Structural information about a portion of any crystallized molecule or complex that is sufficiently structurally similar to a portion of a dengue virus E protein or other class II E protein may be resolved by this method. In addition to a molecule that shares one or more structural features with a dengue virus E protein or other class II E protein, a molecule that has similar bioactivity, such as the same catalytic activity, substrate specificity or ligand binding activity as a dengue virus E protein or other class II E protein, may also be sufficiently structurally similar to a dengue virus E protein or other class II E protein to permit use of the structure coordinates for a dengue virus E protein or other class II E protein to solve its crystal structure.

In another aspect, the method of molecular replacement is utilized to obtain structural information about a complex containing a dengue virus E protein or other class II E protein, such as a complex between a modulator and a dengue virus E protein or other class II E protein (or a domain, fragment, ortholog, homolog etc. thereof). In certain instances, the complex includes a dengue virus E protein or other class II E protein (or a domain, fragment, ortholog, homolog etc. thereof) co-complexed with a modulator. In one embodiment of the invention, the dengue virus E protein or other class II E protein is complexed with β-OG or other detergent molecule. In yet another embodiment, the complex is a dengue virus E protein or other class II E protein trimer. In certain embodiments, the trimer may additionally comprise a modulator. For example, in one embodiment, the present invention contemplates a method for making a crystallized complex comprising a dengue virus E protein or other class II E protein, or a fragment thereof, and a compound, the method comprising: (a) crystallizing a dengue virus E protein or other class II E protein such that the crystals will diffract x-rays to a resolution of 3.5 Å or better; and (b) soaking the crystal in a solution comprising the compound, thereby producing a crystallized complex comprising the polypeptide and the compound.

Using homology modeling, a computer model of a structural homolog or other polypeptide can be built or refined without crystallizing the molecule. For example, in another aspect, the present invention provides a computer-assisted method for homology modeling a structural homolog of a dengue virus E protein or other class II E protein including: aligning the amino acid sequence of a known or suspected structural homolog with the amino acid sequence of a dengue virus E protein or other class II E protein and incorporating the sequence of the homolog into a model of a dengue virus E protein or other class II E protein derived from atomic structure coordinates to yield a preliminary model of the homolog; subjecting the preliminary model to energy minimization to yield an energy minimized model; remodeling regions of the energy minimized model where stereochemistry restraints are violated to yield a final model of the homolog.

In another embodiment, the present invention contemplates a method for determining the crystal structure of a homolog of a polypeptide encoded by a subject amino acid sequence, or equivalent thereof, the method comprising: (a) providing the three dimensional structure of a crystallized polypeptide of a subject amino acid sequence, or a fragment thereof; (b) obtaining crystals of a homologous polypeptide comprising an amino acid sequence that is at least 80% identical to the subject amino acid sequence such that the three dimensional structure of the crystallized homologous polypeptide may be determined to a resolution of 3.5 Å or better; and (c) determining the three dimensional structure of the crystallized homologous polypeptide by x-ray crystallography based on the atomic coordinates of the three dimensional structure provided in step (a). In certain instances of the foregoing method, the atomic coordinates for the homologous polypeptide have a root mean square deviation from the backbone atoms of the polypeptide encoded by the applicable subject amino acid sequence, or a fragment thereof, of not more than 1.5 Å for all backbone atoms shared in common with the homologous polypeptide and the such encoded polypeptide, or a fragment thereof.

(vi) NMR Analysis Using X-Ray Structural Data

In another aspect, the structural coordinates of a known crystal structure may be applied to nuclear magnetic resonance data to determine the three dimensional structures of polypeptides with uncharacterized or incompletely characterized structure. (See for example, Wuthrich, 1986, John Wiley and Sons, New York: 176-199; Pflugrath et al., 1986, J. Molecular Biology 189: 383-386; Kline et al., 1986 J. Molecular Biology 189:377-382). While the secondary structure of a polypeptide may often be determined by NMR data, the spatial connections between individual pieces of secondary structure are not as readily determined. The structural coordinates of a polypeptide defined by x-ray crystallography can guide the NMR spectroscopist to an understanding of the spatial interactions between secondary structural elements in a polypeptide of related structure. Information on spatial interactions between secondary structural elements can greatly simplify NOE data from two-dimensional NMR experiments. In addition, applying the structural coordinates after the determination of secondary structure by NMR techniques simplifies the assignment of NOE's relating to particular amino acids in the polypeptide sequence.

In an embodiment, the invention relates to a method of determining three dimensional structures of polypeptides with unknown structures, by applying the structural coordinates of a crystal of the present invention to nuclear magnetic resonance data of the unknown structure. This method comprises the steps of: (a) determining the secondary structure of an unknown structure using NMR data; and (b) simplifying the assignment of through-space interactions of amino acids. The term "through-space interactions" defines the orientation of the secondary structural elements in the three dimensional structure and the distances between amino acids from different portions of the amino acid sequence. The term "assignment" defines a method of analyzing NMR data and identifying which amino acids give rise to signals in the NMR spectrum.

For all of this section on x-ray crystallography, see also Brooks et al. (1983) *J Comput Chem* 4:187-217; Weiner et al (1981) *J. Comput. Chem.* 106: 765; Eisenfield et al. (1991) *Am J Physiol* 261:C376-386; Lybrand (1991) *J Pharm Belg* 46:49-54; Froimowitz (1990) *Biotechniques* 8:640-644; Burbam et al. (1990) *Proteins* 7:99-111; Pedersen (1985) *Environ Health Perspect* 61:185-190; and Kini et al. (1991) *J Biomol Struct Dyn* 9:475-488; Ryckaert et al. (1977) *J Comput Phys* 23:327; Van Gunsteren et al. (1977) *Mol Phys* 34:1311; Anderson (1983) *J Comput Phys* 52:24; J. Mol. Biol. 48: 442-453, 1970; Dayhoff et al., Meth. Enzymol. 91: 524-545, 1983; Henikoff and Henikoff, Proc. Nat. Acad. Sci. USA 89: 10915-10919, 1992; J. Mol. Biol. 233: 716-738, 1993; Methods in Enzymology, Volume 276, Macromolecular crystallography, Part A, ISBN 0-12-182177-3 and Volume 277, Macromolecular crystallography, Part B, ISBN 0-12-182178-1, Eds. Charles W. Carter, Jr. and Robert M. Sweet (1997), Academic Press, San Diego; Pfuetzner, et al., J. Biol. Chem. 272: 430-434 (1997).

H.2. Analysis of Proteins by Nuclear Magnetic Resonance (NMR)

NMR may be used to characterize the structure of a polypeptide in accordance with the methods of the invention. In particular, NMR can be used, for example, to determine the three dimensional structure, the conformational state, the aggregation level, the state of protein folding/unfolding or the dynamic properties of a polypeptide. For example, the present invention contemplates a method for determining three dimensional structure information of a dengue virus E protein or other class II E protein, the method comprising: (a) generating a purified isotopically labeled dengue virus E protein or other class II E protein; and (b) subjecting the polypeptide to NMR spectroscopic analysis, thereby determining information about its three dimensional structure.

Interaction between a polypeptide and another molecule can also be monitored using NMR. Thus, the invention encompasses methods for detecting, designing and characterizing interactions between a polypeptide and another molecule, including polypeptides, nucleic acids and small molecules, utilizing NMR techniques. For example, the present invention contemplates a method for determining three dimensional structure information of a dengue virus E protein or other class II E protein, or a fragment thereof, while the polypeptide is complexed with another molecule, the method comprising: (a) generating a purified isotopically labeled dengue virus E protein or other class II E protein, or a fragment thereof; (b) forming a complex between the polypeptide and the other molecule; and (c) subjecting the complex to NMR spectroscopic analysis, thereby determining information about the three dimensional structure of the polypeptide. In another aspect, the present invention contemplates a method for identifying compounds that bind to a dengue virus E protein or other class II E protein, or a fragment thereof, the method comprising: (a) generating a first NMR spectrum of an isotopically labeled dengue virus E protein or other class II E protein, or a fragment thereof; (b) exposing the polypeptide to one or more chemical compounds; (c) generating a second NMR spectrum of the polypeptide which has been exposed to one or more chemical compounds; and (d) comparing the first and second spectra to determine differences between the first and the second spectra, wherein the differences are indicative of one or more compounds that have bound to the polypeptide.

Briefly, the NMR technique involves placing the material to be examined (usually in a suitable solvent) in a powerful magnetic field and irradiating it with radio frequency (rf) electromagnetic radiation. The nuclei of the various atoms will align themselves with the magnetic field until energized by the rf radiation. They then absorb this resonant energy and re-radiate it at a frequency dependent on i) the type of nucleus and ii) its atomic environment. Moreover, resonant energy may be passed from one nucleus to another, either through bonds or through three-dimensional space, thus giving information about the environment of a particular nucleus and nuclei in its vicinity.

However, it is important to recognize that not all nuclei are NMR active. Indeed, not all isotopes of the same element are active. For example, whereas "ordinary" hydrogen, $^{1}H$, is NMR active, heavy hydrogen (deuterium), $^{2}H$, is not active in the same way. Thus, any material that normally contains $^{1}H$ hydrogen may be rendered "invisible" in the hydrogen NMR spectrum by replacing all or almost all the $^{1}H$ hydrogens with $^{2}H$. It is for this reason that NMR spectroscopic analyses of water-soluble materials frequently are performed in $^{2}H_2O$ (or deuterium) to eliminate the water signal.

Conversely, "ordinary" carbon, $^{12}C$, is NMR inactive whereas the stable isotope, $^{13}C$, present to about 1% of total carbon in nature, is active. Similarly, while "ordinary" nitrogen, $^{14}N$, is NMR active, it has undesirable properties for NMR and resonates at a different frequency from the stable isotope $^{15}N$, present to about 0.4% of total nitrogen in nature.

By labeling proteins with $^{15}N$ and $^{15}N/^{13}C$, it is possible to conduct analytical NMR of macromolecules with weights of 15 kD and 40 kD, respectively. More recently, partial deuteration of the protein in addition to $^{13}C$- and $^{15}N$-labeling has increased the possible weight of proteins and protein complexes for NMR analysis still further, to approximately 60-70 kD. See Shan et al., J. Am. Chem. Soc., 118:6570-6579 (1996); L. E. Kay, Methods Enzymol., 339:174-203 (2001); and K. H. Gardner & L. E. Kay, Annu Rev Biophys Biomol Struct., 27:357-406 (1998); and references cited therein.

Isotopic substitution may be accomplished by growing a bacterium or yeast or other type of cultured cells, transformed by genetic engineering to produce the protein of choice, in a growth medium containing $^{13}C$-, $^{15}N$- and/or $^{2}H$-labeled substrates. In certain instances, bacterial growth media consists of $^{13}C$-labeled glucose and/or $^{15}N$-labeled ammonium salts dissolved in $D_2O$ where necessary. Kay, L. et al., Science, 249:411 (1990) and references therein and Bax, A., J. Am. Chem. Soc., 115, 4369 (1993). More recently, isotopically labeled media especially adapted for the labeling of bacterially produced macromolecules have been described. See U.S. Pat. No. 5,324,658.

The goal of these methods has been to achieve universal and/or random isotopic enrichment of all of the amino acids of the protein. By contrast, other methods allow only certain residues to be relatively enriched in $^{1}H$, $^{2}H$, $^{13}C$ and $^{15}N$. For example, Kay et al., J. Mol. Biol., 263, 627-636 (1996) and Kay et al., J. Am. Chem. Soc., 119, 7599-7600 (1997) have described methods whereby isoleucine, alanine, valine and leucine residues in a protein may be labeled with $^{2}H$, $^{13}C$ and $^{15}N$, and may be specifically labeled with $^{1}H$ at the terminal methyl position. In this way, study of the proton-proton interactions between some amino acids may be facilitated. Similarly, a cell-free system has been described by Yokoyama et al., J. Biomol. NMR, 6(2), 129-134 (1995), wherein a transcription-translation system derived from *E. coli* was used to express human Ha-Ras protein incorporating $^{15}N$ into serine and/or aspartic acid.

Techniques for producing isotopically labeled proteins and macromolecules, such as glycoproteins, in mammalian or insect cells have been described. See U.S. Pat. Nos. 5,393,669 and 5,627,044; Weller, C. T., Biochem., 35, 8815-23 (1996) and Lustbader, J. W., J. Biomol. NMR, 7, 295-304 (1996). Other methods for producing polypeptides and other molecules with labels appropriate for NMR are known in the art.

The present invention contemplates using a variety of solvents which are appropriate for NMR. For $^{1}H$ NMR, a deuterium lock solvent may be used. Exemplary deuterium lock solvents include acetone ($CD_3COCD_3$), chloroform ($CDCl_3$), dichloro methane ($CD_2Cl_2$), methylnitrile ($CD_3CN$), benzene ($C_6D_6$), water ($D_2O$), diethylether ($(CD_3CD_2)_2O$), dimethylether ($(CD_3)_2O$), N,N-dimethylformamide ($(CD_3)_2NCDO$), dimethyl sulfoxide ($CD_3SOCD_3$), ethanol ($CD_3CD_2OD$), methanol ($CD_3OD$), tetrahydrofuran ($C_4D_8O$), toluene ($C_6D_5CD_3$), pyridine ($C_5D_5N$) and cyclohexane ($C_6H_{12}$). For example, the present invention contemplates a composition comprising a dengue virus E protein or other class II E protein and a deuterium lock solvent.

The 2-dimensional $^{1}H$—$^{15}N$ HSQC (Heteronuclear Single Quantum Correlation) spectrum provides a diagnostic fingerprint of conformational state, aggregation level, state of protein folding, and dynamic properties of a polypeptide (Yee et al, PNAS 99, 1825-30 (2002)). Polypeptides in aqueous solution usually populate an ensemble of 3-dimensional structures which can be determined by NMR. When the polypeptide is a stable globular protein or domain of a protein, then the ensemble of solution structures is one of very closely related conformations. In this case, one peak is expected for each non-proline residue with a dispersion of resonance frequencies with roughly equal intensity. Additional pairs of peaks from side-chain $NH_2$ groups are also often observed, and correspond to the approximate number of Gln and Asn residues in the protein. This type of HSQC spectra usually indicates that the protein is amenable to structure determination by NMR methods.

If the HSQC spectrum shows well-dispersed peaks but there are either too few or too many in number, and/or the peak intensities differ throughout the spectrum, then the protein likely does not exist in a single globular conformation. Such spectral features are indicative of conformational heterogeneity with slow or nonexistent inter-conversion between states (too many peaks) or the presence of dynamic processes on an intermediate timescale that can broaden and obscure the NMR signals. Proteins with this type of spectrum can sometimes be stabilized into a single conformation by changing either the protein construct, the solution conditions, temperature or by binding of another molecule.

The $^1H$—$^{15}N$ HSQC can also indicate whether a protein has formed large nonspecific aggregates or has dynamic properties. Alternatively, proteins that are largely unfolded, e.g., having very little regular secondary structure, result in $^1H$—$^{15}N$ HSQC spectra in which the peaks are all very narrow and intense, but have very little spectral dispersion in the $^{15}N$-dimension. This reflects the fact that many or most of the amide groups of amino acids in unfolded polypeptides are solvent exposed and experience similar chemical environments resulting in similar $^1H$ chemical shifts.

The use of the $^1H$—$^{15}N$ HSQC, can thus allow the rapid characterization of the conformational state, aggregation level, state of protein folding, and dynamic properties of a polypeptide. Additionally, other 2D spectra such as $^1H$—$^{13}C$ HSQC, or HNCO spectra can also be used in a similar manner. Further use of the $^1$-$^{15}N$ HSQC combined with relaxation measurements can reveal the molecular rotational correlation time and dynamic properties of polypeptides. The rotational correlation time is proportional to size of the protein and therefore can reveal if it forms specific homo-oligomers such as homodimers, homotetramers, etc.

The structure of stable globular proteins can be determined through a series of well-described procedures. For a general review of structure determination of globular proteins in solution by NMR spectroscopy, see Wüthrich, Science 243: 45-50 (1989). See also, Billeter et al., J. Mol. Biol. 155: 321-346 (1982). Current methods for structure determination usually require the complete or nearly complete sequence-specific assignment of $^1H$-resonance frequencies of the protein and subsequent identification of approximate inter-hydrogen distances (from nuclear Overhauser effect (NOE) spectra) for use in restrained molecular dynamics calculations of the protein conformation. One approach for the analysis of NMR resonance assignments was first outlined by Wüthrich, Wagner and co-workers (Wüthrich, "NMR or proteins and nucleic acids" Wiley, New York, N.Y. (1986); Wüthrich, Science 243: 45-50 (1989); Billeter et al., J. Mol. Biol. 155: 321-346 (1982)). Newer methods for determining the structures of globular proteins include the use of residual dipolar coupling restraints (Tian et al., J Am Chem. Soc. 2001 Nov. 28; 123 (47):11791-6; Bax et al, Methods Enzymol. 2001; 339:127-74) and empirically derived conformational restraints (Zweckstetter & Bax, J Am Chem. Soc. 2001 Sep. 26; 123 (38):9490-1). It has also been shown that it may be possible to determine structures of globular proteins using only un-assigned NOE measurements. NMR may also be used to determine ensembles of many inter-converting, unfolded conformations (Choy and Forman-Kay, J Mol Biol. 2001 May 18; 308(5):1011-32).

NMR analysis of a polypeptide in the presence and absence of a test compound (e.g., a polypeptide, nucleic acid or small molecule) may be used to characterize interactions between a polypeptide and another molecule. Because the $^1H$—$^{15}N$ HSQC spectrum and other simple 2D NMR experiments can be obtained very quickly (on the order of minutes depending on protein concentration and NMR instrumentation), they are very useful for rapidly testing whether a polypeptide is able to bind to another molecule. Changes in the resonance frequency (in one or both dimensions) of one or more peaks in the HSQC spectrum indicate an interaction with another molecule. Often only a subset of the peaks will have changes in resonance frequency upon binding to anther molecule, allowing one to map onto the structure those residues directly involved in the interaction or involved in conformational changes as a result of the interaction. If the interacting molecule is relatively large (protein or nucleic acid) the peak widths will also broaden due to the increased rotational correlation time of the complex. In some cases the peaks involved in the interaction may actually disappear from the NMR spectrum if the interacting molecule is in intermediate exchange on the NMR timescale (i.e., exchanging on and off the polypeptide at a frequency that is similar to the resonance frequency of the monitored nuclei).

To facilitate the acquisition of NMR data on a large number of compounds (e.g., a library of synthetic or naturally-occurring small organic compounds), a sample changer may be employed. Using the sample changer, a larger number of samples, numbering 60 or more, may be run unattended. To facilitate processing of the NMR data, computer programs are used to transfer and automatically process the multiple one-dimensional NMR data.

In one embodiment, the invention provides a screening method for identifying small molecules capable of interacting with a dengue virus E protein or other class II E protein. In one example, the screening process begins with the generation or acquisition of either a $T_2$-filtered or a diffusion-filtered one-dimensional proton spectrum of the compound or mixture of compounds. Means for generating $T_2$-filtered or diffusion-filtered one-dimensional proton spectra are well known in the art (see, e.g., S. Meiboom and D. Gill, Rev. Sci. Instrum. 29:688 (1958), S. J. Gibbs and C. S. Johnson, Jr. J. Main. Reson. 93:395-402 (1991) and A. S. Altieri, et al. J. Am. Chem. Soc. 117: 7566-7567 (1995)).

Following acquisition of the first spectrum for the molecules, the $^{15}N$- or $^{13}C$-labeled polypeptide is exposed to one or more molecules. Where more than one test compound is to be tested simultaneously, it is preferred to use a library of compounds such as a plurality of small molecules. Such molecules are typically dissolved in perdeuterated dimethylsulfoxide. The compounds in the library may be purchased from vendors or created according to desired needs.

Individual compounds may be selected inter alia on the basis of size and molecular diversity for maximizing the possibility of discovering compounds that interact with widely diverse binding sites of a subject amino acid sequence or other polypeptides of the invention.

The NMR screening process of the present invention utilizes a range of test compound concentrations, e.g., from about 0.05 to about 1.0 mM. At those exemplary concentrations, compounds which are acidic or basic may significantly change the pH of buffered protein solutions. Chemical shifts are sensitive to pH changes as well as direct binding interactions, and false-positive chemical shift changes, which are not the result of test compound binding but of changes in pH, may therefore be observed. It may therefore be necessary to ensure that the pH of the buffered solution does not change upon addition of the test compound.

Following exposure of the test compounds to a polypeptide (e.g., the target molecule for the experiment) a second one-dimensional $T_2$- or diffusion-filtered spectrum is generated. For the $T_2$-filtered approach, that second spectrum is generated in the same manner as set forth above. The first and second spectra are then compared to determine whether there are any differences between the two spectra. Differences in the one-dimensional $T_2$-filtered spectra indicate that the compound is binding to, or otherwise interacting with, the target molecule. Those differences are determined using standard procedures well known in the art. For the diffusion-filtered method, the second spectrum is generated by looking at the spectral differences between low and high gradient strengths—thus selecting for those compounds whose diffusion rates are comparable to that observed in the absence of target molecule.

To discover additional molecules that bind to the protein, molecules are selected for testing based on the structure/activity relationships from the initial screen and/or structural information on the initial leads when bound to the protein. By way of example, the initial screening may result in the identification of compounds, all of which contain an aromatic ring. The second round of screening would then use other aromatic molecules as the test compounds.

In another embodiment, the methods of the invention utilize a process for detecting the binding of one ligand to a polypeptide in the presence of a second ligand. In accordance with this embodiment, a polypeptide is bound to the second ligand before exposing the polypeptide to the test compounds.

For more information on NMR methods encompassed by the present invention, see also: U.S. Pat. Nos. 5,668,734; 6,194,179; 6,162,627; 6,043,024; 5,817,474; 5,891,642; 5,989,827; 5,891,643; 6,077,682; WO 00/05414; WO 99/22019; Cavanagh, et al., Protein NMR Spectroscopy, Principles and Practice, 1996, Academic Press; Clore, et al., NMR of Proteins. In Topics in Molecular and Structural Biology, 1993, S. Neidle, Fuller, W., and Cohen, J. S., eds., Macmillan Press, Ltd., London; and Christendat et al., Nature Structural Biology 7: 903-909 (2000).

EXEMPLIFICATION

The invention having been generally described, may be more readily understood by reference to the following examples, which are included merely for purposes of illustration of certain aspects and embodiments of the present invention, and are not intended to limit the invention in any way.

EXAMPLE 1

Determination of the Pre-Fusion Structure of E Protein from Dengue Virus Type S1

A. Expression, Purification and Crystallization of E Protein from Dengue Virus Type 2 S1

E protein from dengue virus type 2 S1 strain (Hahn et al., 1988) was supplied by Hawaii Biotechnology Group, Inc. (Aiea, Hi.). The construct that encoded the E protein sequence (SEQ ID NO 2) spans nucleotides 937-2118 of GenBank Accession Number M19197 and is described in detail in Hahn, Y. S. et al (1988), Virology 162, p 167-180. The primers that were used to amplify the dengue sE sequence by PCR:primer D2E937p2 5'-cttctagatctcgagtacccgggacc ATG CGC TGC ATA GGA ATA TC-3' (SEQ ID NO:5) and primer D2E2121m 5'-gctctagagtcga cta tta TCC TTT CTT GAA CCA G-3' (SEQ ID NO:6). Nucleotides corresponding to dengue cDNA are in upper case; non-dengue sequence is in lower case. The protein was expressed in *Drosophila melanogaster* Schneider 2 cells (ATCC, Rockville, Md.) from a pMtt vector (SmithKline Beecham) containing the dengue 2 prM and E genes (nucleotides 1-1185) as described by Ivy et al. (1997). The resulting prM-E preprotein was processed during secretion to yield soluble E protein, which was purified from the cell culture medium by immunoaffinity chromatography (Cuzzubbo et al., 2001).

Crystals grew from a 10 g/l solution at 4° C. by hanging drop vapor diffusion in 11% PEG 8000, 1 M sodium formate, 20% glycerol and 0.1 M HEPES pH 8. The addition of 0.5% n-octyl-β-D-glucoside prior to crystallization significantly improved the abundance and diffraction limit of the crystals. Dimensions of the primitive hexagonal cell were approximately a=b=81 Å, c=287 Å, with two molecules per asymmetric unit. An additional primitive hexagonal crystal form was observed, with cell dimensions a=b=75 Å, c=145 Å, and one molecule per asymmetric unit.

B. Data Collection and Processing

Crystals were derivatized by soaking in mother liquor containing 0.5 mM $K_2PtCl_4$, 0.5 mM $Yb_2(SO_4)_3$, 0.5 mM $KAu(CN)_2$, or 10 mM $Me_3PbAc$ for 24 h. Datasets were collected at 100 K on beamlines A1 and F1 of the Cornell High Energy Synchrotron Source (Cornell University), except the 'Native 1' dataset (see Table 1), which was collected on beamline ID-19 at the Advanced Photon Source (Argonne National Laboratory). The data were processed with HKL (Otwinowski and Minor, 1997). Table 1 lists the crystallographic data statistics for the structure of dengue virus E protein in complex with n-octyl-β-D-glucoside.

TABLE 1

| CRYSTALLOGRAPHIC DATA STATISTICS. β-OG, N-OCTYL-β-D-GLUCOSIDE | | | | | | | | |
|---|---|---|---|---|---|---|---|---|
| Data collection and structure solution | | | | | | | | |
| Dataset | Native1 | Native2 | $Me_3PbAc$ | $K_2PtCl_4$ | $YbSO_4$ | AuCN | Native3 | Native4 |
| Conc. βOG (mM) | 17 | 17 | 17 | 17 | 17 | 17 | 0 | 0 |
| Resolution range (Å) | 50-2.4 | 30-2.47 | 30-2.8 | 30-2.8 | 30-2.8 | 30-2.8 | 50-2.75 | 50-3.0 |
| Cell edges a(=b)/c | 81.6/287.4 | 81.2/286.6 | 81.3/286.8 | 81.3/286.9 | 81.1/286.5 | 81.2/285.5 | 81.5/288.6 | 74.6/144.7 |
| % completeness[1] | 97 (74) | 92 (45) | 99 (98) | 97 (88) | 99 (97) | 97 (99) | 90 (49) | 96 (82) |
| I/σ(I)[1] | 26.2 (3.3) | 15.1 (1.8) | 17.3 (4.0) | 17.8 (4.7) | 15.5 (2.7) | 11.9 (6.2) | 21.7 (2.5) | 13.6 (2.0) |
| $R_{merge}$[1,2] (%) | 6.9 (28.9) | 6.1 (26.8) | 6.0 (27.4) | 8.2 (31.1) | 7.4 (39.2) | 5.3 (7.7) | 7.9 (40.9) | 8.4 (47.6) |
| Number of sites | | | 2 | 1 | 2 | 2 | | |
| Phasing power[3] (centric/acentric) (Sharp) | | | 0.85/1.3 | 0.43/0.52 | 0.25/0.49 | 0.36/0.54 | | |
| Phasing power[3] (anomalous) (Sharp) | | | 0.57 | 0.67 | 0.27 | 0.40 | | |
| FOM[4] centric (CNS/Sharp) | | 0.68/0.24 | | | | | | |
| FOM[4] acentric (CNS/Sharp) | | 0.34/0.24 | | | | | | |

TABLE 1-continued

CRYSTALLOGRAPHIC DATA STATISTICS. β-OG, N-OCTYL-β-D-GLUCOSIDE

Model building and refinement

| | Native1 | Native3 |
|---|---|---|
| Resolution range | 50-2.4 | 50-2.75 |
| Unique reflections | 44,435 | 24,851 |
| $R_{cryst}^{1,5}$ | 0.2633 | 0.2610 |
| $R_{free}^{1,6}$ | 0.2938 | 0.2964 |
| Average B-factor (Å$^2$) | | |
| Protein (chain A/B) | 88.7/64.5 | 79.1/72.8 |
| Solvent | 84.8 | 78.9 |
| R.m.s. deviation | | |
| Bond length (Å) | 0.011 | 0.009 |
| Bond angle (°) | 1.706 | 1.415 |
| Bonded B-factor (Å$^2$) | | |
| Main chain | 4.37 | 3.30 |
| Side chain | 7.39 | 5.87 |
| Ramachandran plot (%) | | |
| Favored | 82.3 | 73.2 |
| Allowed | 17.0 | 26.8 |
| Generous | 0.7 | 0.0 |
| Disallowed | 0 | 0 |

[1] Number in parentheses is for the highest resolution shell.
[2] $R_{merge} = \Sigma_{hkl}|I - <I>|/\Sigma_{hkl}\Sigma_i(I)$
[3] Phasing power = (FH/Lack of closure)
[4] $FOM = ((\cos\phi)^2 + (\sin\phi)^2)^{1/2}$
[5] $R_{cryst} = \Sigma_{hkl}||F_{obs}| - |<F_{calc}>||/\Sigma_{hkl}|F_{obs}|$
[6] $R_{free} = R_{cryst}$ using 5% of $F_{obs}$ sequestered before refinement C. Structure Determination and Refinement The pronounced anisotropy of the datasets was corrected by scaling each dataset anisotropically to a calculated dataset obtained from an arbitrary set of atomic coordinates. The datasets were scaled to the most isomorphous native dataset, 'Native2' (Table 1), and isomorphous difference Patterson were calculated with SOLVE (Terwilliger and Berendzen, 1999). Two initial heavy atom sites were identified using the lead derivative. Additional sites were located in the three other derivative datasets using cross-difference Fourier maps. Initial phases were optimized by refining the heavy atom parameters against maximum likelihood targets with SHARP (La Fortelle and Bricogne, 1997). Phases were improved by solvent flattening and two-fold non-crystallographic symmetry (NCS) averaging with DM (Collaborative Computational Project, 1994) and RESOLVE (Terwilliger, 1999). The solvent content was assumed to be 43%. The space group was determined as P3$_1$21, based on interpretable features in density-modified maps. An initial model was built into the maps with O (Jones et al., 1991). The atomic coordinates were refined against the best native dataset, 'Native1' (Table 1), first as a rigid body, then by simulated annealing using torsion angle dynamics with CNS (Brünger et al., 1998). Further cycles also included restrained refinement of B-factors for individual atoms and energy minimization against maximum likelihood targets with CNS. Because the electron density for one of the molecules in the dengue E dimer was more poorly defined than the other, the atomic coordinates two molecules were tightly restrained throughout refinement and therefore have very similar structures: the Rmsd is 0.34 Å (including side chain atoms). The B-factors were left unrestrained due to a large difference in overall B-factors for the two molecules in the asymmetric unit. The atomic model was completed using 2F$_o$-F$_c$ and F$_o$-F$_c$ Fourier maps. 137 water molecules were added using an automated procedure in CNS and by visual inspection. The final model also includes two glycans, and one molecule of n-octyl-β-D-glucoside (β-OG) per protein molecule.

The structure of dengue E in the absence of β-OG was determined by refining the atomic coordinates against the 'Native3' dataset (Table 1), which was collected from a crystal grown in the absence of β-OG. The protein atoms were first refined as six rigid bodies, corresponding to domains I, II and III of each of the two chains in the asymmetric unit. The k1 hairpin (residues 270-279), and residues 165-169 were completely rebuilt. Further refinement cycles consisted of simulated annealing using torsion angle dynamics, restrained B-factor refinement for individual atoms, and energy minimization against maximum likelihood targets with CNS (Brünger et al., 1998). The structure of unliganded dengue E was determined in a second crystal form (dataset 'Native4') by molecular replacement, using a dengue E monomer as the search model in AMoRe (Navaza, 2001). The space group was identified in the translation search as P3$_2$21, with only one molecule per asymmetric unit. Rigid body refinement of domains I, II and III resulted in substantial shifts, especially for domain II, which rotated approximately 5° with respect to domains I and III. The axis of rotation passes through residue 193, and is roughly perpendicular to the dyad axis of the dimer. Further refinement cycles consisted of simulated annealing, restrained individual B-factor refinement, and energy minimization with CNS (Brünger et al., 1998). The stereochemical quality of each atomic model was validated with PROCHECK (Laskowski et al., 1993). Statistics for data collection, phasing and refinement are presented in (Table 1).

D. Atomic Coordinates

The coordinates and structure factors were deposited on Jan. 16, 2003 in the Protein Data Bank under accession numbers 1OKE and 1OAN.

E. General Description of Structure and Druggable Regions

A hydrophobic pocket in the dengue E protein must open up as a first step in the low-pH induced conformational transition, and in one of our crystal structures, a small molecule (β-octyl glucoside) is bound in this pocket.

We have determined the structure of a soluble fragment (residues 1-394) of the E protein from dengue virus type 2. This fragment contains all but about 45 residues of the E-protein ectodomain. It resembles closely, in its dimeric structure and in the details of its protein fold, the E protein from TBE, studied previously (Rey et al, 1995). Domain I, the central, 9-strand, β-barrel, organizes the structure. Insertions between strands D and E and strands H and I form the elongated domain II, which bears the fusion peptide at its tip. Domain III is an Ig-like module. Each domain of dengue sE has the same folded structure as its TBE counterpart, but several loops diverge in conformation. The relative domain orientations are also slightly different, consistent with the notion that the links between them might be flexible.

One consistent difference between E proteins from tick-borne and mosquito-borne flaviviruses is the presence in the latter of an additional four residues (382-385) between strands F and G of domain III. In our structure, these residues form a compact solvent-exposed bulge. Their relatively high temperature factors suggest some degree of flexibility. This loop has been implicated in receptor binding (Crill and Roehrig, 2001).

FIG. 1B shows the three-domain structure of the dengue virus sE dimer. Domain I, the central, 9-strand, β-barrel, organizes the structure. Insertions between strands D and E and strands H and I form the elongated domain II, which bears the fusion peptide at its tip. Domain III is an Ig-like module. In all three domains, β-strands predominate. Each domain of dengue sE has the same folded structure as its TBE counterpart, but several loops diverge in conformation. The relative domain orientations are also slightly different, consistent with the notion that the links between them might be flexible.

Figure 2:
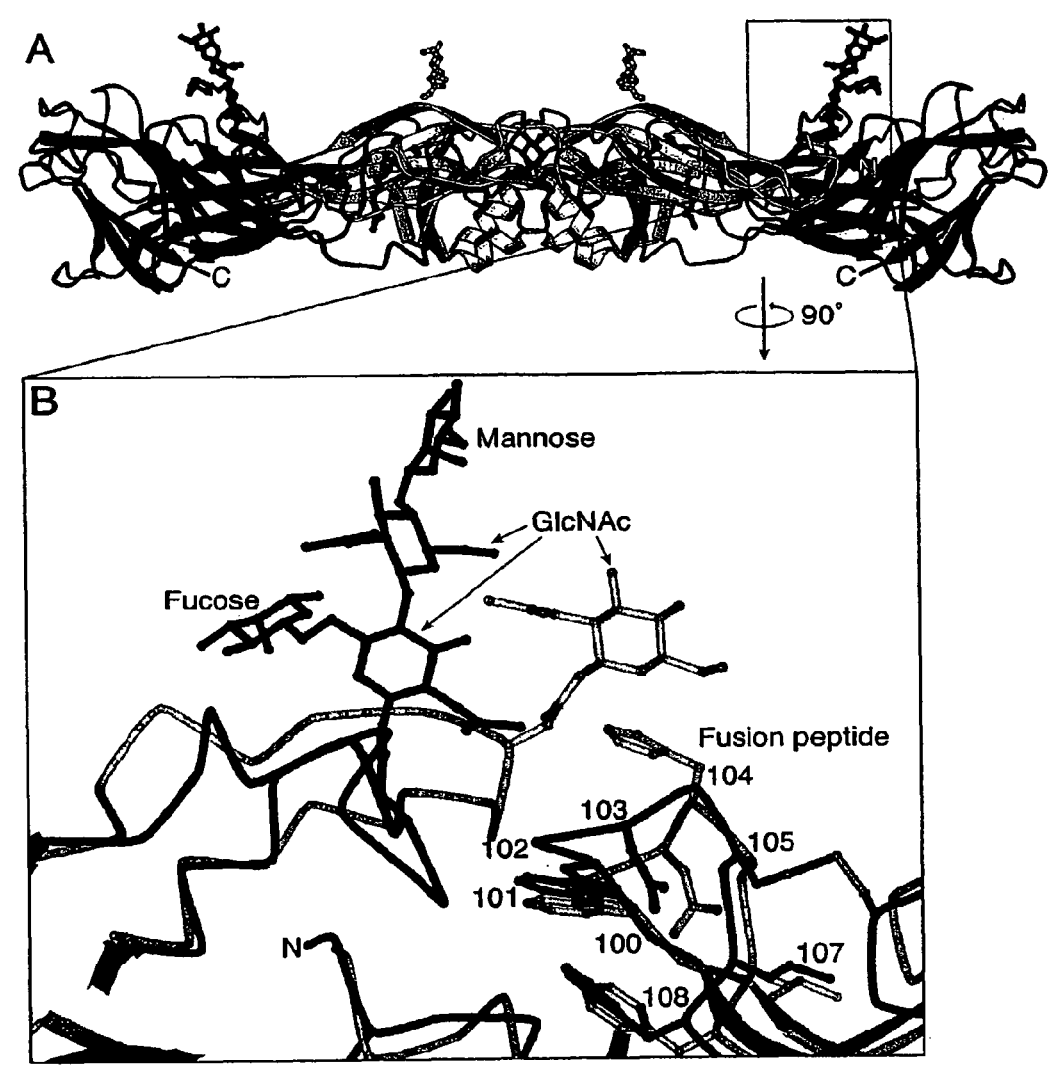

There are two glycosylated asparagines on each dengue E subunit—Asn 153 on domain I and Asn 67 on domain II. Asn153, conserved in most flavivirus envelope proteins, bears a structure modeled here as a tetrasaccharide, although it contains additional, poorly ordered sugars. The fourth sugar is a mannose, which appears to be important for viral entry (Hung et al., 1999). The glycan projects outward from the surface of the protein, and somewhat discontinuous electron-density features suggest that it makes a crystal contact with the Asn 67 glycan of another sE dimer (FIG. 2). In TBE, its homolog extends laterally across the dimer interface and "covers" the fusion peptide (residues 100-108) on domain II of the dimer partner. In the absence of a crystal contact, the dengue Asn153 oligosaccharide might do likewise. Indeed, stabilization of the dimer by the oligosaccharide would be consistent with the properties of non-glycosylated mutants of dengue, which fuse with target membranes at a higher pH (Guirakhoo et al., 1993; Kawano et al., 1993; Pletnev et al., 1993).

We have examined crystals grown in both the presence and the absence of the detergent, β-OG. The key difference between the two structures is in the k1 loop, which shifts toward the dimer contact in the presence of the detergent. This shift closes the "holes" to either side of the twofold axis and opens a tapering, hydrophobic channel at the interface between domains I and II. This channel accepts a single β-OG molecule. The β-OG head group lies at the channel's mouth, with several hydrogen bonds fixing a well-ordered orientation; the hydrocarbon chain projects well into the channel's cavity. In TBEV sE, which was studied in the absence of β-OG, the k1 loop is in the "closed" position, and the hydrophobic residues are buried.

The most significant difference between the structures of dengue sE with and without β-OG is an altered conformation of the k1 loop, which shifts toward the dimer contact in the presence of the detergent. To effect this movement, strands k and l switch sheets, from F0E0D01k to efgk1 (FIG. 1C; see also FIG. 2 of Rey et al. (1995). The shift closes the "holes" along the dimer contact to either side of the twofold axis and opens a tapering, hydrophobic channel at the interface between domains I and II. This channel accepts a single β-OG molecule. The β-OG glucosyl head group lies at the channel's mouth, with several hydrogen bonds fixing a well-ordered orientation; the hydrocarbon chain projects well into the channel's cavity. In TBEV sE, which was studied in the absence of β-OG, the k1 loop is in the "closed" position, and the hydrophobic residues are buried (FIG. 1D).

Figure 3:
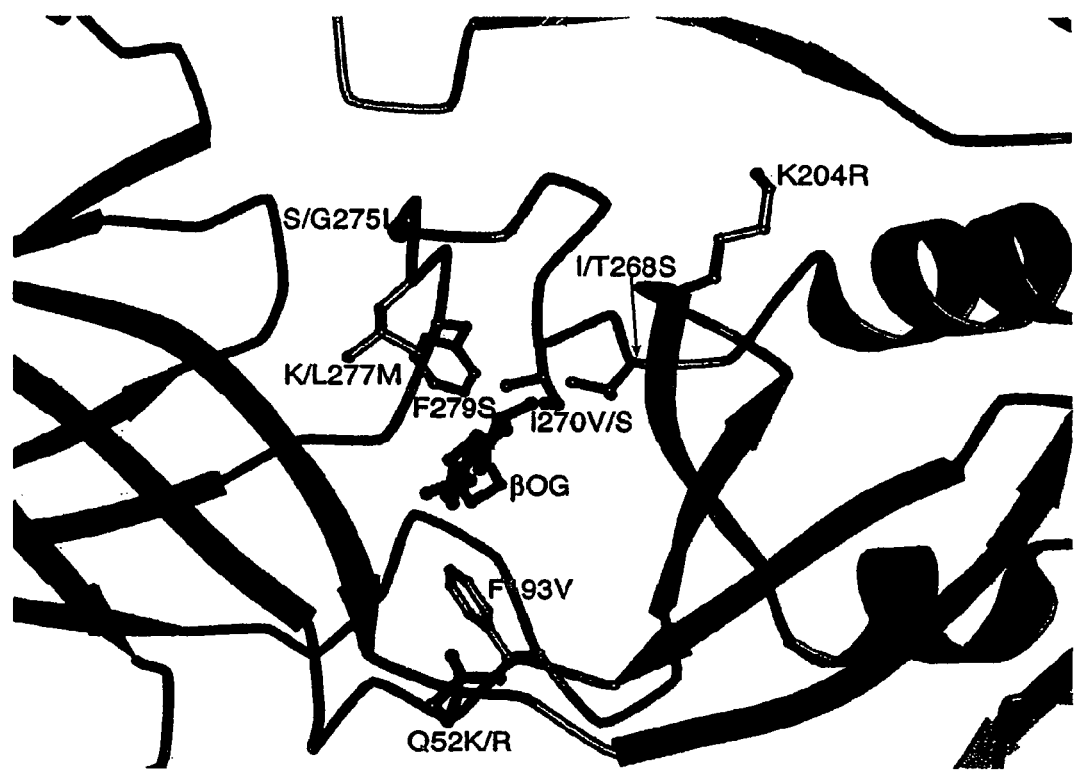
FIG. 3 depicts various mutations affecting the pH threshold of fusion in flaviviruses. The mutated residues line the interior of the ligand-binding pocket. For unconserved residues, the residue type in the virus in which the mutation was identified is listed first, followed by the residue type in dengue 2. The coloring code is the same as in FIG. 2.

Mutations of residues that participate in the domain I/II interface just described alter the threshold pH for fusion (FIG. 3). Most of them involve side chains in the β-OG binding pocket. We take this correlation as a strong indication that domains I and II indeed change orientation during the fusion-promoting conformational change. We propose that the opening of the k1 hairpin pries open the hydrophobic interface, causing domain II to hinge outwards and to project the fusion peptide at its tip toward the membrane of the target cell. Two crystallographic observations are consistent with such a hinge. In a second crystal form of dengue sE without β-OG, domain II shifts by just this type of displacement (about) 5°), with respect to domains I and III. The same is true for a second crystal form of TBE sE (Rey and Harrison). In both cases, the hinge angle is quite small, because a larger bend would disrupt the dimer contact at the tip of domain II and expose the fusion peptide. Indeed, it is just such a disruption that occurs at low pH.

In the pH-threshold mutations, substitution of longer hydrophobic side chains by shorter ones generally leads to fusion at lower pH. We suggest that shorter side chains may allow a tighter and more stable closed form of the pocket, requiring a greater drop in pH to flip it open. Attenuated viruses with single mutations in the k1 hairpin region have been obtained by passage in cell culture (Lee et al., 1997; Monath et al., 2002). Accumulation of such mutations might result in even stronger attenuation.

Figure 4:
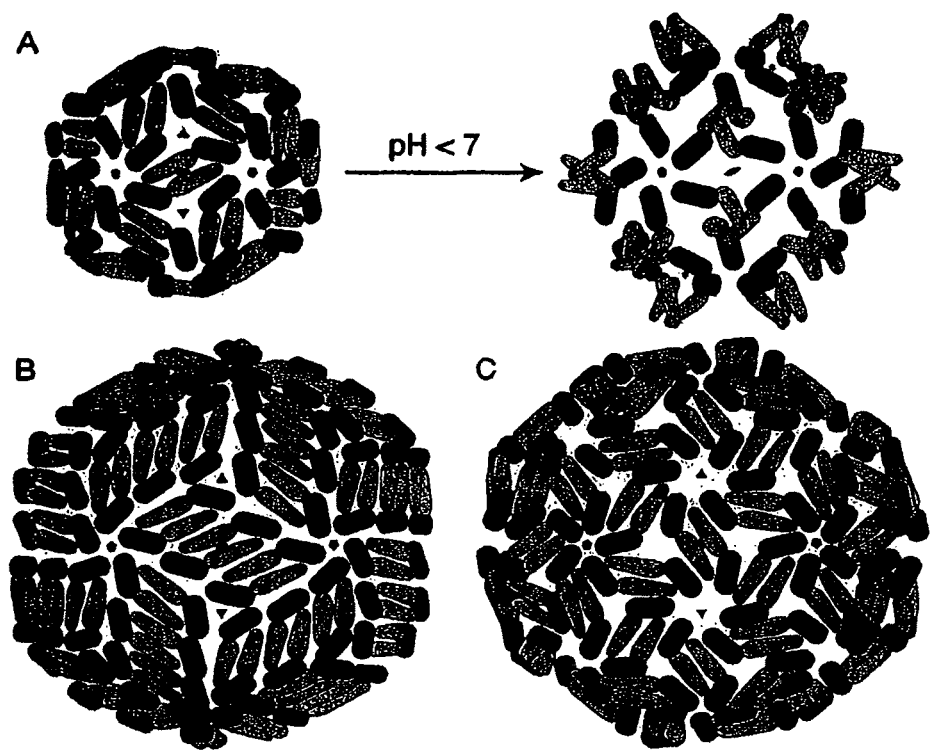
FIG. 4 depicts the proposed subunit packing interactions in various flaviviral icosahedral assemblies.
Figure 5:
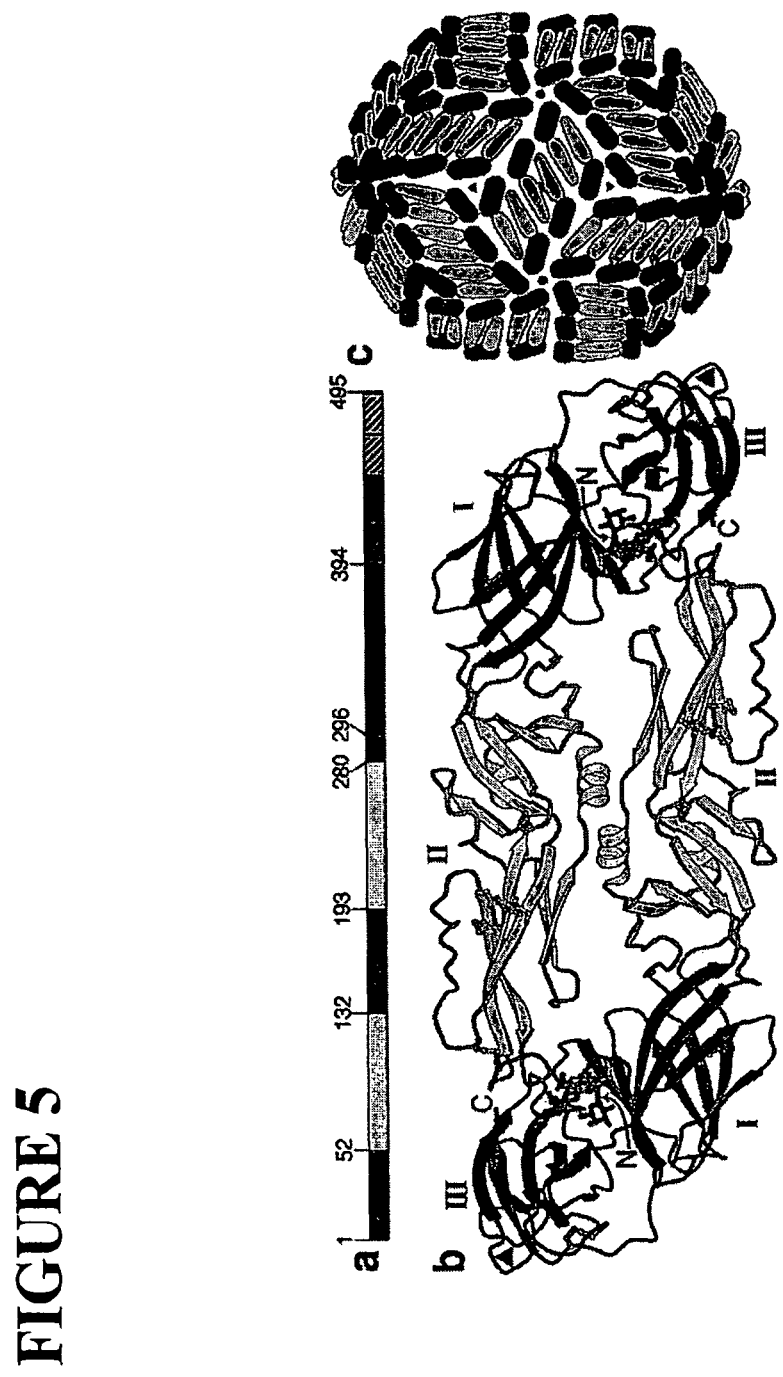
FIG. 5 depicts various views of the structure of the dimer of dengue E soluble fragment (sE) in the mature virus particle.

The outer surfaces of mature flavivirus particles contain 180 subunits each of E and M, in a compactly organized icosahedral array (Lindenbach and Rice, 2001). Any conformational change in E is therefore likely to induce a concerted reorganization across the entire surface of the virion. The E proteins cluster into trimers when they undergo their conformational change induced by low pH (Allison et al., 1995). Image reconstructions from electron cryomicroscopy of fusion-competent TBE recombinant subviral particles, which contain 60 subunits each of E and M (Ferlenghi et al., 2001), show that if domain II does hinge outwards during the low-pH induced transition, then a modest reorientation of subunits within the surface lattice will allow three of these domains to associate (FIG. 4A). The cluster thus formed will display three fusion-peptide loops at its tip. The packing of E deduced from image reconstructions of dengue virions (Kuhn et al., 2002) is at odds with this simple view, however, since the 90 dimers are not related by local threefold symmetry (FIG. 4B). Rossmann and co-workers have suggested that the surface proteins might rearrange to the structure shown in FIG. 4C as part of the low-pH induced reorganization (Kuhn et al., 2002). Note the similarities between the structures shown in FIGS.

4A (left) and 4C. As domain II bends outward, it will release many of the surface-lattice packing constraints, giving individual E subunits (or groups of subunits) considerable lateral freedom. The very tight packing of subunits in the surface of the virion at neutral pH may therefore not, in practice, be a hindrance to the postulated rearrangement.

The structure also suggests the possibility of a second druggable region, the "domain 1-3" druggable region, at which drug binding might inhibit fusion. That site, located between domains 1 and 3, is bounded by the following residues: 38-40; 143-147; 294-296; and 354-365. A small molecule bound in the pocket defined by those segments of polypeptide chain could stabilize the conformation of the E protein seen in our structure and thereby inhibit a transition to the fusion-active conformation.

In conclusion, we have identified the k1 hairpin as a key structural element for initiating the low-pH conformational change that leads to formation of fusion-competent trimers. The opening up of a ligand-binding pocket just at the locus of a likely hinge suggests that compounds inserted at this position might hinder further conformational change and hence modulate the fusion transition. In the context of the virion surface, their action might resemble that of some of the well-studied anti-picornaviral compounds, which block a concerted structural transition in the icosahedral assembly (Smith et al., 1986). Our structural observations suggest direct ways to search for such modulators.

EXAMPLE 2

Determination of the Post-Fusion Structure of E Protein from Dengue Virus Type S1

A. Expression, Purification and Crystallization of E Protein from Dengue Virus Type 2 S1

Soluble E protein (sE) from dengue virus type 2 S1 strain was supplied by Hawaii Biotech. The protein was expressed in *Drosophila melanogaster* Schneider 2 cells (obtained from ATCC) using a pMtt vector (GlaxoSmithKline) containing the dengue 2 prM and E genes (nucleotides 539-2121 of the sequence) as described in Section A of Example 1. The resulting prM-E preprotein is processed during secretion to yield sE, which was purified from the cell culture medium by immunoaffinity chromatography.

Dengue sE trimers were obtained as follows, based on a method developed for tick-borne encephalitis virus sE (Stiasny, K., et al. *J. Virol.* 76, 3784-3790 (2002)). 1-palmitoyl-2-oleoyl-sn-glycero-3-phosphocholine, 1-palmitoyl-2-oleoyl-sn-glycero-3-phosphoethanolamine (Avanti Polar Lipids) and 1-cholesterol (Sigma) were dissolved in chloroform, mixed in a 1:1:1 molar ratio, and dried under high vacuum for at least 4 h. The lipid film was resuspended in 10 mM triethanolamine (TEA) pH 8.3, 0.14 M NaCl and subjected to five cycles of freeze-thawing, followed by 21 cycles of extrusion through two 0.2 μm polycarbonate filter membranes (Whatman). Purified sE was added in a 1:680 protein:lipid molar ratio and incubated at 37° C. for 5 min. The pH was lowered to endosomal levels by adding 75 mM MES pH 5.4, and the protein was incubated at 37° C. for 30 min. Liposomes were solubilized with a 20-fold molar excess n-octyl-β-D-glucoside (β-OG) and 4 mM n-undecyl-β-D-maltoside (UDM) (Anatrace). Excess lipid was removed by cation exchange chromatography with MonoS (Pharmacia) in 25 mM citric acid pH 5.26, 70 mM NaCl, 4 mM UDM. After washing with 0.4 M NaCl, the protein was eluted with 1-1.5 M NaCl. E trimers were further purified by gel filtration on a Superdex 200 column (Pharmacia) in 8 mM TEA pH 7, 80 mM NaCl, 3 mM UDM. The sE trimers were concentrated to about 15 mg ml$^{-1}$ for crystallization and dialyzed against the gel filtration buffer using a 50-kDa molecular-mass cutoff membrane (Spectrapor).

Crystals grew at 20° C. by hanging drop vapor diffusion by mixing equal volumes of protein solution and the following reservoir solution: 20-30% polyethylene glycol 400 (PEG400), 0.1 M MOPS pH 7-8 or Tris pH 8-9, 80 mM NaCl. Two crystal forms were obtained: plates of space group P321 with cell dimensions a=b=76.2 Å, c=131 Å, and rhomboids of space group P3$_2$21 with cell dimensions a=b=153 Å, c=143 Å. The asymmetric unit of the P321 crystals contains one molecule of sE; that of the P3$_2$21 crystals, one trimer (three molecules) of sE.

B. Data Collection and Processing

Cryoprotection was achieved by raising the concentration of PEG400 to 30%. Crystals were frozen in liquid nitrogen, and all data were collected at 100 K on BioCARS beamline 14-BM-C at the Advanced Photon Source (Argonne National Laboratory). The data were processed with HKL. Data collection statistics are presented in Table 2.

TABLE 2

Crystallographic data and refinement statistics.

| | Dataset (space group) | |
|---|---|---|
| | P321 | P3$_2$21 |
| Molecules per asymm. unit | 1 | 3 |
| Cell edges a(=b)/c | 76.2/131 | 153/143 |
| Resolution range (Å) | 30-2.0 | 30-3.25 |
| % completeness | 95 (75) | 99 (98) |
| I/σ(I) | 24.5 (2.0) | 14.3 (3.0) |
| R$_{merge}$† (%) | 5.8 (39.8) | 13.2 (54.3) |
| Unique reflections | 27,450 | 30,779 |
| R$_{cryst}$ | 0.2213 | |
| R$_{free}$† | 0.2671 | |
| Average B-factor (Å$^2$) | | |
| Protein (chain A/B/C) | 29.6 | |
| Solvent | 34.4 | |
| Rmsd bond length (Å) | 0.006 | |
| Rmsd bond angle (°) | 1.410 | |
| Rmsd bonded B-factor (Å$^2$) | | |
| Main chain | 3.29 | |
| Side chain | 4.72 | |
| Rmsd (trimer-dimer) (Å) | | |
| Domain I | 5.69 | |
| Domain II | 2.61 | |
| Domain III | 2.21 | |
| Ramachandran plot (%) | | |
| Favored | 88.9 | |
| Allowed | 10.2 | |
| Generous | 0.9 | |
| Disallowed | 0 | |

Rmsd, root mean square difference.
R$_{cryst}$ = Σ$_{hkl}$||F$_{obs}$| − |<F$_{calc}$>||/Σ$_{hkl}$|F$_{obs}$|
†R$_{free}$ = R$_{cryst}$ using 5% of F$_{obs}$ sequestered before refinement.

C. Structure Determination and Refinement

The crystal structure of dengue E in the post-fusion conformation was determined by molecular replacement using individual domains from the pre-fusion dengue E structure (described in Example 1) (Protein Data Bank code 1OKE) as search models, and the P321 dataset (Table 2). Domain II was placed first, followed by domain I, with AmoRe. Domain III was placed last, with CNS. The atomic coordinates of the three domains were refined as rigid bodies. The model was rebuilt with O based on 2F$_o$–F$_c$ and F$_o$–F$_c$ Fourier maps.

Residues 1-17, 34-40, 49-54, 128-137, 165-192, 290-299 and 341-346 were built de novo. Coordinates were then refined against data up to 2.0 Å resolution by simulated annealing using torsion angle dynamics with CNS, and rebuilt with O, in iterative cycles. Later cycles included restrained refinement of B-factors for individual atoms and energy minimization against maximum likelihood targets with CNS. The final model contains residues 1-144 and 159-394, an n-acetyl glucosamine glycan on residue 67, 205 water molecules and one chloride ion. Residues 145-158 and the glycan on residue 153 were disordered. The stereochemical quality of the atomic model was validated with PROCHECK. Refinement statistics are presented in Table 2.

D. Atomic Coordinates

Coordinates have been deposited in the Protein Data Bank under accession code 1OK8.

E. Electron Microscopy.

Dengue sE trimers inserted into liposomes were prepared as described above and adsorbed to glow-discharged, carbon-coated copper grids. Samples were washed with two drops of deionized water, stained with two drops of 0.7% uranyl formate for 20 s, washed with water, and blotted gently. Micrographs were recorded on a Philips Tecnai 12 electron microscope at 100 kV and 64.000-fold magnification.

F. Crosslinking.

To determine the oligomerization state of sE by SDS-PAGE, sE was covalently cross-linked with ethylene glycol bis-(succinimidyl succinate) (EGS). 10 μM-1 mM EGS was added from a fresh 0.1 M stock solution in dimethyl sulfoxide to about 5 μg E at 10 μg ml$^{-1}$. Acidic solutions were neutralized with TEA pH 8.5. After 30 min at room temperature, EGS was quenched with 20 mM Tris for 15 min. Protein was precipitated with trichloroacetic acid and resuspended in SDS-PAGE sample buffer for gel electrophoresis.

G. General Description of Structure and Druggable Regions

The crystal structure we describe here, of the soluble ectodomain of dengue virus type 2 E protein (sE) in its trimeric, post-fusion conformation, provides valuable insight into the mechanism of fusion. The fusion loops of the three subunits come together to form a membrane-insertable, "aromatic anchor" at the tip of the trimer. The fusion loop retains its pre-fusion conformation. Neighboring hydrophilic groups will restrict insertion to the proximal part of the outer lipid-bilayer leaflet. The entire ectodomain of the protein folds back on itself, directing the C-terminal, viral membrane anchor toward the fusion loop. The fusion loop may serve as a druggable region, for example, as a target for molecules that inhibit its interactions.

Comparison with the pre-fusion structure of the same protein allows us to propose a mechanism for fusion driven by an essentially irreversible conformational change in the protein and assisted by membrane distortions imposed by fusion-loop insertion. Specific features of the folded-back structure suggest strategies for inhibiting flavivirus entry.

Membrane Insertion and Trimer Formation

Figure 6:
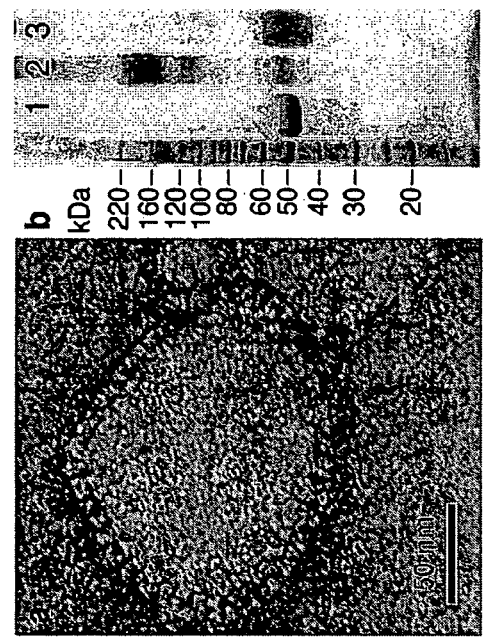
FIG. 6 depicts the trimer formation and membrane insertion of dengue E protein.

Like its TBE homolog, the dimer formed by dengue sE (residues 1-395 of E) dissociates reversibly. At acidic pH, dissociation is essentially complete at protein concentrations of 1 mg ml-1; at neutral pH, the dissociation constant is one to two orders of magnitude smaller. The fusion loop at the tip of domain II would be exposed in the monomer, but exposure does not cause non-specific aggregation of the protein. Liposome coflotation experiments show that the fusion loop of monomeric TBE sE allows association with lipid membranes and that this membrane association catalyzes irreversible formation of sE trimers at low pH. Dengue E exhibits an identical behavior: upon acidification, sE dimers dissociate, bind liposomes and trimerize. Membrane associated sE is readily detected by electron microscopy of negatively stained preparations (FIG. 6A); chemical cross-linking confirms that the protein has trimerized (FIG. 6B). The trimers are tapered rods, about 70-80 Å long and 30-50 Å in diameter, with the long axis perpendicular to the membrane and their wide end distal. They tend to cluster on the liposome surface, often forming a continuous layer. These heavily decorated areas appear to have a greater than average membrane curvature, resulting in smaller vesicles (FIG. 6A). This observation suggests that E trimers can induce curvature, a property that may be significant for promoting fusion (see below). The dengue sE trimers can be solubilized with the detergent n-octyl-β-D-glucoside (β-OG); they remain trimeric at all pHs between 5 and 9, as determined by gel filtration chromatography.

Structure of the Trimer: Domain Rearrangements

Figure 7:
FIG. 7 depicts various views of the domain rearrangements in the dengue sE monomer during the transition to trimer.

The three domains of the sE retain most of their folded structures, but undergo major rearrangements in their relative orientations, through flexion of the interdomain linkers (FIG. 7). Domain II rotates approximately 30° with respect to domain I, about a hinge near residue 191 and the k1 hairpin (residues 270-279), where mutations that affect the pH threshold of fusion are concentrated. As a result of the rotation, the base of the k1 hairpin is pulled apart, and the 1 strand forms a new set of hydrogen bonds with the D0 strand of domain I, shifted by two residues from the hydrogen bonding pattern in the dimer. Although detergent is present, the k1 hairpin does not adopt the open conformation seen in the dimer with bound β-OG7. The small hydrophobic core beneath this hairpin seems to be a "greased hinge" for the rotation between domains I and II. The k1 hairpin region and the hydrophobic core beneath it may serve as a druggable region.

Domain III undergoes the most significant displacement in the dimer-to-trimer transition. It rotates by about 70°, and its center of mass shifts by 36 Å towards domain II. This folding-over brings the C-terminus of domain III (residue 395) 39 Å closer to the fusion loop and positions it at the entrance of a channel, which extends toward the fusion loops along the intersubunit contact between domains II (FIG. 8A, B). The 53-residue "stem" connecting the end of the sE fragment with the viral transmembrane anchor could easily span the length of this channel, even if the stem were entirely α-helical. By binding in the channel, the stem would contribute additional trimer contacts with domain II of another subunit (FIG. 8B). The stem does indeed promote trimer assembly even in the absence of liposomes. In the virion, the stem appears to form two α-helical segments, which lie in the outer surface of the lipid bilayer and contact the membrane-facing surface of the subunit from which they emanate. The stem, or portions thereof, may serve as a druggable region. Further, areas in which the stem binds, such as the channel, may also serve as druggable regions.

Changes in the Secondary Structure

The 10-residue linker between domains I and III accommodates their large relative displacement during trimer formation. The linker, which has a poorly ordered, extended structure in the pre-fusion dimer (FIG. 7A), inserts in as a short β-strand between strands A0 and C0 in domain I (FIG. 7B). As part of this rearrangement, the C-terminal region of A0 peels away from C0 and switches to the other n-sheet, thereby creating the surface for an annular trimer contact with the two other A0 strands in the trimer.

The transition to the trimer state is irreversible. It may represent the step at which virus and host-cell membranes are forced together to promote fusion. The refoldings just described may impart irreversibility. They resemble in some respects another well-known irreversible protein refolding, activation of serpins, in which a β-strand also inserts between two other strands in a previously formed sheet. The chain rearrangements in dengue E can contribute a high barrier to initiation of trimerization (sE monomers do not trimerize at low pH without liposomes) and the even higher barrier to dissociation of trimers once they have formed.

Trimer Contacts

Figure 8:
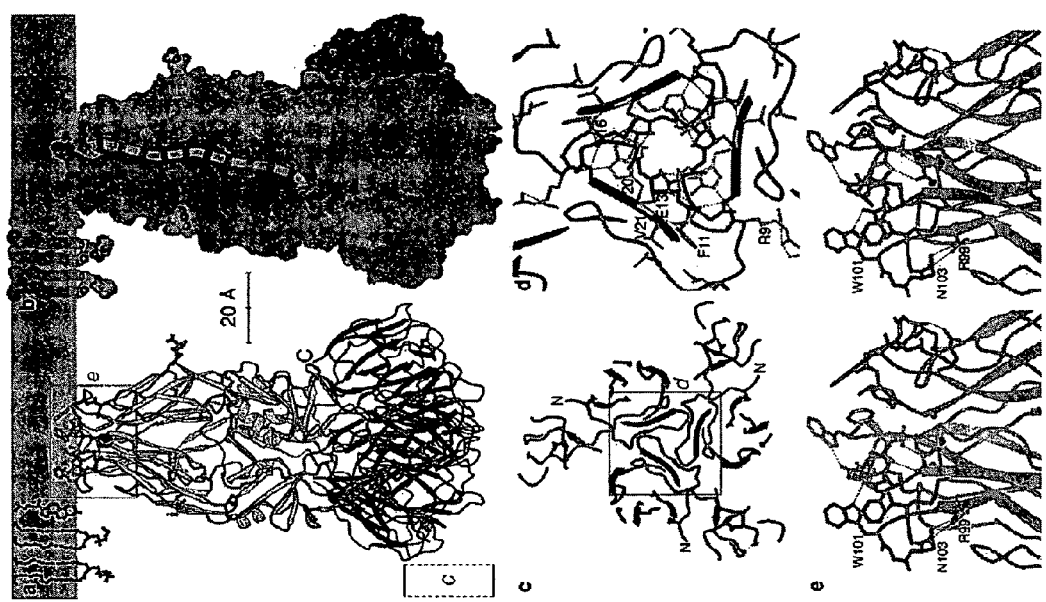
FIG. 8 depicts various views of the dengue sE trimer.

Dengue E trimers assemble through both polar and nonpolar contacts in four areas: at the membrane-distal end of the trimer, at the base of domain II, at the tip of domain and at the packing interface between domains I and III (FIG. 8). The total surface buried per monomer during trimer assembly is 3900 Å2—twice the 1950 Å2 per monomer buried in the dimer. An additional 1035 Å2 are buried within each monomer during the domain rearrangements observed in our structure. These numbers help explain why trimers are much more stable than dimers in solution. They also help account for the irreversibility of the fusion-activating conformational change. Additional trimer contacts are likely to be contributed by the stems, as described above.

An extended cavity, which runs along the threefold axis, separates the trimer contact areas at the top and at the base of domain II. A narrow opening connects this cavity with the exterior solvent, but it may be occluded by the stem in the full-length protein (FIG. 8B). An anion, modeled as a chloride, lies on the threefold axis near the tip of domain II. It is liganded by three amide nitrogen (from Lys110 on each of the subunits) and by three water molecules. Between this anion and the domain-II tip, a small hydrophobic core underpins the nonpolar, bowl-shaped apex formed by the three clustered fusion loops.

The Fusion Loop

The fusion loops in the sE trimer have the same conformation as in the dimer. Because the trimers are obtained by detergent extraction from liposomes, we conclude that this conformation is also present when the loop inserts into a membrane. Furthermore, as dimers can dissociate reversibly, the fusion loop is stable when fully exposed. In short, it appears that the fusion loop retains essentially the same conformation, whether buried against another subunit, inserted into a lipid membrane, or exposed to aqueous solvent.

In the trimer, the three hydrophobic residues in the fusion loop conserved among all flaviviruses—Trp101, Leu107 and Phe108—are fully exposed on the molecular surface, near the threefold axis. They form a bowl-like concavity at the trimer tip, with a hydrophobic rim (FIG. 8E). There are no lipid or detergent molecules visible in the electron density near the fusion loop in either of our crystal forms. Indeed, in the P321 crystal form, there can be no detergent micelle covering the fusion loop, as this region is involved in close crystal contacts with residues in domain III of a symmetry-related molecule. We conclude that detergent is required to dissolve away the liposome on which the trimer formed and hence to solubilize the protein, but that once the protein has been extracted from the membrane, the threefold-clustered fusion loops do not retain a tightly associated detergent micelle.

How deeply, then, do fusion loops penetrate into the membrane? Tryptophan side chains tend to appear in membrane proteins at the interface between the hydrocarbon and headgroup layers of the lipid 18, but if the indole amine participates in a hydrogen bond, as is the case for Trp 101, the side chain may be completely buried in the hydrocarbon layer. We therefore propose that the E trimers penetrate about 6 Å into the hydrocarbon layer of the target membrane. They cannot penetrate further, because of exposed carbonyls and charged side chains on the outside rim of the fusion-loop bowl (FIG. 8E). Thus, the fusion loop is held in the membrane mainly by an "aromatic anchor" formed by Trp101 and Phe108. The bowl is lined by the hydrophobic side chains of Leu107 and Phe108, so that it cannot accommodate lipid headgroups. We expect that fatty-acid chains from the inner leaflet of the membrane may extend across to contact the base of the fusion-loop bowl, or that fatty-acid chains from the outer leaflet may bend over to fill it. In either case, insertion will produce a distortion in the bilayer, probably leading to positive curvature. Distortion of this type could be important for the fusion process (see below).

The sE Trimer Represents a Post-Fusion Conformation

The folding back of domain III and the rearrangement of β-strands at the trimer interface projects the C-terminus of sE toward the fusion loop, and the most likely model (FIG. 8B, discussed above) has the 53-residue C-terminal stem running along the channel between domains II of adjacent monomers. The proposed stem conformation places the viral transmembrane domain in the immediate vicinity of the fusion loop, just as in the post-fusion conformations of class I viral fusion proteins, such as those of influenza virus and HIV. We therefore believe that the trimer we have crystallized represents a post-fusion state of the protein.

Mechanism of Membrane Fusion

Figure 9:
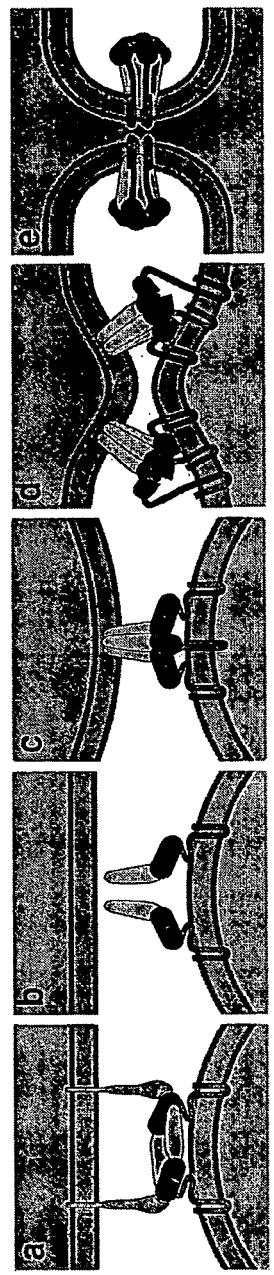

The structure of the sE trimer described here suggests how conformational changes in the flavivirus E protein can promote membrane fusion (FIG. 9).

(1) E associates with a cell-surface receptor, probably through domain III (FIG. 9A), but there is evidence for glycan-mediated interactions as well. Receptor binding leads to endosomal uptake. Domain III may serve as a druggable region.

(2) Reduced pH in the endosome causes the E dimers on the virion surface to dissociate, exposing the fusion loops and allowing domain I and II to flex relative to one another (FIG. 9B). Evidence for a pH-dependent hinge at the domain I-domain II interface includes the location of mutations that alter the pH-threshold of fusion, as well as the difference in orientation between the pre- and post-fusion structures. Release of the constraints imposed by dimer contacts may also allow the stem to extend away from the membrane. Some combination of these two sources of flexibility will allow domain II to turn outward, away from the virion surface, and to insert its fusion loop into the target-cell membrane. The pH-dependent hinge may serve as a druggable region.

(3) Outward projection of domain H will destroy tight packing interactions on the virion outer surface, allowing lateral rearrangement of E monomers. Thus, the absence of trimer clustering in the virion is not, in principle, a barrier to trimer formation. Trimerization through domain H might occur before or after interaction of the fusion loop with the target cell. Liposome binding is necessary for sE to trimerize, but it is not essential for trimerization of longer E polypeptides. Because at this stage in fusion, the stem of E is probably not free to participate in trimer formation, and because domain III may still be constrained by receptor contacts, we believe that target membranes are probably required to catalyze trimerization. Whatever the precise order of events, we propose that the combination of fusion-loop insertion and trimer interactions among domains II leads to a pre-fusion intermediate, in which the trimer bridges host-cell and viral membranes, with its fusion loops bound to the former and its transmembrane tail anchored in the latter (FIG. 9C). This species is analogous to the "pre-hairpin" intermediate postulated for class I viral fusion mechanisms. The regions of domain II involved in trimerization may present a druggable region.

(4) Formation of trimer contacts spreads from the fusion loops at the trimer tip to domain I at the base. Domain III shifts and rotates, folding the C-terminal part of E back toward the fusion loop (FIG. 9D). The length of the interdomain linker permits independent rotation of individual domains III, allowing for the spontaneous symmetry-breaking required at this point. Cooperativity and irreversibility occur only when the exchange of β-strands shown in FIG. 7D locks in the final domain-I trimer interaction and the final folded-back position of domain III. Free energy released by this refolding can drive the two membranes to bend toward each other. A ring of trimers is presumably needed properly to deform the membrane. We cannot yet specify the number of trimers in such a ring nor how their conformational changes are coupled. It is possible, however, that coupling is provided simply by the resistance of the membranes to deformation: only when several trimers act in concert can folding back reach the barrier of β-strand exchange.

(5) In the final state, the trimer has reached the conformation seen in our crystal structure, with the stems (not present in our current crystals) docked along the surface of domains II and with the fusion loops and transmembrane anchors now next to each other in the fused membrane (FIG. 9E). The stem-domain II contact regions may present druggable regions.

When membranes fuse, the two lipid bilayers—the "substrates" of the fusion reaction—must undergo a sequence of deformations. Formation of a "hemifusion stalk", with proximal leaflets fused and distal leaflets unfused, is thought to be an essential intermediate, followed by a transition to a lipidic fusion pore when distal leaflets merge. Specific models for the stalk differ substantially. Where along the pathway of protein rearrangement just described does a hemifusion stalk form, and what stimulates its transformation to a pore? We offer the following suggestions. (1) To initiate fusion, portions of each bilayer must approach each other to within a distance of 10 Å. The two membranes may form apposing "domes" or "nipples" to allow room for the fusion proteins, as illustrated in FIG. 9D. Positive bilayer curvature induced by fusion-loop insertion might stabilize the lateral surfaces of such a protrusion. (2) Hemifusion could occur at any point during the process represented by FIG. 9D, depending on the length of the hemifusion stalk. It seems to us most likely that hemifusion would happen during or following the β-strand exchange step that locks domains III into their trimer positions. It must, of course, precede final zippering up of the stems, as full pore formation must occur before the transmembrane segments can reach their likely final positions around the periphery of the fusion loops. (3) Hemifusion stalks can "flicker" open into narrow fusion pores. Migration of the transmembrane segments along a transient pore will prevent its closing. Thus, if the transmembrane segments (or the stretch of polypeptide chain leading into them) "snap" into place around the tips of domains II, formation of the symmetrical final structure (FIG. 9E) could drive the transition from stalk to pore.

Comparison with Class I Fusion

Despite their very different molecular architectures, the class I and class II viral fusion proteins clearly have some common mechanistic features (FIG. 9). The most striking of these is a folding back of the protein during the fusion transitions, so that its two membrane attachment points come together in the post-fusion structure. Class I proteins fold back by zippering up an "outer layer" (at least partly α-helical) around a central, trimeric coiled-coil (reviewed in ref. 1). Our structure of trimeric dengue sE shows that class II proteins do so by nucleating trimer formation around an elongated, finger-like fusion domain, by rearranging two other domains, and (probably) by zippering an extended C-terminal stem along the trimer surface.

Class II viral fusion proteins form trimers from monomers (dissociated homodimers in the case of flaviviruses; dissociated heterodimers in the case of alphaviruses35), while class I proteins are trimeric in their pre-fusion state. But comparison of the pre- and post-fusion states of influenza haemagglutinin—the only previous case where both structures are known for the same protein—shows that most of the trimer contacts in the latter state are not present in the former. That is, just as in the trimerization of dengue E, the important trimer interactions in the final state form during the transition. These contacts are, of course, close to the threefold axis, and they must be present before zippering up of an outer layer can occur. Indeed, the postulated pre-fusion intermediate is, both for class I fusion proteins and now for class II, a structure in which these central trimer contacts have formed but the zippering up of the outer layer has not yet begun (FIG. 9).

Is our structure for the membrane-inserted state of the flavivirus fusion loops relevant also for class I fusion-peptide insertion? An NMR structure of an isolated, 20-residue influenza virus A fusion peptide associated with a detergent micelle suggests a slightly kinked α-helix, with its N- and C-termini embedded in the outer leaflet and the kink (at about residue 10) on the surface. Unlike the flavivirus and alphavirus fusion loops, however, the class-I fusion peptides have no particular sequence conservation. Indeed, the Ebola virus fusion peptide begins at the 23rd residue of GP2, rather than at the N-terminus 37, and a cysteine preceding the fusion peptide probably makes a disulfide bond with a cysteine C-terminal to it. Thus, whatever its conformation, this peptide must enter and leave the membrane from the same (external) face. Available data for class I fusion peptides are thus consistent with one important feature of our structure and of the SFV E1 post-fusion structure—insertion only into the outer bilayer leaflet.

Insertion only into the outer leaflet is also consistent with the requirement of a complete C-terminal transmembrane anchor on influenza HA or Simian virus 5 for full fusion to take place. As illustrated by FIG. 9E, one of the two membrane attachment structures must span a bilayer to stabilize a fusion pore. This appears to be the C-terminal anchor for class I fusion, as well a for class II.

EXAMPLE 3

Inhibitors of Flavivirus Entry

The discovery of a hydrophobic ligand-binding pocket beneath the k1 loop in the pre-fusion structure of dengue sE has suggested one possible strategy for inhibiting flavivirus entry by interfering with the fusion transition. The rationale for that proposal is enhanced by our new structure, which shows that significant rearrangements do occur around the k1 loop during the conformational change. The trimer structure also suggests a second strategy for interfering with fusion, related to an approach successful in developing an HIV antiviral compound. Peptides corresponding to the C-terminal region of the gp41 ectodomain inhibit HIV-1 entry, probably by binding to the trimeric, N-terminal "inner core" of the protein and interfering with the folding back of the C-terminal "outer-layer" against it. An analogous strategy may be possible with some class II viral fusion proteins, such as those of dengue and hepatitis C. The way in which the stem is likely to fold back suggests that peptides derived from stem sequences could block completion of the conformational change, by interacting with the relevant surfaces on the clustered domains II. This approach would interfere with the second stage of the conformational change, while targeting the pocket beneath the k1 loop would probably interfere with the first stage. The two would thus be usefully complementary.

A. Stem Peptide Inhibitor Corresponding to Residues 396-429 of the Stem Region of E.

Figure 10:
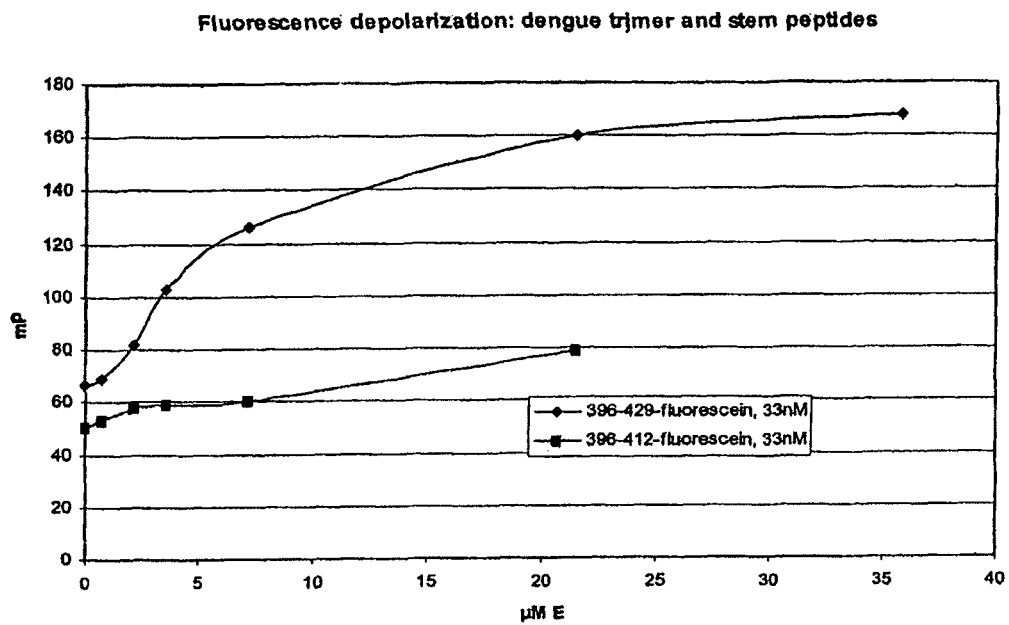
Figure 10:
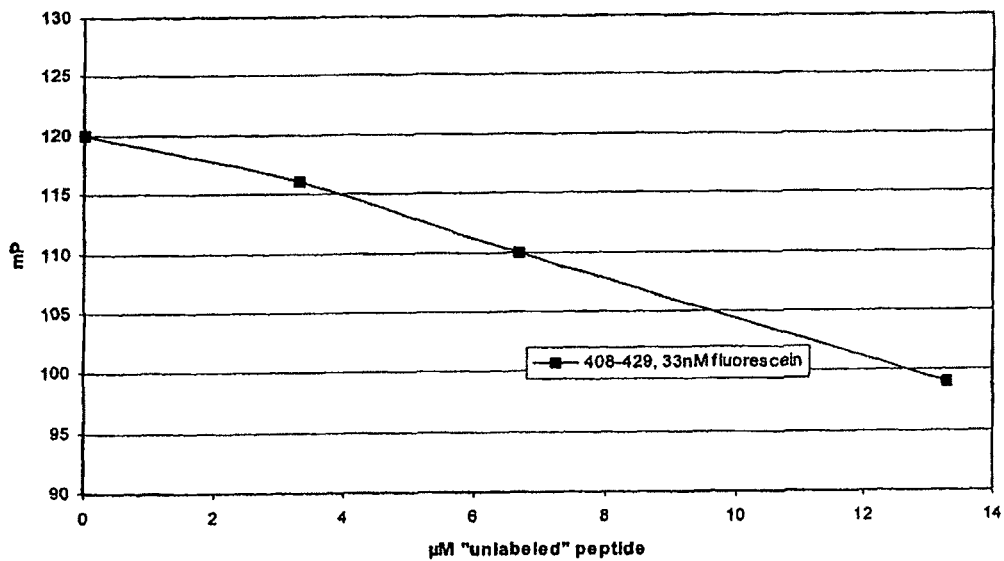

A peptide corresponding to residues 396-429 (in the "stem" region) of dengue envelope protein (E) binds with fairly high affinity and specificity to the trimeric, post-fusion form of sE, the fragment of E spanning residues 1-395, which we crystallized first in the pre-fusion form and then in the post-fusion form. We determined the dissociation constant (Kd) of the peptide from sE from fluorescence depolarization measurements using a fluorescently labeled version of the peptide. The Kd is around 6 μM. This indicates a fairly strong binding. FIG. 10 depicts the fluorescence depolarization results. The Kd is approximately equal to the concentration of sE at which the depolarization (in mP) reaches its half-maximal value (see FIG. 10A). FIG. 10B shows that fluorescently labeled peptide can be competed off of sE with unlabeled peptide. This is important because it demonstrates that the binding is specific to one site of sE, and is not due to several different weak non-specific sites. The sequence of the peptide (residues 396-429) is:

```
SEQ ID NO: 3:
SSIGQMFETTMRGAKRMAILGDTAWDFGSLGGVF.
```

B. Stem Peptide Inhibitor Corresponding to Residues 413-447 of the Stem Region of E.

Another stem region-derived polypeptide binds trimeric (postfusion) sE with slightly higher affinity than the polypeptide comprising residues 396-429. This stem peptide includes residues 413-447 of sE (whereas the entire stem spans 396-447). The protein sequence for the new stem peptide (413-447) used in the attached graph is:

```
SEQ ID NO: 4:
AILGDTAWDFGSLGGVFTSIGKALHQVFGAIYGAA
```

Figure 11:
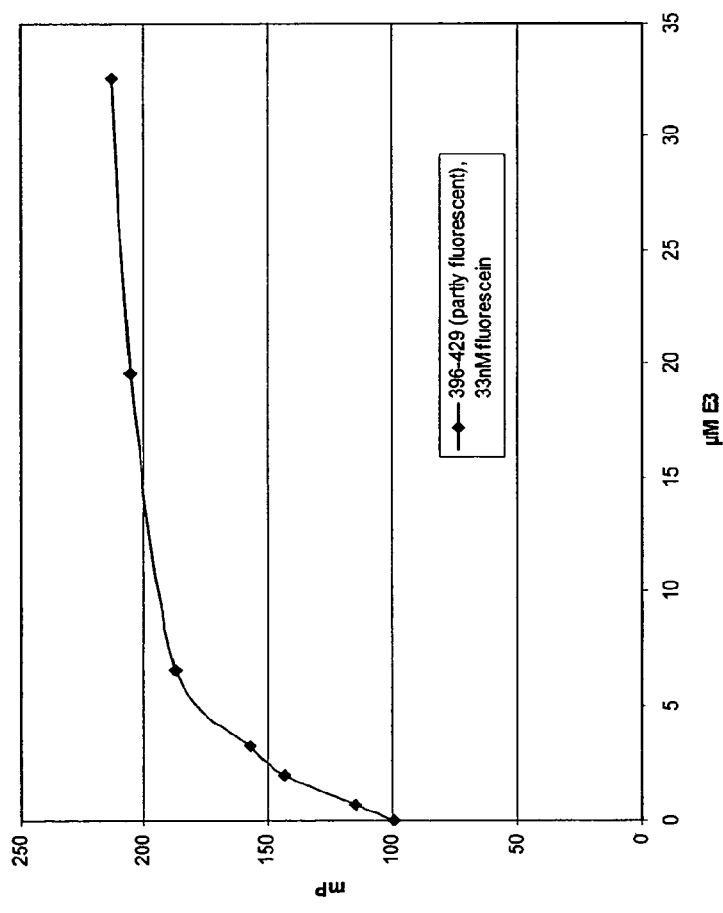

The Kd is approximately 4 μM (FIG. 11), compared to 6 μM for 396-429 (FIG. 10A). This polypeptide, as well as the polypeptide comprising residues 396-429, may comprise good starting points for peptide or peptidomimetic drugs.

Accordingly, the present invention is directed toward inhibitors comprised of SEQ ID NO: 3 and SEQ ID NO: 4, as well as fragments, homologs, variants, orthologs, and peptidomimetics thereof. Such inhibitors may have at least about 80%, at least about 85%, at least about 90%, at least about 95%, about 96%, about 97%, about 98% or about 99% homology with either SEQ ID NO:3 or SEQ ID NO: 4.

These polypeptides bind in a channel formed at the trimer interface formed by domain II of each subunit in the trimer. Domain II consists of residues 52-132 and 193-280. Hence, the channel formed at the trimer interface comprises a druggable region of the invention. Further, the present invention is directed towards inhibitors that interact with the relevant surfaces on channel, so that completion of the conformational change is inhibited and thereby the activity of the dengue virus E protein or other E protein is inhibited.

The present invention is also directed towards an inhibitor that interacts with the pocket beneath the k1 loop to interfere with the first stage of the conformational change, thereby modulating the activity of the dengue virus E protein or other E protein. Such inhibitors may be used in complementary approaches to treat dengue viral or other viral infections.

EXAMPLE 4

Druggable Regions

Based in part on the structural and inhibitor data described above in Examples 1-3, in one aspect, the present invention is directed towards druggable regions of a dengue virus E protein or other flavivirus E protein comprising the majority of the amino acid residues contained in a subject druggable region. Such druggable regions may be utilized in the structure determination, drug screening, drug design, and other methods described and claimed herein. In another aspect, the present invention is directed toward an modulator that interacts with such druggable regions. In still another aspect, the present invention is directed toward an modulator that is a fragment of (or homolog of such fragment or mimetic of such fragment) the druggable region of a dengue virus E protein or other viral class II E protein and competes with that druggable region.

In one embodiment, the druggable region is comprised of the k1 hairpin or a portion thereof. In certain embodiments, the k1 hairpin may be comprised of at least one of residues 268-280 of a dengue virus E protein or the homologous residues in other class II E protein. In other embodiments, the druggable region or active site region may be comprised of the k1 hairpin and at least one of residues 47-54, 128-137, and 187-207. In another aspect, the present invention is directed towards a modulator that interacts with the k1 hairpin so as to preclude it from moving, thereby modulating the activity of the dengue virus E protein or other flavivirus E protein.

In yet another embodiment, the druggable region may comprise the regions involved in the binding of residues 396-429 (the "stem" region of dengue envelope protein E) binds to the trimeric, post-fusion form of dengue virus E protein or other flavivirus E protein. In one embodiment, the druggable region is comprised of the stem region or a portion thereof. The stem region comprises residues 396-447, or fragments thereof, for example 396-429 and 413-447. In another embodiment, the druggable region is comprised of the channel in which the stem region binds. The channel is comprised of the residues at the trimer interface formed by domain II of each subunit in the trimer. Domain II consists of residues 52-132 and 193-280. A second region is the channel where the stem binds, formed by residues in domain II. In another aspect, the present invention is directed towards a modulator that interacts with the stem region or the channel so as to preclude them from interacting, thereby modulating the activity of the dengue virus E protein or other flavivirus E protein. Such modulators may be, as described above, derived from either the stem region or the channel, and compete with the stem region or channel for binding.

In another embodiment, the druggable region is comprised of the domain I-III region. In certain embodiments, the domain I-III region may be comprised of at least one of residues 38-40; 143-147; 294-296; and 354-365 of a dengue virus E protein or the homologous residues in other class II E protein. In another aspect, the present invention is directed towards a modulator that interacts with the domain 1-3 region so as to preclude it from moving, thereby modulating the activity of the dengue virus E protein or other E protein. In other embodiments, the druggable region may be comprised of the domain I-domain III linker (residues 294-301).

In yet another embodiment, a druggable region is comprised of the fusion loop or a portion thereof. In another aspect, the present invention is directed towards a modulator that interacts with the fusion loop so as to preclude it from moving, thereby modulating the activity of the dengue virus E protein or other E protein.

Other regions of protein may in certain embodiments comprise a druggable region. For example, the hydrophobic core beneath the k1 hairpin or a portion thereof may comprise a druggable region. In another example, a druggable region may comprise domain II or a portion thereof. In still another example, a druggable region may comprise domain III or a portion thereof. In other examples, the pH-dependent hinge may serve as a druggable region. Further, a region or portion of a region of the E protein involved in trimerization, such as for example, the regions of domain II involved in trimerization, may present a druggable region. A region or a portion of a region involved in the stem fold back conformational change may comprise a druggable region, for example, such regions as the stem-domain II contact regions, the trimeric N terminal inner core, and C terminal outer layer surfaces on the clustered domains II, as well as the 53-residue stem. In certain embodiments, a druggable region may consist of the entire fragment of the E protein spanning residues 1-395.

Modulators of any of the above-described druggable regions may be used alone or in complementary approaches to treat dengue viral or other viral infections.

EQUIVALENTS

The present invention provides in part methods of screening novel druggable regions in dengue virus envelope protein to develop modulators of the protein. While specific embodiments of the subject invention have been discussed, the above specification is illustrative and not restrictive. Many variations of the invention will become apparent to those skilled in the art upon review of this specification. The appendant claims are not intended to claim all such embodiments and variations, and the full scope of the invention should be determined by reference to the claims, along with their full scope of equivalents, and the specification, along with such variations.

All publications and patents mentioned herein, including those items listed below, are hereby incorporated by reference in their entireties as if each individual publication or patent was specifically and individually indicated to be incorporated by reference. In case of conflict, the present application, including any definitions herein, will control.

Allison, S. L., et al. (2001) *J. Virol.*, 75, 4268-4275; Allison, S. L., et al. (1995) *J. Virol.*, 69, 695-700; Brünger, A. T., et al. (1998) *Acta Crystallogr. D.*, 54, 905-921; Burke, D. S, and Monath, T. P. (2001) *Fields Virology*, Lippincott Williams & Wilkins, Philadelphia, 1043-1125; Collaborative Computational Project, N. (1994) *Acta Crystallogr. D.*, 50, 760-763; Crill, W. D. and Roehrig, J. T. (2001) *J. Virol.*, 75, 7769-7773; Cuzzubbo, A. J., et al. (2001) *Clin. Diagn. Lab. Immunol.*, 8, 1150-1155; Esnouf, R. M. (1997) *J. Mol. Graphics*, 15, 132-134; Ferlenghi, I., et al. (2001) *Mol. Cell*, 7, 593-602; Gubler, D. J. (2002) *Trends Microbiol.*, 10, 100-103; Guirakhoo, F., et al. (1993) *Virology*, 194, 219-223; Hahn, Y. S., et al. (1988) *Virology*, 162, 167-180; Heinz, F. X. and Allison, S. L. (2001) *Curr. Opin. Microbiol.*, 4, 450-455; Hung, S. L., et al. (1999) *Virology*, 257, 156-167; Ivy, J., et al. (1997) United States Patent and Trademark Office, Hawaii Biotechnology Group, Inc., USA; Jones, T. A., et al. (1991) *Acta Crystallogr. A.*, 47, 110-119; Kawano, H., et al. (1993) *J. Virol.*, 67, 6567-6575; Kraulis, P. J. (1991) *J. Appl. Crystallogr.*, 24, 946-950; Kuhn, R. J., et al. (2002) *Cell*, 108, 717-725; La Fortelle, E. and Bricogne, G. (1997) *Methods in Enzymology*, 276, 472-494; Laskowski, R. A., et al. (1993) *J. Appl. Cryst.*, 26, 283-291; Lee, E., et al. (1997) *Virology*, 232, 281-290; Lescar, J., et al. (2001) *Cell*, 105, 137-148; Lindenbach, B. D. and Rice, C. M. (2001) *Fields Virology*, Lippincott Williams and Wilkins, Philadelphia, 991-1041; Merritt, E. A. and Bacon, D. J. (1997), *Methods in Enzymology*, 277, 505-524; Monath, T. P., et al. (2002) *J. Virol.*, 76, 1932-1943; Navaza J. (2001) *Acta Crystallogr. D.*, 57, 1367-1372; Otwinowski, Z. and Minor, W. (1997) *Methods in Enzymology*, 276, 307-326; Pletnev, A. G., et al. (1993) *J. Virol.*, 67, 4956-4963; Rey, F. A., et al. (1995) *Nature*, 375, 291-298; Skehel, J. J. and Wiley, D. C. (2000) *Annu. Rev. Biochem.*, 69, 531-569; Smith, T. J. et al. (1986) *Science*, 233, 1286-1293; Terwilliger, T. C. (1999) *Acta Crystallogr. D.*, 55, 1863-1871; Terwilliger, T. C. and Berendzen J. (1999) *Acta Crystallogr. D.*, 55, 849-861; Weissenhorn, W., et al. (1999) *Mol. Membr. Biol.*, 16, 3-9

Skehel, J. J. & Wiley, D. C. (2000) *Annu. Rev. Biochem.* 69, 531-569; Wilson, I. A., Skehel, J. J. & Wiley, D. C. (1981) *Nature* 289, 366-373; Bullough, P. A., Hughson, F. M., Skehel, J. J. & Wiley, D. C. (1994) *Nature* 371, 37-43; Chen, J., Skehel, J. J. & Wiley, D. C. (1999) *Proc. Natl. Acad. Sci. U.S.A.* 96, 8967-8972; Rey, F. A., Heinz, F. X., Mandl, C., Kunz, C. & Harrison, S. C. (1995) *Nature* 375, 291-298; Lescar, J. et al. (2001) *Cell* 105, 137-148; Modis, Y. & Harrison, S. C. (2003) *Proc. Natl. Acad. Sci. U.S.A.* 100, 6986-6991; Allison, S. L. et al. (1995) *J. Virol.* 69, 695-700; Ferlenghi, I. et al. (2001) *Mol. Cell* 7, 593-602; Kuhn, R. J. et al. (2002) *Cell* 108, 717-725; Allison, S. L., Schalich, J., Stiasny, K., Mandl, C. W. & Heinz, F. X. (2001) *J. Virol.* 75, 4268-4275; Levy-Mintz, P. & Kielian, M. (1991) *J. Virol.* 65, 4292-4300; Ahn, A., Gibbons, D. L. & Kielian, M. (2002) *J. Virol.* 76, 3267-3275; Stiasny, K., Allison, S. L., Schalich, J. & Heinz, F. X. (2002) *J. Virol.* 76, 3784-3790; Allison, S. L., Stiasny, K., Stadler, K., Mandl, C. W. & Heinz, F. X. (1999) *J. Virol.* 73, 5605-5612; Zhang, W. et al. (2003) *Nat. Struct. Biol.* in press; Carrell, R. W., Stein, P. E., Fermi, G. & Wardell, M. R. (1994) *Structure* 2, 257-270; Wimley, W. C. & White, S. H. (1992) *Biochemistry* 31, 12813-12818; Crill, W. D. & Roehrig, J. T. (2001) *J. Virol.* 75, 7769-7773; Jennings, A. D. et al. (1994) *J. Infect. Dis.* 169, 512-518; Lobigs, M. et al. (1990) *Virology* 176, 587-595; Holzmann, H., Heinz, F. X., Mandl, C. W., Guirakhoo, F. & Kunz, C. (1990) *J. Virol.* 64, 5156-5159; Jiang, W. R., Lowe, A., Higgs, S., Reid, H. & Gould, E. (1993) *J. Gen. Virol.* 74, 931-935; Gao, G. F., Hussain, M. H., Reid, H. W. & Gould, E. A. (1994) *J. Gen. Virol.* 75, 609-614; Cecilia, D. & Gould, E. A. (1991) *Virology* 181, 70-77; Chen, Y. et al. (1997) *Nat. Med.* 3, 866-871; Navarro-Sanchez, E. et al. (2003) *EMBO Rep.* 4, 1-6; Tassaneetrithep, B. et al. (2003) *J. Exp. Med.* 197, 823-829; Stiasny, K., Allison, S. L., Marchler-Bauer, A., Kunz, C. & Heinz, F. X. (1996) *J. Virol.* 70, 8142-8147; Chan, D. C. & Kim, P. S. (1998) *Cell* 93, 681-684; Kuzmin, P. I., Zimmerberg, J., Chizmadzhev, Y. A. & Cohen, F. S. (2001) *Proc. Natl. Acad. Sci. U.S.A.* 98, 7235-7240; Kozlov, M. M. & Chemomordik, L. V. (1998) *Biophys. J.* 75, 1384-1396; Razinkov, V. I., Melikyan, G. B. & Cohen, F. S. (1999) *Biophys. J.* 77, 3144-3151 Rand, R. P. & Parsegian, V. A. (1986) *Annu. Rev. Physiol.* 48, 201-212; Wahlberg, J. M., Bron, R., Wilschut, J. & Garoff, H. (1992) *J. Virol.* 66, 7309-7318; Han, X., Bushweller, J. H., Cafiso, D. S. & Tamm, L. K. (2001) *Nat. Struct. Biol.* 8, 715-720; Ito, H., Watanabe, S., Sanchez, A., Whitt, M. A. & Kawaoka, Y. (1999) *J. Virol.* 73, 8907-8912; Kemble, G. W., Danieli, T. & White, J. M. (1994) *Cell* 76, 383-391; Armstrong, R. T., Kushnir, A. S. & White, J. M. (2000) *J Cell Biol* 151, 425-437; Dutch, R. E. & Lamb, R. A. (2001) *J Virol* 75, 5363-5369; Baldwin, C. E., Sanders, R. W. & Berkhout, B. (2003) *Curr. Med. Chem.* 10, 1633-1642; Kilby, J. M. et al. (1998) *Nat. Med.* 4, 1302-1307; Hahn, Y. S. et al. (1988) *Virology* 162, 167-180; Schneider, I. (1972) *J Embryol Exp Morphol* 27, 353-365; Ivy, J., Nakano, E. & Clements, D. in United States Patent and Trademark Office (Hawaii Biotechnology Group, Inc., U.S.A., 1997); Cuzzubbo, A. J. et al. (2001) *Clin. Diagn. Lab. Immunol.* 8, 1150-1155; Otwinowski, Z. & Minor, W. (1997) *Methods in Enzymology* 276, 307-326; Navaza, J. (2001) *Acta Crystallogr. D* 57, 1367-1372; Collaborative Computational Project, N. The CCP4 suite: programs for protein crystallography. *Acta Crystallogr. D* 50, 760-763 (1994); Brünger, A. T. et al. (1998) *Acta Crystallogr. D* 54, 905-921; Jones, T. A., Zou, J. Y., Cowan, S. W. & Kjeldgaard. (1991) *Acta Crystallogr. A* 47, 110-119; Laskowski, R. A., MacArthur, M. W., Moss, D. S. & Thornton, J. M. PROCHECK: (1993) *J. Appl. Cryst.* 26, 283-291.

---

We claim:

1. A method for identifying a candidate therapeutic for a disease caused by a virus having class II E protein, comprising
contacting the virus having a dengue virus class II E protein with a compound,
assaying viral infectivity, wherein the inhibition of viral infectivity of said virus indicates a candidate therapeutic, wherein the dengue virus class II E protein consists of an amino acid sequence at least 20 amino acids but not greater than 394 amino acids in length having at least 85% identity along the length to the amino acid sequence of SEQ ID NO: 1 or 2, wherein amino acid residue 101 is Trp, amino acid residue 107 is Leu and amino acid residue 108 is Phe when numbered in accordance with SEQ ID NO: 1 or 2.

2. A method for identifying a candidate therapeutic for a disease caused by a virus having class II E protein, comprising
contacting a dengue virus class II E protein with a compound, wherein binding of said compound indicates a candidate therapeutic,
administering said compound to a subject, wherein the reduction of at least one symptom of said disease in a subject indicates a candidate therapeutic, and wherein the dengue virus class II E protein consists of an amino acid sequence at least 20 amino acids but not greater than 394 amino in length having at least 85% identity along the length to the amino acid sequence of SEQ ID NO: 1 or 2, wherein amino acid residue 101 is Trp, amino acid residue 107 is Leu and amino acid residue 108 is Phe when numbered in accordance with SEQ ID NO: 1 or 2.

3. The method of claim 1 or 2, wherein said compound is selected from the following classes of compounds: polypeptides, peptidomimetics, and small molecules.

4. The method of claim 1 or 2, wherein said disease is selected from the following group: dengue fever, dengue hemorrhagic fever, tick-borne encephalitis, West Nile virus disease, yellow fever, Kyasanur Forest disease, louping ill, hepatitis C, Ross River virus disease, and O'nyong fever.

5. The method of claim 1 or 2, wherein said compound is in a library of compounds.

6. The method of claim 1 or 2, wherein said library is generated using combinatorial synthetic methods.

7. The method of claim 2, wherein binding is determined using an in vitro assay.

8. The method of claim 1, wherein inhibition of viral infectivity of said virus is determined using an in vivo assay.

9. A method for identifying a candidate therapeutic for a disease caused by a virus having class II E protein, comprising
contacting a dengue virus class II E protein with a compound, wherein binding of said compound indicates a candidate therapeutic, wherein the dengue virus class II E protein consists of an amino acid sequence at least 20 amino acids but not greater than 394 amino acids in length having at least 85% identity along the length to the amino acid sequence of SEQ ID NO: 1, comprising residues 396-447, or fragments thereof, when numbered in accordance with SEQ ID NO: 1.

10. The method of claim 9, wherein said fragments comprises residues 396-429 (SEQ ID NO: 3) or 413-447 (SEQ ID NO: 4).

11. A method for identifying a candidate therapeutic for a disease caused by a virus having class II E protein, comprising
contacting a dengue virus class II E protein with a compound, wherein binding of said compound indicates a candidate therapeutic, wherein the dengue virus class II E protein consists of an amino acid sequence at least 20 amino acids but not greater than 394 amino acids in length having at least 85% identity along the length to the amino acid sequence of SEQ ID NO: 1 or 2, comprising at least one of residues 52-132 and 193-280, when numbered in accordance with SEQ ID NO: 1 or 2.

12. A method for identifying a candidate therapeutic for a disease caused by a virus having class II E protein, comprising
contacting a dengue virus class II E protein with a compound, wherein binding of said compound indicates a candidate therapeutic, wherein the dengue virus class II E protein consists of an amino acid sequence at least 20 amino acids but not greater than 394 amino acids in length having at least 85% identity along the length to the amino acid sequence of SEQ ID NO: 1 or 2, comprising at least one of residues 38-40, 143-147, 294-296, 294-301, 354-365, or the homologous residues in other class II E protein, when numbered in accordance with SEQ ID NO: 1 or 2.

* * * * *